(12) United States Patent
Ishihara et al.

(10) Patent No.: US 9,587,985 B2
(45) Date of Patent: Mar. 7, 2017

(54) OPTICAL TRANSMISSION DEVICE, LIGHT GUIDE PLUG, OPTICAL FIBER PLUG, LIGHT RECEPTION DEVICE, AND PORTABLE APPARATUS

(71) Applicant: SHARP KABUSHIKI KAISHA, Osaka-shi, Osaka (JP)

(72) Inventors: Takehisa Ishihara, Osaka (JP); Nobutaka Nishigaki, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/901,412

(22) PCT Filed: Jul. 3, 2014

(86) PCT No.: PCT/JP2014/067753
§ 371 (c)(1),
(2) Date: Dec. 28, 2015

(87) PCT Pub. No.: WO2015/019762
PCT Pub. Date: Feb. 12, 2015

(65) Prior Publication Data
US 2016/0153836 A1    Jun. 2, 2016

(30) Foreign Application Priority Data

Aug. 8, 2013 (JP) .................................. 2013-165595
Dec. 27, 2013 (JP) .................................. 2013-273288

(51) Int. Cl.
*G01J 5/04* (2006.01)
*G01J 3/10* (2006.01)
(Continued)

(52) U.S. Cl.
CPC ............. *G01J 5/048* (2013.01); *A61B 5/0086* (2013.01); *A61B 5/01* (2013.01); *A61B 5/6898* (2013.01);
(Continued)

(58) Field of Classification Search
CPC ........ G01J 5/02; G01J 5/04; G01J 5/14; G01J 5/08; G01J 5/048; A61B 5/01; G02B 6/4206
See application file for complete search history.

(56) References Cited

U.S. PATENT DOCUMENTS 4,876,851 A * 10/1989 Mueller .................. F02K 1/825
                                                          60/264
5,378,892 A *  1/1995 Levy ........................ G01J 5/06
                                                         250/352
(Continued)

FOREIGN PATENT DOCUMENTS

CN      101646383 A      2/2010
EP      1 182 848 A1     2/2002
(Continued)

*Primary Examiner* — Marcus Taningco
(74) *Attorney, Agent, or Firm* — Birch, Stewart, Kolasch & Birch, LLP

(57) ABSTRACT

A jack (10) of the invention includes a holding body (9) having an insertion hole (15) into which an optical plug is able to be inserted, a window material (6) through which infrared radiation passing through the insertion hole (15) is transmitted, and a light reception unit (2) which detects infrared radiation of 6 μm or more and 15 μm or less transmitted through the window material (6). The window material (6) is provided in the holding body (9) so as to prevent water from intruding into the light reception unit (2), and arranged at a bottom of the insertion hole (15). Thereby, it is possible to give a waterproof property to an element which receives infrared radiation without limitation to design or aesthetic appearance of an electronic apparatus.

18 Claims, 33 Drawing Sheets

(51) Int. Cl.
  *H04M 1/02* (2006.01)
  *G02B 6/42* (2006.01)
  *A61B 5/00* (2006.01)
  *A61B 5/01* (2006.01)
  *G01J 5/00* (2006.01)
  *G01J 5/02* (2006.01)
  *G01J 5/08* (2006.01)
  *G01J 5/14* (2006.01)
  *H04M 1/18* (2006.01)
  *H04M 1/215* (2006.01)

(52) U.S. Cl.
  CPC ............... *G01J 3/10* (2013.01); *G01J 5/0025* (2013.01); *G01J 5/0265* (2013.01); *G01J 5/049* (2013.01); *G01J 5/0875* (2013.01); *G01J 5/14* (2013.01); *G02B 6/4206* (2013.01); *G02B 6/4214* (2013.01); *G02B 6/4251* (2013.01); *G02B 6/4292* (2013.01); *H04M 1/0274* (2013.01); *A61B 2560/0223* (2013.01); *H04M 1/18* (2013.01); *H04M 1/215* (2013.01)

(56) References Cited

U.S. PATENT DOCUMENTS

| | | | | |
|---|---|---|---|---|
| 6,236,046 B1 * | 5/2001 | Watabe | ............ | G01J 5/04 250/330 |
| 2010/0017163 A1 | 1/2010 | Yamaguchi et al. | | |
| 2010/0158446 A1 | 6/2010 | Ohta | | |

FOREIGN PATENT DOCUMENTS

| | | |
|---|---|---|
| JP | 3001750 B2 | 1/2000 |
| JP | 2005-223629 A | 8/2005 |
| JP | 2007-114673 A | 5/2007 |
| JP | 2011-216741 A | 10/2011 |
| JP | 2012-231309 A | 11/2012 |
| WO | WO 00/72554 A1 | 11/2000 |
| WO | WO 2008/142777 A1 | 11/2008 |
| WO | WO 2011/030532 A1 | 3/2011 |

* cited by examiner

FIG. 7
(a)
PARALLEL ARRANGEMENT
APERTURE RATIO(%) = $\dfrac{78.5 \times d^2}{p^2}$
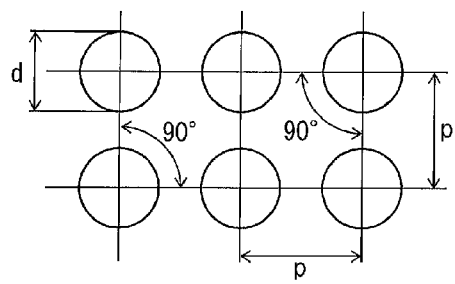
(b)
45° STAGGERED ARRANGEMENT
APERTURE RATIO(%) = $\dfrac{157 \times d^2}{p^2}$
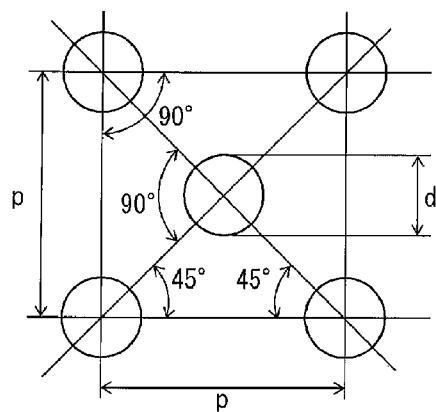

FIG. 24
(a)
PARALLEL ARRANGEMENT
APERTURE RATIO(%) = $\dfrac{78.5 \times d^2}{p^2}$
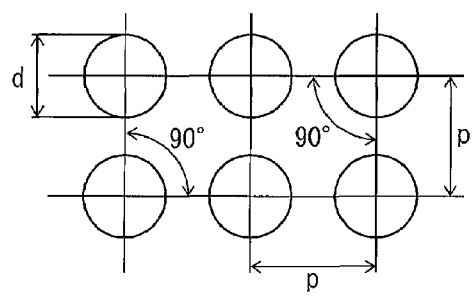
(b)
45° STAGGERED ARRANGEMENT
APERTURE RATIO(%) = $\dfrac{157 \times d^2}{p^2}$
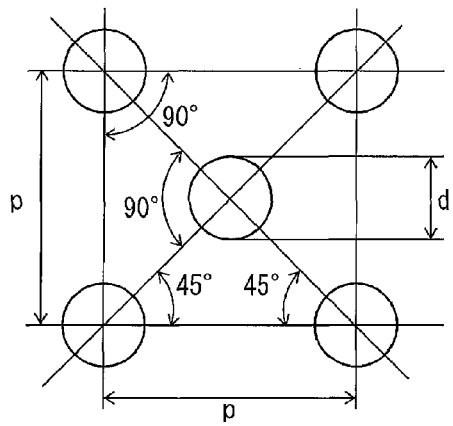

FIG. 35
(a)
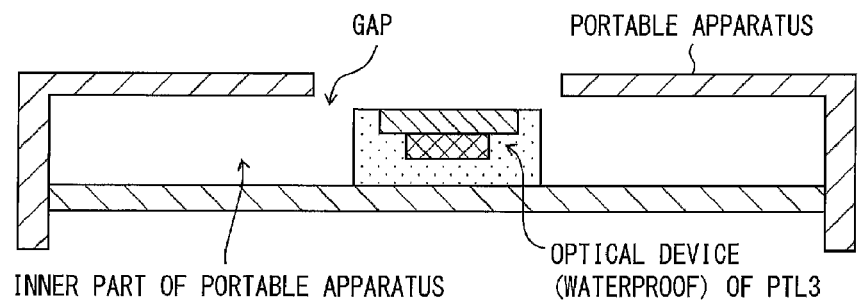
(b)
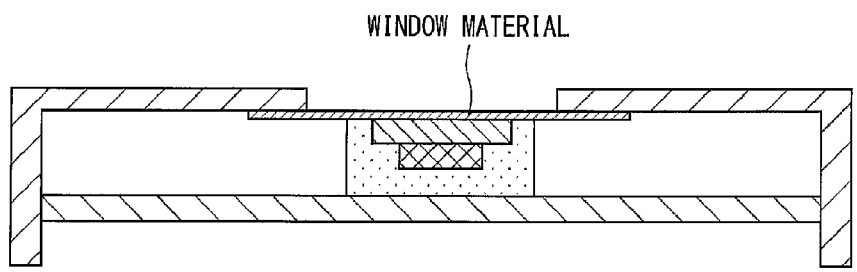

OPTICAL TRANSMISSION DEVICE, LIGHT GUIDE PLUG, OPTICAL FIBER PLUG, LIGHT RECEPTION DEVICE, AND PORTABLE APPARATUS

TECHNICAL FIELD

The present invention relates to an optical transmission device, a light guide plug, an optical fiber plug, a light reception device and a portable apparatus, and, particularly, relates to an optical transmission device which transmits infrared radiation and a light reception device which receives the infrared radiation.

BACKGROUND ART

Clinical thermometers which receive infrared radiation emitted from a human body and display temperature according to the infrared radiation have been used.

For example, PTL 1 discloses an ear thermometer provided with an instruction unit that is arranged in a front surface of a housing in order to instruct start of measurement of body temperature, a rotation unit that, at a position on a rear surface of the housing, which is opposite to a position where the instruction unit is disposed, rotates around a normal line at the position on the rear surface, and a probe that is connected to the rotation unit at a predetermined angle with respect to the normal line and that has an infrared sensor and a thermistor mounted on a tip position thereof.

In these years, an infrared sensor is mounted on a portable apparatus and is used also as a temperature sensor or a human detection sensor.

For example, PTL 2 discloses a portable wireless terminal having an infrared sensor that is incorporated in a vicinity of a liquid crystal display screen thereof and detects temperature of a forehead of a user in a non-contact manner.

Moreover, PTL 3 discloses an optical device in which an optical element is firmly fixed on an optical filter physically and a light reception/emission surface of the optical element is not exposed.

Further, PTL 4 discloses a portable electronic apparatus provided with a human detection sensor having an infrared sensor for detecting infrared radiation generated from a human body and judging means for judging approach of a human body by a first output signal from the infrared sensor.

Infrared sensors provided in portable apparatuses are arranged at positions according to respective purposes thereof. For example, the vicinity of the liquid crystal display screen is selected for the position at which the infrared sensor of PTL 2 is provided as a position to which a forehead of a user may come close. The human detection sensor of PTL 4 is also similarly provided in the vicinity of a liquid crystal display screen.

On the other hand, when an optical fiber is used, limitation on the position of the infrared sensor is eliminated.

For example, PTL 5 discloses a plug-jack type optical and electric shared transmission device. In the optical and electric shared transmission device, when an optical fiber plug is inserted into a common insertion hole provided in a holding body that stores and holds an optical semiconductor element and an electrical connection terminal, optical transmission is performed on the optical semiconductor element in the holding body. On the other hand, when an electrical plug is inserted into the insertion hole, each electrode unit of the electrical connection terminal and the electrical plug are electrically connected, so that electrical signal transmission is performed.

CITATION LIST

Patent Literature

PTL 1: International Publication "No. WO2011/030532 (published on Mar. 17, 2011)"
PTL 2: Japanese Unexamined Patent Application Publication "No. 2012-231309 (published on Nov. 22, 2012)"
PTL 3: Japanese Unexamined Patent Application Publication "No. 2011-216741 (published on Oct. 27, 2011)"
PTL 4: Japanese Unexamined Patent Application Publication "No. 2005-223629 (published on Aug. 18, 2005)"
PTL 5: Japanese Patent Publication "No. 3001750 (registered on Nov. 12, 1999)"

Summary of Invention

Technical Problem

When an infrared sensor is provided in a portable apparatus or the like to be used, it becomes necessary to take a dustproof countermeasure for preventing intrusion of dirt and dust into the portable apparatus, or a waterproof countermeasure for preventing intrusion of water in addition to the dustproof countermeasure. For example, in a case where an infrared sensor is mounted on a portable apparatus and used as a temperature sensor or a human detection sensor like in PTL 2 or 3, there is a risk that particularly dust or steam, vapor, or moisture such as sweat from a human body intrudes into the periphery of the infrared sensor. For example, as illustrated in FIG. 35(a), in a case where an opening is formed in a housing of the portable apparatus and the optical device of PTL 3 is arranged so as to face the opening, a gap is formed between the optical device and the housing. Thus, there is a possibility that dust or moisture intrudes into an inner part of the portable apparatus from the gap. In order to prevent dust and moisture from intruding into the gap, it is necessary for the housing to have a waterproof property and infrared transmissivity. Then, by providing, for example, a window material illustrated in FIG. 35(b), it is possible to prevent dust and moisture from intruding into the inner part of the housing of the portable apparatus.

However, since a material having a dustproof property or a waterproof property and infrared transmissivity is not able to be dyed by using a dye which absorbs infrared radiation, a color thereof is limited to white, black, a metal color, or the like which is an original color of the material. On the other hand, a portable apparatus has a housing of various colors and is excellent in design. Accordingly, in order to give a dustproof property or a waterproof property to an infrared sensor, necessity of sacrificing the color and design of the housing of the portable apparatus is caused.

For example, since the infrared sensor is provided in the vicinity of a surface of a housing in the apparatuses disclosed in PTLs 2 to 4, it is difficult to add a member, which gives a dustproof property or a waterproof property to the infrared sensor, without spoiling a color, design, nor beauty of the housing.

The invention has been made in order to solve the aforementioned problems, and an object thereof is to provide: an optical transmission device which gives a waterproof property and infrared transmissivity to an infrared sensor without affecting a color or design of a portable apparatus; a light guide plug; an optical fiber plug; a light reception device; and the portable apparatus.

Solution to Problem

In order to solve the aforementioned problems, an optical transmission device according to an aspect of the invention includes a holding body having an insertion hole into which an optical fiber plug is able to be inserted, a window material through which infrared radiation passing through the insertion hole is transmitted, and a first optical element which detects infrared radiation of 6 µm or more and 15 µm or less transmitted through the window material, in which the window material is provided in the holding body so as to prevent water from intruding into the first optical element, and arranged at a bottom of the insertion hole.

Moreover, a light guide plug according to an aspect of the invention is a light guide plug which is inserted into the insertion hole of the aforementioned optical transmission device, and guides infrared radiation to the first optical element of the optical transmission device. The light guide plug includes an opening through which the infrared radiation enters, an optical system which changes an advancing direction of the infrared radiation entering the opening, and a mirror surface in a cylindrical shape which guides the infrared radiation, advancing direction of which is changed by the optical system, to the first optical element.

Moreover, an optical fiber plug according to an aspect of the invention is an optical fiber plug which is inserted into the insertion hole of the aforementioned optical transmission device, and guides infrared radiation to the first optical element of the optical transmission device. The optical fiber plug includes a light collecting unit which collects the infrared radiation and an optical fiber which guides the infrared radiation incident on the light collecting unit to the first optical element.

Moreover a light reception device according to an aspect of the invention includes a holding body in which an insertion hole is formed, a window material which is arranged at a bottom side of the insertion hole and through which infrared radiation passing through the insertion hole is transmitted, an infrared sensor which detects the infrared radiation transmitted through the window material, and a field of view restriction member that blocks infrared radiation which is generated in accordance with temperature of an inner surface of the insertion hole and is possible to be incident on the infrared sensor.

Moreover, a light reception device according to an aspect of the invention includes a holding body in which an insertion hole is formed, a window material which is arranged at a bottom side of the insertion hole and through which infrared radiation passing through the insertion hole is transmitted, and an infrared sensor which detects the infrared radiation transmitted through the window material, in which the infrared sensor includes a first optical element which detects infrared radiation transmitted through the window material and a second optical element which detects infrared radiation generated in accordance with temperature of an inner surface of the insertion hole more than the first optical element.

Moreover, an electrical jack according to an aspect of the invention includes a holding body in which an insertion hole is formed, a window material which is arranged at a bottom side of the insertion hole and through which infrared radiation passing through the insertion hole is transmitted, the insertion hole allowing insertion of an electrical plug, and an electrical connection terminal which is electrically connected to the electrical plug in a case where the electrical plug is inserted, in which a thermopile which, in a case where the insertion hole is open, detects infrared radiation transmitted through the window material is further included.

Moreover an electrical jack, according to an aspect of the invention includes a holding body in which an insertion hole is formed, a window material which is arranged at a bottom side of the insertion hole and through which infrared radiation passing through the insertion hole is transmitted the insertion hole allowing insertion of an electrical plug and an electrical connection terminal which is electrically connected to the electrical plug in a case where the electrical plug is inserted, in which a thermopile which, in a case where the insertion hole is open, detects infrared radiation outside via the insertion hole is further included.

Moreover, in a portable apparatus according to an aspect of the invention, a window material, through which infrared radiation passing through a concave part formed in a housing is transmitted, is arranged at a bottom side of the concave part, and an infrared sensor which detects the infrared radiation transmitted through the window material is provided.

Moreover, in a portable apparatus according to an aspect of the invention, a window material, through which infrared radiation passing through an insertion hole formed in a side surface of a housing is transmitted, is arranged at a bottom side of the insertion hole, and an infrared sensor which detects the infrared radiation transmitted through the window material is provided.

Advantageous Effects of Invention

According to an aspect of the invention, realized is an effect of providing: an optical transmission device which gives a waterproof property and infrared transmissivity to an infrared sensor without affecting a color or design of a portable apparatus; a light guide plug; an optical fiber plug; a light reception device; and the portable apparatus.

BRIEF DESCRIPTION OF DRAWINGS

FIG. 7(a) is an illustration for explaining an aperture ratio of the field of view restriction member, and is a view illustrating a state where holes P are arrayed in parallel arrangement, and (b) is a view illustrating a state where the holes P are arrayed in 45° staggered arrangement.

FIG. 24(a) is for explaining an aperture ratio of the field of view restriction member, and is a view illustrating a state where holes P are arrayed in parallel arrangement, and (b) is a view illustrating a state where the holes P are arrayed in 45° staggered arrangement.

FIG. 35(a) is a view illustrating a configuration example when a conventional optical device of PTL 3 is provided in a portable terminal apparatus, and (b) is a view for comparing a configuration example, when a window material is provided, with (a).

DESCRIPTION OF EMBODIMENTS

[Embodiment 1]

An embodiment of the invention will be described in detail below based on FIG. 1 to FIG. 6 and FIG. 11. Description will be given here for an optical transmission device according to the invention by, as an example, taking a jack (optical transmission device) 10 configured by using a basic structure of an earphone jack, to which an electrical plug used for electric transmission is inserted, generally mounted on a portable terminal, a smartphone (electronic apparatus), or the like. That is, the jack 10 is an optical and electric shared jack which is usable with an electrical plug or an optical plug (optical fiber plug or the like) inserted thereinto. Hereinafter, it is assumed that the jack 10 includes an optical element which detects infrared radiation and the optical transmission device according to the invention is realized as the jack 10. However, the jack 10 is not necessarily an optical and electric shared jack, and the optical transmission device according to the invention is applicable to a tubular-shaped jack which is configured to be dedicated to an optical plug and into which any plug is able to be inserted.

(Schematic Configuration of Jack 10)

Figure 1:
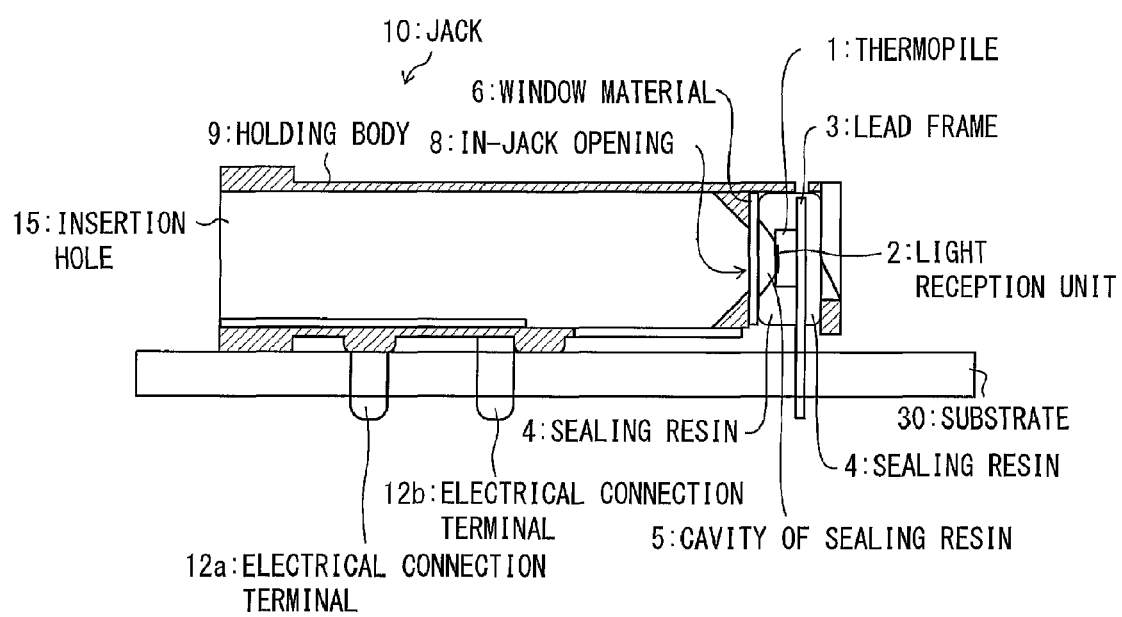
FIG. 1 is a sectional view illustrating an example of a structure of a jack according to Embodiment 1 of the invention.

In an embodiment of the invention, the jack 10 is an optical and electric shared jack, which is provided in an electronic apparatus, a smartphone, or the like, as described above. First, an example of a structure of the jack 10 will be described by using FIG. 1. FIG. 1 is a sectional view illustrating an example of the structure of the jack 10 according to Embodiment 1 of the invention.

The jack 10 includes a window material 6, an in-jack opening 8, a holding body 9, electrical connection terminals 12a and 12b, and an insertion hole 15. The jack 10 further includes a thermopile 1, a light reception unit (first optical element) 2, a lead frame 3, a sealing resin 4, and a cavity of sealing resin 5. The jack 10 is fixed to a substrate 30 in an inner part of an electronic apparatus, a smartphone, or the like. That is, when an optical plug or an electrical plug is selectively connected, the jack 10 has a corresponding function of an optical transmission function or an electric transmission function.

Here, the holding body 9 and the insertion hole 15 will be described briefly. Note that, the window material 6, the in-jack opening 8, the thermopile 1, the light reception unit 2, the lead frame 3, the sealing resin 4, and the cavity of sealing resin 5 will be described below by using FIGS. 2(a) and (b).

The holding body 9 is a substantially tubular member molded by using non-transparent resin. The thermopile 1, the light reception unit 2 (first optical element), and the lead frame 3 are fixed to and stored in the holding body 9 by using adhesive resin (not illustrated). A conductive member (not illustrated) which makes contact with and is electrically connected to a side surface of an electrical plug to be inserted is provided in the insertion hole 15 side of the holding body 9, and the conductive member is connected to each of the electrical connection terminals 12a and 12b so as to allow electric transmission.

One of the electrical connection terminals 12a and 12b is in contact with the conductive member (not illustrated) of the holding member 9 of the jack 10, and the other of the electrical connection terminals 12a and 12b is connected to an electronic circuit of an electronic apparatus (not illustrated). When an electrical plug (electrical plug used for electric transmission which is not illustrated) is inserted into the insertion hole 15 of the jack 10, the electrical connection terminals 12a and 12b function as terminals used for transmission of an electric signal, so that electrical connection of the electrical plug and the electronic circuit of the electronic apparatus or a smartphone (not illustrated) is established. An example in which the insertion hole 15 is provided with two electrical connection terminals of the electrical connection terminals 12a and 12b is given here, but this number may be one or may be two or more, and not particularly limited.

That is, the insertion hole 15 may be configured so as to allow the electrical plug used for electric transmission to be inserted thereinto, and may further include a plurality of electrical connection terminals which are configured so as to allow electrical connection to the electrical plug inserted into the insertion hole 15.

The insertion hole 15 is a space into which an optical plug or an electrical plug which is compatible with the jack 10 is inserted. A distance from an end part of the jack 10, in which an opening of the insertion hole 15 is provided, to a surface of the window material 6, which is closer to the opening of the insertion hole 15, only needs to be 15 mm or more. Thereby, it is possible to prevent a general distributed electrical plug, even when being inserted, from abutting and damaging the window material 6. However, in the case of inserting an optical plug (optical plug 20 of FIG. 3) into the insertion hole 15 to use optical coupling, it is desirable that a distance between a tip end surface of the optical plug (optical plug tip end surface 23 of FIG. 3) and the light reception unit 2 is shorter. For example, the distance from the end part of the jack 10, in which the opening of the insertion hole 15 is provided, to the surface of the window material 6, which is closer to the opening of the insertion hole 15, may be 15.1 mm.

(Schematic Configuration Around Light Reception Unit 2 of Jack 10)

Next, a structure of a vicinity of the light reception unit 2 of the jack 10 will be described by using FIG. 2(a). FIG. 2(a) is a sectional view illustrating a structure around the in-jack opening 8 of the jack 10 of FIG. 1.

The window material 6 is a material for waterproofing, which is provided in order to prevent moisture, such as vapor, which intrudes from a side of the opening of the insertion hole 15 of the jack 10 from directly impinging on the thermopile 1 and the light reception unit 2. Further, the window material 6 has transmissivity which allows infrared radiation having a wavelength of 1 to 15 μm to be transmitted therethrough, and more preferably has transmissivity which allows infrared radiation having a wavelength of 6 to 15 μm to be transmitted therethrough. Zinc selenide (ZnSe) having toxicity, calcium fluoride (CaF) having deliquescency, or the like makes the window material 6 look transparent with visible light, but is not suitable therefor. As the window material 6, one obtained by molding, for example, high density polyethylene, silicon, germanium, or the like is able to be applied. Because of being provided deep in (at a bottom of) the insertion hole 15 of the jack 10, the window material 6 is not exposed to a front surface of a housing of an electronic apparatus or a smartphone, which includes the jack 10. Accordingly, a color, design, or beauty of an appearance of the front surface of the housing of the electronic apparatus or the smartphone is not affected, so that it is possible to use any material, which has the waterproof property and optical transmissivity as described above, as the window material 6.

According to the Wien's displacement law that a product of a wavelength with which a quantity of radiation becomes maximum and temperature at that time is a fixed number, radiation temperature of an object to be measured which emits infrared radiation having a wavelength of 6 to 15 μm is about −80° C. to 300° C. That is, based on the infrared radiation having the wavelength of 6 to 15 μm, which reaches the light reception unit 2, it is possible to measure temperature of the object to be measured, which is about −80° C. to 300° C. Thus, by using the jack 10, it is possible to measure temperature of a frozen food, water temperature, body temperature, temperature of a food cooked by heating, and the like without making contact with the object to be measured. A specific application example will be described in detail below.

The in-jack opening 8 is formed in a side which is farthest from the opening of the insertion hole 15 of the jack 10. The tip end surface of the electrical plug or the optical plug (for example, refer to the optical plug tip end surface 23 of FIG. 3) which is inserted into the jack 10 is provided in a side facing the light reception unit 2 included in the thermopile 1. To the in-jack opening 8, the above-described window material 6 is fixed with an adhesive, so that intrusion of water into the thermopile 1 and the light reception unit 2 is prevented. It is also possible to prevent intrusion of water into an inner part of the electronic apparatus by the window material 6.

In the lead frame 3, the thermopile 1 including the light reception unit 2 which detects infrared radiation of 1 to 15 μm is fixed (die-bonded) at a predetermined position, and the thermopile 1 and the lead frame 3 are electrically connected with a wire which is not illustrated. A part of the lead frame 3 is fixed to the substrate 30 and electrically connected to the electronic circuit of the electronic apparatus or the smartphone.

The thermopile 1, the light reception unit 2, and the lead frame 3 are sealed by, for example, epoxy resin, and a surface of the light reception unit 2, which is in a side of the opening of the insertion hole 15, faces the cavity of sealing resin 5. Thereby, infrared radiation which has been emitted from an object to be measured and has passed through the window material 6 reaches the light reception unit 2 without being absorbed by the sealing resin 4. Accordingly, it is possible to measure temperature of the object to be measured by using the jack 10.

The window material 6 is disposed in front of the cavity of sealing resin 5. The window material 6 is fixed to the sealing resin 4 with an adhesive at an edge part of the cavity of sealing resin 5, and intrusion of water from the insertion hole 15 into the cavity of sealing resin 5 is prevented. That is, the cavity of sealing resin 5 is a space surrounded by the thermopile 1, the light reception unit 2, the sealing resin 4, and the window material 6.

Figure 2:
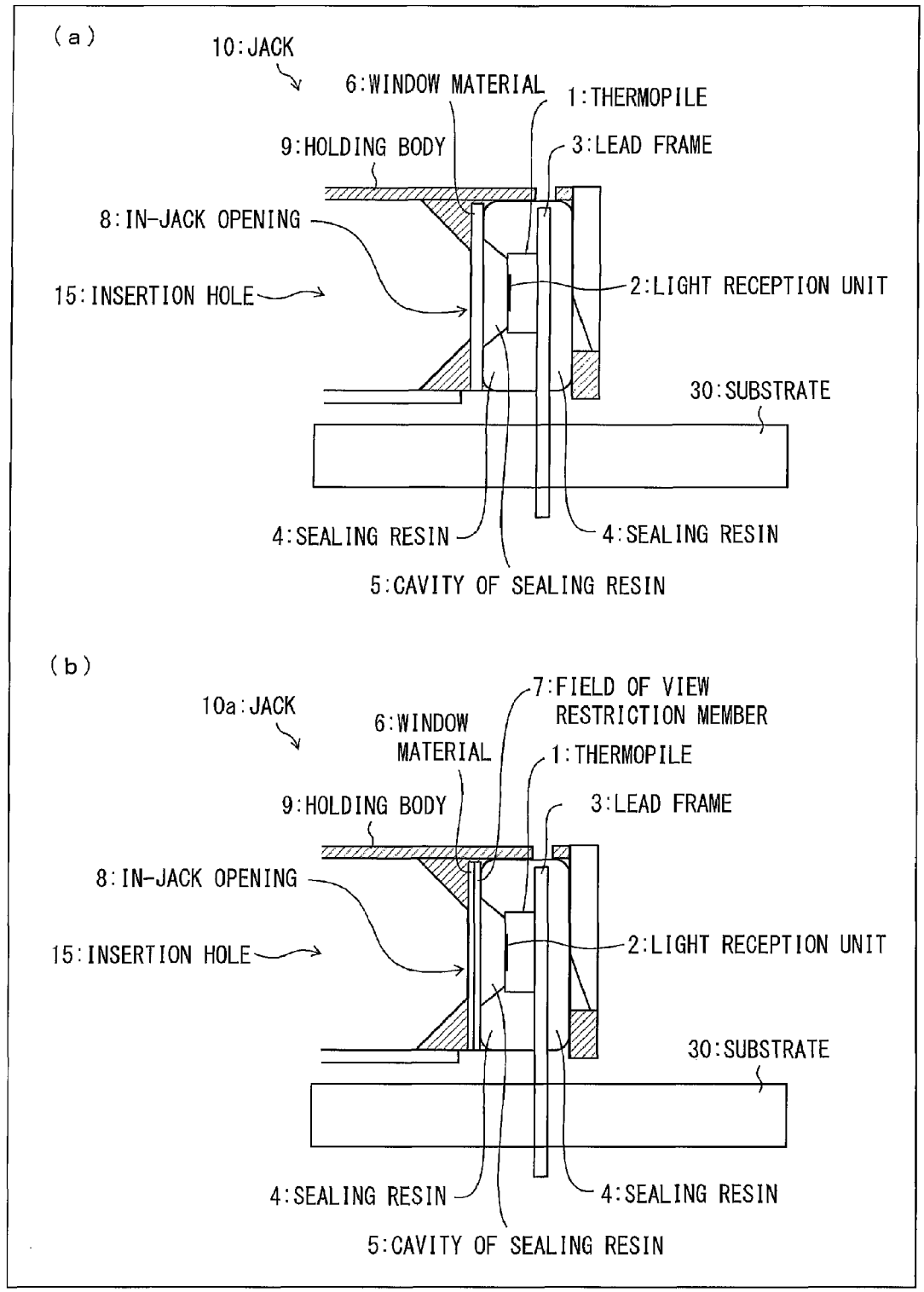
FIG. 2(a) is a sectional view illustrating a structure around an in-jack opening of the jack of FIG. 1, and (b) is a sectional view illustrating a structure in a case where a field of view restriction member is arranged in a vicinity of a window material of the jack of FIG. 1.

Next, another example of the structure of the vicinity of the light reception unit 2 of the jack 10 will be described by using FIG. 2(*b*). FIG. 2(*b*) is a sectional view illustrating a structure of a jack (optical transmission device) 10*a* in which a field of view restriction member 7 is arranged in a vicinity of the window material 6 of the jack 10 of FIG. 1. Note that, for convenience of description, the same reference signs are assigned to members having the same functions as those of the members described with FIG. 2(*a*), and description thereof will be omitted.

The field of view restriction member 7 is a member having a function of restricting an angle at which light radiated from an object to be measured and reaching the light reception unit 2 is made incident on the light reception unit 2. As illustrated in FIG. 2(*b*), the field of view restriction member 7 is provided along the window material 6 so as to be superimposed on the window material 6, and fixed to the sealing resin 4 with an adhesive at the edge part of the cavity of sealing resin 5. The field of view restriction member 7 is formed by providing many minute through holes (holes P in FIG. 6) by laser-beam machining in, for example, a polyimide plate which absorbs infrared radiation. That is, the infrared radiation emitted from the object to be measured is transmitted through the window material 6 and then passes through the through holes provided in the field of view restriction member 7 to reach the light reception unit 2. Note that, a specific example of a structure of the field of view restriction member 7 and a function thereof will be described in detail below.

(Relation Between Jack 10 and Optical Plug 20)

Figure 3:
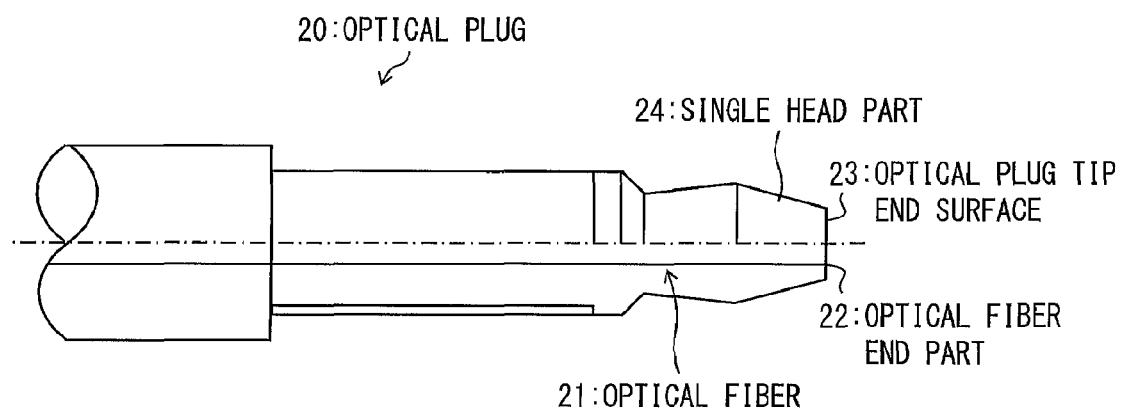
FIG. 3 is a partial sectional view illustrating an example of a structure of an optical plug capable of being inserted into the jack of FIG. 1.
Figure 4:
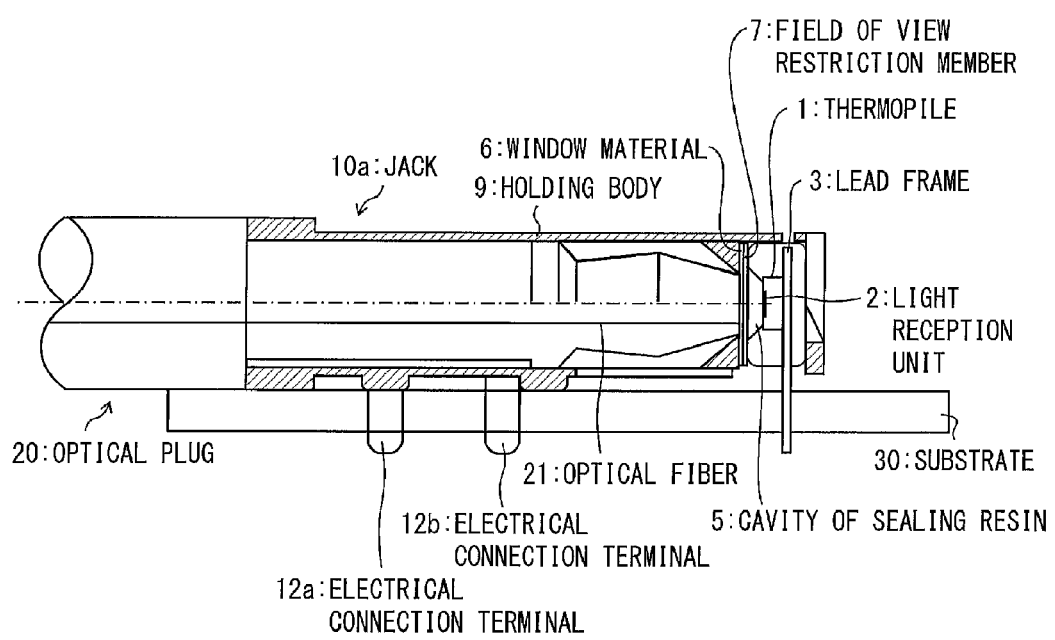
FIG. 4 is a partial sectional view of the jack and the optical plug, which illustrates a configuration when the optical plug illustrated in FIG. 3 is inserted into the jack illustrated in FIG. 2(b).

Next, an optical plug which is compatible with the jack 10 will be described briefly by using FIG. 3 and FIG. 4. FIG. 3 is a partial sectional view illustrating an example of a structure of the optical plug (optical fiber plug) 20 capable of being inserted into the jack 10 of FIG. 1. An upper part from a dash-dot line of FIG. 3 illustrates an appearance diagram of the optical plug 20, and a lower portion illustrates a sectional view illustrating an inner structure of the optical plug 20. Moreover, FIG. 4 is a sectional view of the jack 10*a* and a partial sectional view of the optical plug 20 which illustrate a state where the optical plug 20 illustrated in FIG. 3 is inserted into the jack 10*a* (optical transmission device) illustrated in FIG. 2(*b*).

As illustrated in FIG. 3, the optical plug 20 includes an optical fiber 21, an optical fiber end part 22, the optical plug tip end surface 23, and a single head part 24.

The optical fiber 21 is a fiber which is provided so as to pass through almost the center of an inner part of the optical plug 20 and which has a function of transmitting light, and an example thereof includes a PIR fiber which transmits infrared radiation at a low attenuation factor. As the optical fiber 21, it is desirable to use one having high flexibility and no toxicity. As a core material of the optical fiber 21, for example, AgCl/AgBr is used.

The optical plug tip end surface 23 includes the optical fiber end part 22 from which infrared radiation transmitted through the optical fiber 21 is emitted. When the optical plug 20 is inserted into the jack 10, a part of the infrared radiation output from the optical fiber end part 22 is made incident on the light reception unit 2 of the jack 10.

When the optical plug 20 is inserted into the jack 10, the single head part 24 is formed in a part inserted into a deepest part of the jack, and a constricted part is formed in a side of a base part of the single head part 24. That is, the optical plug 20 has a shape similar to that of an insertion part of an existing small-sized single-head electrical plug, which has been generally distributed.

When the optical plug 20 is inserted into the insertion hole 15 of the jack 10*a*, the optical plug 20 is held inside the holding body 9 as illustrated in FIG. 4. At this time, the optical plug tip end surface 23 of the optical plug 20 becomes proximate to or abuts the window material 6 of the jack 10*a*. Thereby, the optical fiber end part 22 included in the optical plug tip end surface 23 also becomes proximate to or abuts the window material 6 of the jack 10*a*. Thus, the infrared radiation emitted through the optical fiber 21 is output from the optical fiber end part 22 and is transmitted through the window material 6. Among the infrared radiation which is transmitted through the window material 6, infrared radiation which has passed through the through holes (holes P of FIG. 6) provided in the field of view restriction member 7 then goes through the cavity of sealing resin 5 and is made incident on the light reception unit 2.

(As to Field of View of Light Reception Unit 2)

Figure 5:
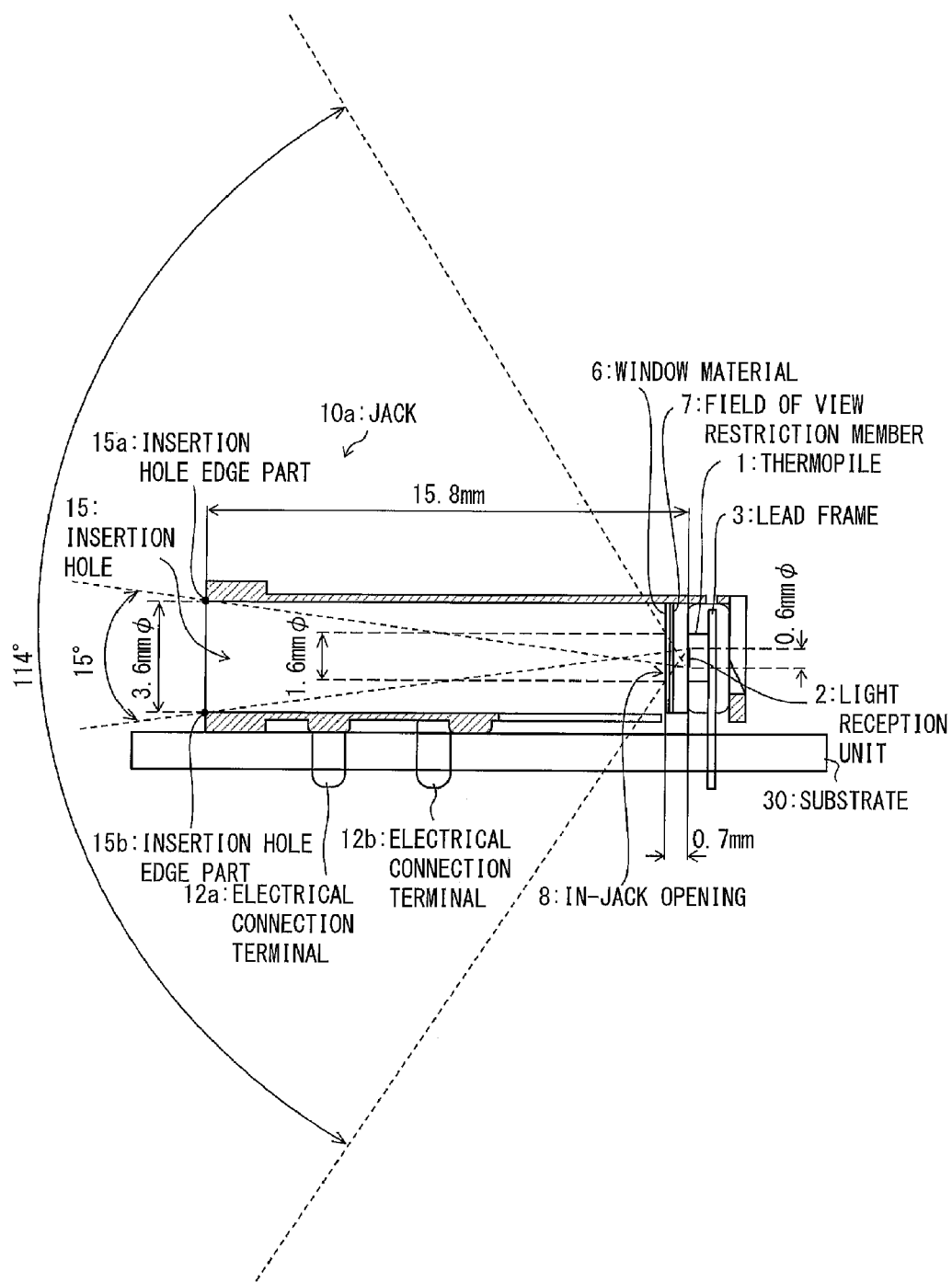
FIG. 5 is a sectional view for explaining an FOV of a light reception unit of a thermopile provided in the jack illustrated in FIG. 2(b).

Next, description will be given for, in a case where a plug such as the optical plug 20 is not inserted into the insertion hole 15 of the jack 10a, an incident angle of infrared radiation which can be made incident on the light reception unit 2, that is, a field of view (FOV) of the light reception unit 2 of the jack 10a. Here, the FOV of the light reception unit 2 is a maximum value of a difference of incident angles of light incident on the light reception unit 2. FIG. 5 is a sectional view for explaining the FOV of the light reception unit 2 of the thermopile 1 provided in the jack 10a illustrated in FIG. 2(b).

In an example illustrated in FIG. 5, it is set that a light receiving diameter which is a diameter of the light reception unit 2 of the thermopile 1 is 0.6 mm, an inner diameter (diameter) of the insertion hole 15 of the jack 10a is 3.6 mm, and a shortest distance from a line connecting an insertion hole edge part 15a and an insertion hole edge part 15b to the surface of the light reception unit 2 of the thermopile 1 is 15.8 mm. In addition, it is set that an opening diameter (diameter) of the in-jack opening 8 is 1.6 mm, and a distance between the opening of the in-jack opening 8 and the light reception unit 2 of the thermopile 1 is 0.7 mm.

When reaching the light reception unit 2, infrared radiation which is emitted from an object to be measured outside the insertion hole 15 of the jack 10a passes through the opening of the insertion hole 15, so that the FOV of the light reception unit 2 is about 15°. That is, since the light reception unit 2 is provided at a bottom part of the insertion hole 15 of the jack 10a which has a depth, the FOV of the light reception unit 2 is restricted.

On the other hand, in a case where the field of view restriction member 7 is not provided, the light reception unit 2 receives infrared radiation passing through the in-jack opening 8, so that an FOV thereof is about 114° in an example illustrated in FIG. 5. Accordingly, in addition to the infrared radiation which is emitted from the object to be measured outside the insertion hole 15, infrared radiation emitted from a surface of a side in which the insertion hole 15 of the holding body 9 is formed (that is, an inner surface of the jack 10a) is also made incident on the light reception unit 2.

In a case where, in a radiation temperature sensor having a cylindrical shape like the jack 10a, a sensor receiving infrared radiation is provided deep in the cylinder, it is devised such that, by setting an inner surface of the cylinder as a mirror surface, an amount of infrared radiation emitted from the inner surface of the cylinder is relatively reduced. However, the cylinder having the inner surface set as the mirror surface becomes a light guiding path of infrared radiation, resulting that an FOV becomes widened. Then, in order to prevent the FOV from being widened, a lens for restricting a field of view of infrared radiation incident on the radiation temperature sensor is normally provided in an opening part of the cylinder. However, the jack 10a is used with the optical plug 20 inserted thereinto, so that it is unable to block the insertion hole 15 by providing a lens, for example, near the insertion hole edge part 15a. Then, it is considered to restrict the FOV of the light reception unit 2 to 15° by providing a thin optical system such as a silicon diffraction lens 70 (FIG. 34) in the in-jack opening 8.

However, in the case of providing the silicon diffraction lens 70 in the in-jack opening 8, it is necessary to set a distance between the silicon diffraction lens 70 and the light reception unit 2 long, so that it becomes necessary to set a depth of the jack 10a longer than a depth of an electrical jack which has been distributed. Moreover, a problem of design that an optical axis of the light reception unit 2 and the silicon diffraction lens 70 requires to be adjusted is posed. This will be described briefly below by using FIG. 34.

Figure 34:
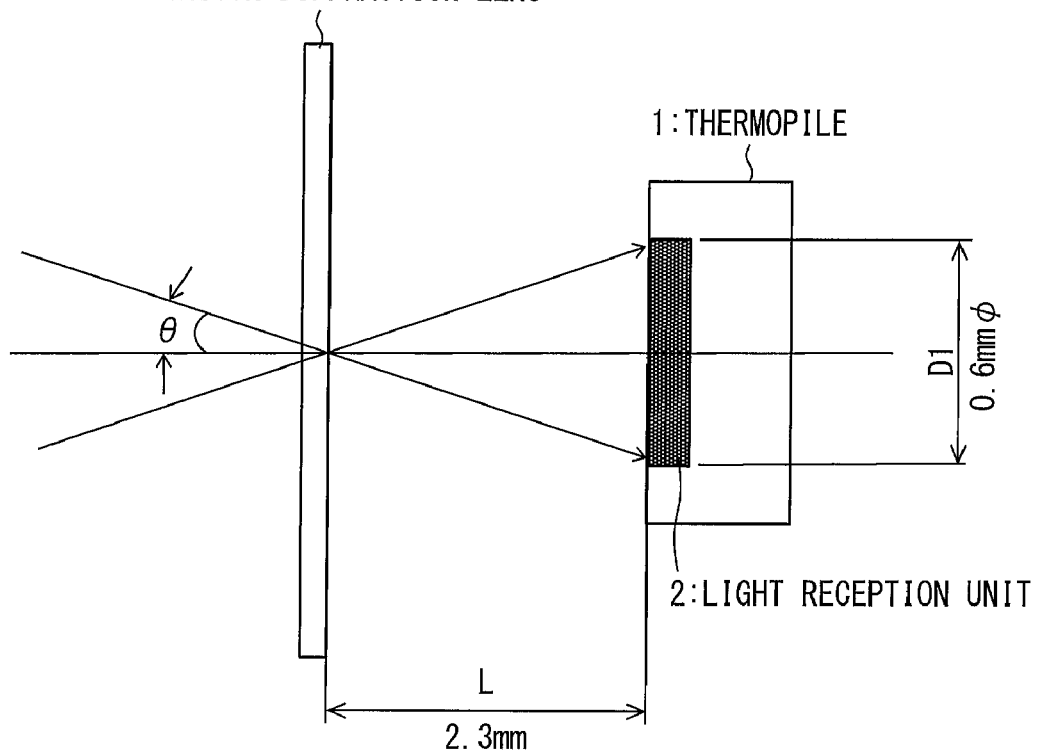
FIG. 34 is a view for explaining, in a case where the FOV of the light reception unit 2 is restricted to 15° by providing a silicon diffraction lens in an in-jack opening in the jack of FIG. 5 or in an in-electrical jack opening in the electrical jack of FIG. 22, a distance between the light reception unit and the silicon diffraction lens.

FIG. 34 is a view for explaining a distance between the light reception unit 2 and the silicon diffraction lens 70 in a case where the FOV of the light reception unit 2 is restricted to 15° by providing the silicon diffraction lens 70 in the in-jack opening 8 in the jack 10a of FIG. 5.

As illustrated in FIG. 34, the optical axis is adjusted so that infrared radiation passing through the center of the silicon diffraction lens 70 reaches the center of the light reception unit 2. When the diameter of the light reception unit 2 is 0.6 mm, a distance L between the light reception unit 2 and the silicon diffraction lens 70, which is necessary for setting an angle θ to be 7.5° is about 2.3 mm. Accordingly, compared to the example illustrated in FIG. 5, in which the distance between the in-jack opening 8 and the light reception unit 2 is 0.7 mm, it becomes necessary to set the jack 10a longer by 1.5 mm or more. Then, in the jack 10a according to the present embodiment, applied is the field of view restriction member 7 which suppresses an increase in a length of the depth of the jack 10a and which does not cause a problem of adjustment of the optical axis.

(Structure of Field of View Restriction Member 7)

Figure 6:
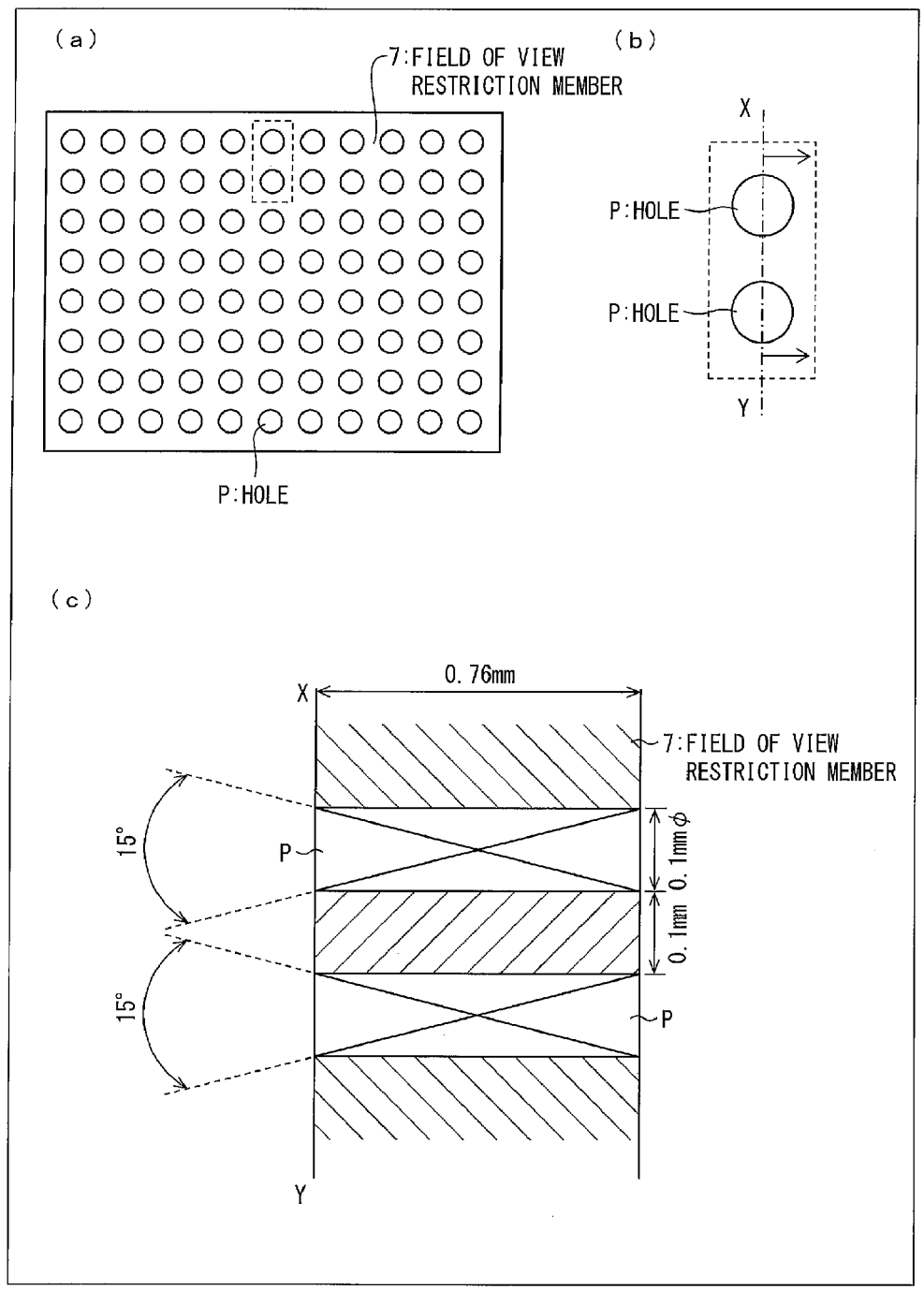
FIG. 6(a) is a view illustrating a part of an appearance structure of the field of view restriction member, (b) is a view which is further extraction of a part of the field of view restriction member illustrated in (a), and (c) is a sectional view when a section of the field of view restriction member taken along an XY axis illustrated in (b) is viewed from an arrow direction.

Next, an example of a structure of the field of view restriction member 7 provided in the jack 10a will be described by using FIG. 6. FIG. 6(a) is a view illustrating a part of an appearance structure of the field of view restriction member 7, FIG. 6(b) is a view which is further extraction of a part of the field of view restriction member 7 illustrated in FIG. 6(a), and FIG. 6(c) is a sectional view when a section of the field of view restriction member 7 taken along an XY axis illustrated in FIG. 6(b) is viewed from an arrow direction.

The field of view restriction member 7 is a plate-shaped member provided in the in-jack opening 8, and restricts an angle of infrared radiation passing through the field of view restriction member 7 to thereby restrict the FOV of the light reception unit 2. Differently from the window material 6 formed of a material which transmits infrared radiation, the field of view restriction member 7 is formed of a material which absorbs infrared radiation, and is provided with many minute holes P (through holes) as illustrated in FIGS. 6(a) and (b) by laser-beam machining or the like. Among infrared radiation which is transmitted through the window material 6, part of infrared radiation which has passed through the holes P is output toward the cavity of sealing resin 5 and reaches the light reception unit 2.

Though a polyimide plate material or the like, which has a property of absorbing infrared radiation, can be used for the field of view restriction member 7, this is merely an example, and any material which absorbs and does not transmit infrared radiation is able to be used as a material of the field of view restriction member 7. However, it is desirable to use a material which generates a small amount of heat when the field of view restriction member 7 absorbs infrared radiation. An Example thereof includes glass which has higher thermal conductivity than that of resin.

The FOV of the light reception unit 2 is restricted according to a ratio of a thickness of the field of view restriction member 7 and a diameter of the provided hole P (aspect ratio), and a relation of tan(FOV/2)=(the diameter of the hole P provided in the field of view restriction member 7)/(the thickness of the field of view restriction member 7) is established. Here, tan(FOV/2) is a tangent of an angle of (FOV/2). FIG. 6(c) illustrates an example of the field of view restriction member 7 which restricts a maximum incident angle of infrared radiation to 15° or less. In a case where the diameter of the hole P is 0.1 mm, and a shortest distance between adjacent holes P, that is, a pitch is 0.1 mm, it is found that the thickness of the field of view restriction member 7 needs to be about 0.76 mm or more.

That is, it is possible to express the field of view restriction member 7 included in the jack 10a in a following manner. It may be configured such that, when a maximum angle of an angle formed by a direction of infrared radiation which straightly advances from outside the insertion hole 15 and is then made incident on the light reception unit 2 and a normal line of a light reception surface of the light reception unit 2 is set as X° (in FIG. 6, X=7.5°), the field of view restriction member 7 is provided with the hole P which is almost parallel to the normal line of the light reception surface of the light reception unit 2, and a ratio of a width of the hole P (in FIG. 6, 0.1 mm) and a length of the hole P (in FIG. 6, 0.76 mm) in a section when the hole P is cut along a plane including the normal line is equal to or less than tan(X°).

In this manner, the jack 10a in one aspect includes the field of view restriction member 7 which is provided with many of the holes P each having almost the same aspect ratio and whose holes P respectively have the aspect ratio of tan(FOV/2). With such a configuration, infrared radiation whose angle difference from infrared radiation perpendicularly incident on the light reception unit 2 is equal to or more than FOV/2 is not able to pass through the holes P of the field of view restriction member 7 and does not reach the light reception unit 2. Thus, even when a plug such as the optical plug 20 is not inserted into the insertion hole 15 of the jack 10a, it is possible to restrict the FOV of the light reception unit 2. Accordingly, by turning the opening of the insertion hole 15 in a direction toward an object to be measured, it is possible to receive infrared radiation only from the object to be measured and measure temperature thereof.

Moreover, by providing the field of view restriction member 7, it is possible to suppress an increase in the length of the depth of the jack 10a compared to a case where the above-described silicon diffraction lens 70 is applied. Furthermore, by using the field of view restriction member 7 in which the holes P are provided so as to have shorter pitches therebetween, it is possible to reduce influence by relative positional shift of the field of view restriction member 7 and the light reception unit 2.

In addition, by increasing an aperture ratio of the field of view restriction member 7 to thereby make more infrared radiation emitted from an object to be measured incident on the light reception unit 2, it is possible to improve sensitivity and an S/N ratio. An aperture ratio in the field of view restriction member 7 which is provided with many holes P in circular shapes of the same size will be described by using FIG. 7. FIG. 7 is a view for explaining the aperture ratio of the field of view restriction member, in which (a) illustrates a state where the holes P are arrayed in parallel arrangement, and (b) illustrates a state where the holes P are arrayed in 45° staggered arrangement. In FIG. 7, the diameter of the holes P is d and the pitch is p. The aperture ratio (%) in the case of arraying the holes P in the parallel arrangement as illustrated in FIG. 7(a) is obtained as $78.5 \times d^2/p^2$, and in a case where p=0.1 mm and d=0.1 mm, the aperture ratio is calculated as about 19.6%. On the other hand, the aperture ratio (%) in the case of arraying the holes P in the 45° staggered arrangement as illustrated in FIG. 7(b) is obtained as $157 \times d^2/p^2$, and in a case where p=0.1 mm and d=0.1 mm, the aperture ratio is calculated as about 39.3%. Accordingly, it is found that, even when the diameter and the pitch of the holes P are same, the aperture ratio becomes about twice by arraying the holes P in the 45° staggered arrangement, compared with the case of the parallel arrangement. In this manner, in addition to increasing a size of the holes P or narrowing an interval between the holes P, it is possible to increase the aperture ratio of the field of view restriction member 7 by changing arrangement of the holes P.

[Embodiment 2]

Another embodiment of the invention will be described based on FIG. 8 to FIG. 10 as follows. Note that, for convenience of description, the same reference signs are assigned to members having the same functions as those of the members described in the aforementioned embodiment, and description thereof will be omitted.

An example of a structure of a jack (optical transmission device) 10b according to the present embodiment will be described below by using FIG. 8. FIG. 8 is a sectional view illustrating an example of the structure of the jack 10b including a first thermopile 1a and a second thermopile 1b. The jack 10b is different from the jack 10 illustrated in FIG. 1(a) in that a plurality of thermopiles are included.

The first thermopile 1a is provided with a light reception unit (first optical element) 2a and the second thermopile 1b is provided with a light reception unit (second optical element) 2b. The first thermopile 1a and the light reception unit 2a of the jack 10b are provided at almost the same positions as those of the thermopile 1 and the light reception unit 2 of the jacks 10 and 10a according to Embodiment 1 described above. Thus, when a plug such as the optical plug 20 is not inserted into the insertion hole 15 of the jack 10b, infrared radiation emitted from an object to be measured which exists outside the insertion hole 15 of the jack 10b and infrared radiation output from the surface of the side in which the insertion hole 15 of the holding body 9 is formed are made incident on the light reception unit 2a.

On the other hand, the second theimopile 1b and the light reception unit 2b are provided at positions which allow only infrared radiation output from an inner part of the jack 10b, that is, the surface of the side in which the insertion hole 15 of the holding body 9 is formed to be incident when a plug such as the optical plug 20 is not inserted into the insertion hole 15 of the jack 10b. For example, in a case where the jack 10b has the same depth and the same inner diameter as those of the jack 10a illustrated in FIG. 5, an FOV of the light reception unit 2b of the second thermopile 1b becomes about 63° as illustrated in FIG. 8.

By using radiant energy of infrared radiation incident on the light reception unit 2b to perform correction, it is possible to offset an amount of radiant energy of infrared radiation incident on the light reception unit 2a from the surface of the side in which the insertion hole 15 of the holding body 9 is formed to calculate radiant energy of infrared radiation incident on the light reception unit 2a from an object to be measured. This calibration process will be described in detail below.

(Calibration Process)

The calibration process that the radiant energy of the infrared radiation incident on the light reception unit 2a from the object to be measured is calculated by using the radiant energy of the infrared radiation incident on the light reception unit 2b of the second thermopile 1b will be described below by using FIG. 9 and FIG. 10. FIG. 9 is a view for explaining an example of the calibration process in the jack 10b including the second thermopile 1b illustrated in FIG. 8. FIG. 9 illustrates the calibration process for a case where any of temperature T4 and an emissivity α4 of the object to be measured and temperature T3 and an emissivity α3 of the surface of the side in which the insertion hole 15 of the holding body 9 in the jack 10b is formed are known.

Here, when radiant energy is represented as a function P(T) of temperature T, the radiant energy of the infrared radiation emitted from the object to be measured which has the temperature T4 and the emissivity α4 is P(T4)×α4. Similarly, the radiant energy of the infrared radiation emitted from the surface of the side in which the insertion hole 15 of the holding body 9 in the jack 10b is formed, which has the temperature T3 and the emissivity α3, is P(T3)×α3.

Since an FOV of the light reception unit 2a and the FOV of the light reception unit 2b are different, an amount of infrared radiation received by the light reception unit 2a and an amount of infrared radiation received by the light reception unit 2b are not the same. Then, when setting A and B as coefficients indicating correlation between the FOV of the light reception unit 2a and the FOV of the light reception unit 2b, the radiant energy of the infrared radiation from the surface of the side in which the insertion hole 15 of the holding body 9 in the jack 10b is formed, which is received by the light reception unit 2a of the first thermopile 1a, is P(T3)×α3×A. Similarly, the radiant energy of the infrared radiation from the surface of the side in which the insertion hole 15 of the holding body 9 in the jack 10b is formed, which is received by the light reception unit 2b of the second thermopile 1b, is P(T3)×α3×B.

Accordingly, radiant energy E1 which is received by the light reception unit 2a of the first thermopile 1a is P(T3)×α3×A +P(T4)×α4, and radiant energy E2 which is received by the light reception unit 2b of the second thermopile 1b is P(T3)×α3×B. Thus, it is found that A/B which is a ratio of A and B is able to be obtained by (E1−P(T4)×α4)/E2.

Figure 8:
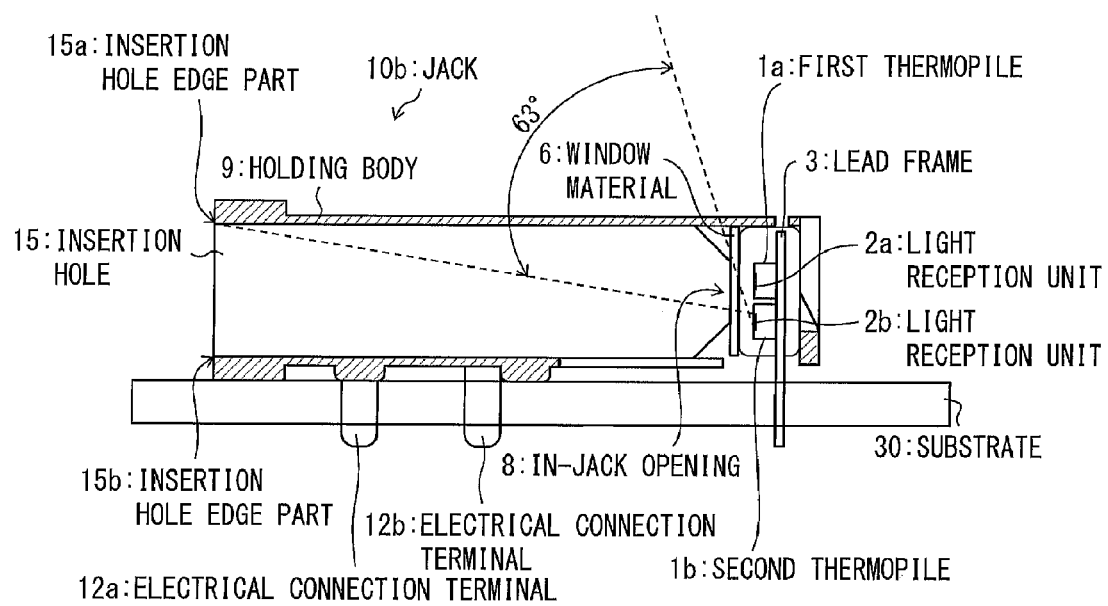
FIG. 8 is a sectional view illustrating an example of a structure of a jack including a first thermopile and a second thermopile according to Embodiment 2 of the invention.
Figure 10:
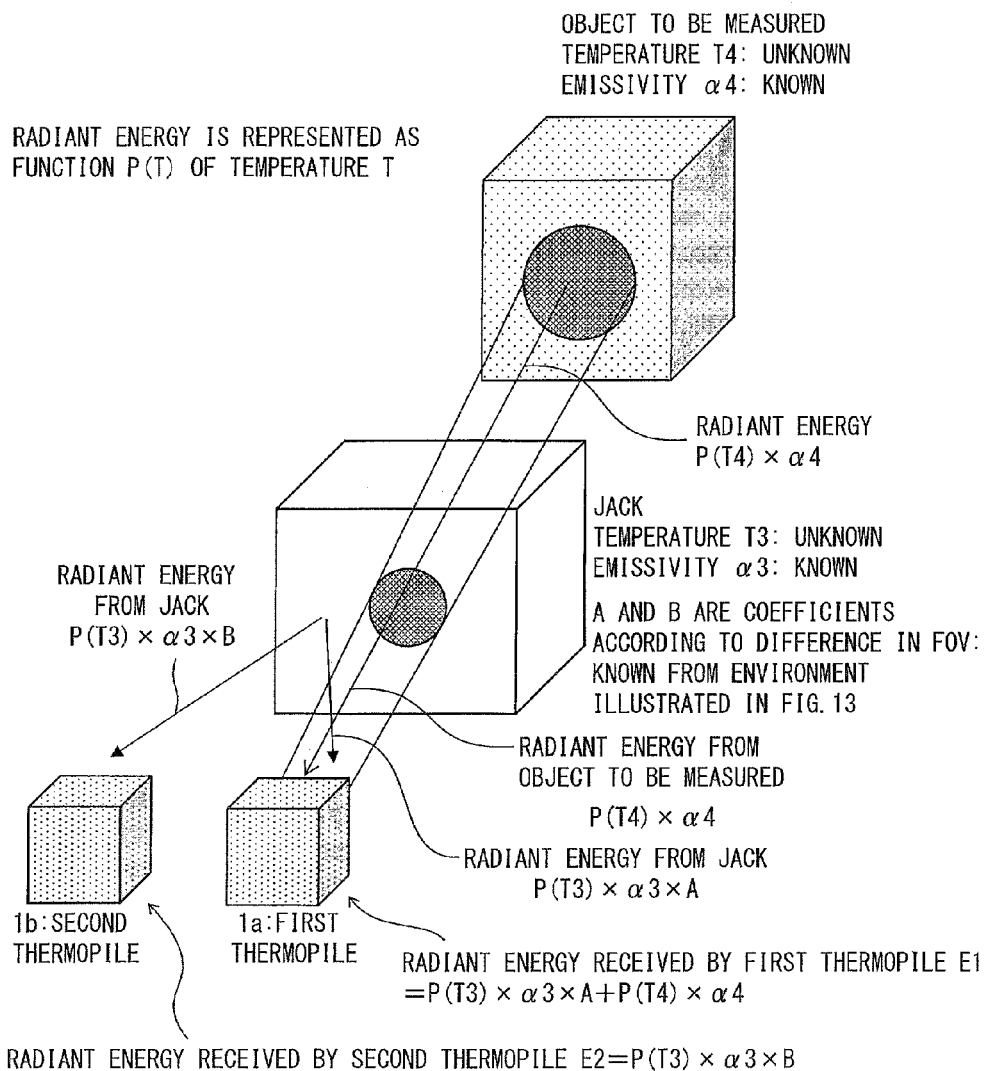
FIG. 10 is a view for explaining an example of measurement by using the jack including the second thermopile, which is illustrated in FIG. 8.

Next, FIG. 10 is a view for explaining an example of measurement by using the jack 10b including the second thermopile 1b illustrated in FIG. 8. FIG. 10 illustrates an example of measuring the temperature T4 for a case where both of the temperature T3 of the surface of the side in which the insertion hole 15 of the holding body 9 in the jack 10b is formed and the temperature T4 of the object to be measured are unknown and both of the emissivities of them are known.

Figure 9:
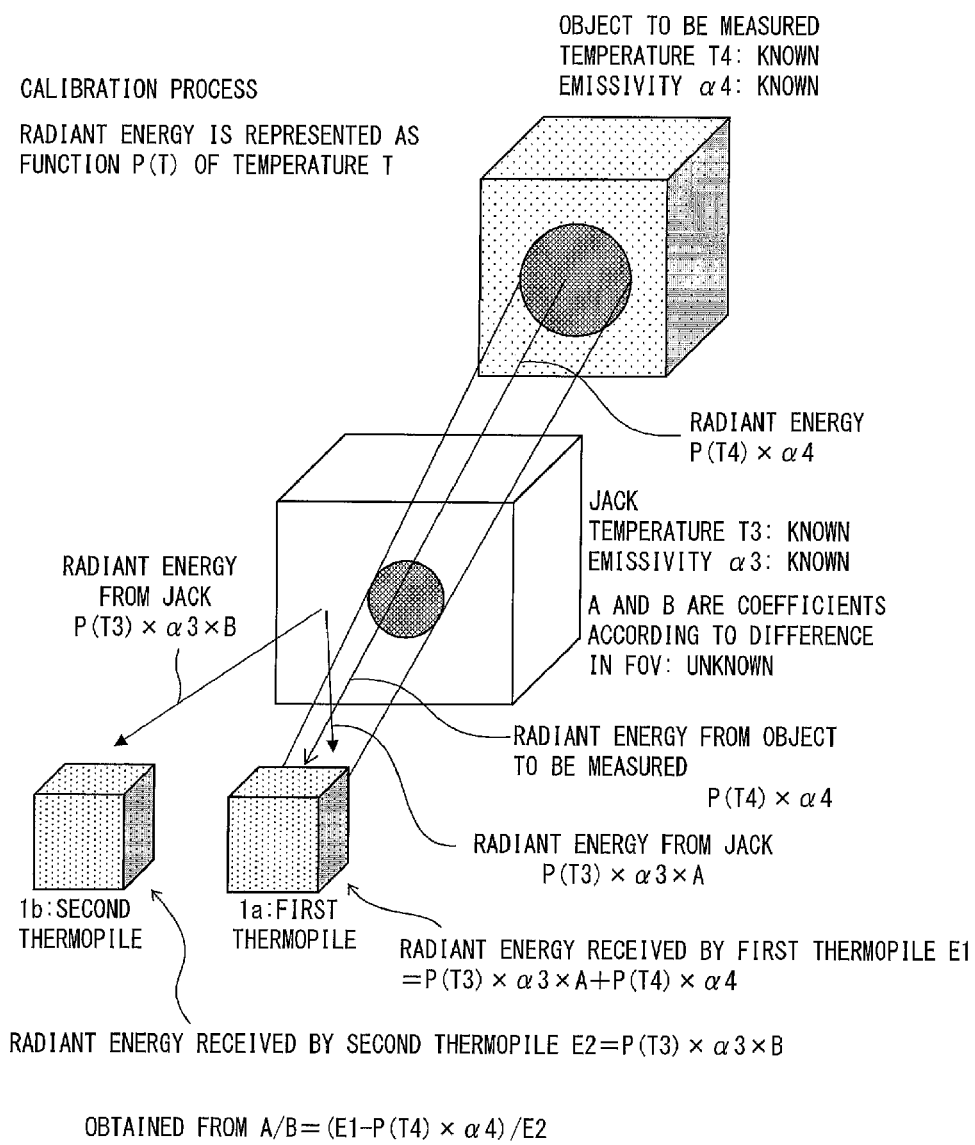
FIG. 9 is a view for explaining an example of a calibration process in the jack including the second thermopile, which is illustrated in FIG. 8.

Similarly to FIG. 9, the radiant energy of the infrared radiation emitted from the object to be measured, which has the temperature T4 and the emissivity α4, is P(T4)×α4. Similarly, the radiant energy of the infrared radiation emitted from the surface of the side in which the insertion hole 15 of the holding body 9 in the jack 10b is formed, which has the temperature T3 and the emissivity α3, is P(T3)×α3. In addition, the radiant energy of the infrared radiation from the surface of the side in which the insertion hole 15 of the holding body 9 in the jack 10b is formed, which is received by the light reception unit 2a of the first thermopile 1a, is P(T3)×α3×A. Similarly, the radiant energy of the infrared radiation from the surface of the side in which the insertion hole 15 of the holding body 9 in the jack 10b is formed, which is received by the light reception unit 2b of the second thermopile 1b, is P(T3)×α3×B. Accordingly, the radiant energy E1 which is received by the light reception unit 2a of the first thermopile 1a is P(T3)×α3×A+P(T4)×α4, and the radiant energy E2 which is received by the light reception unit 2b of the second thermopile 1b is P(T3)×α3×B. However, there is a difference from FIG. 9 in that the temperature T3 and the temperature T4 are unknown.

When subtracting E2×(A/B) from the radiant energy E1 which is received by the light reception unit 2a of the first thermopile 1a, a value of P(T4)×α4 is obtained as a following formula.

$$E1-E2\times(A/B)=\{P(T3)\times\alpha3\times A+P(T4)\times\alpha4\}-P(T3)\times\alpha3\times B\times(A/B)=P(T4)\times\alpha4$$

Since the emissivity α4 of the object to be measured is known, the temperature T4 is able to be calculated from the value of P(T4)×α4. Note that, a value of A/B is necessary in the above for obtaining P(T4)×α4, and this A/B is able to be obtained in advance by using the calibration process illustrated in FIG. 9. For example, after setting the temperature of the surface of the side in which the insertion hole 15 of the holding body 9 in the jack 10b is formed as a predetermined known temperature, infrared radiation from the object to be measured, whose temperature and emissivity are both known, is made incident on the light reception unit 2a. The value of A/B is obtained from the radiant energy E1 which is received by the light reception unit 2a of the first thermopile 1a, the radiant energy E2 which is received by the light reception unit 2b of the second thermopile 1b, and the radiant energy of the infrared radiation emitted from the object to be measured, which are obtained at this time.

Note that, described here is the example in which two thermopiles of the first thermopile 1a and the second thermopile 1b are included and the light reception unit 2b is provided at a position at which infrared radiation generated in accordance with temperature of an inner surface of the insertion hole 15 is detected more than by the light reception unit 2a, but it may be configured so that two independent light reception regions are provided on one thermopile and they function as the light reception unit 2a and the light reception unit 2b. Moreover, there is no limitation to the number of thermopiles, and it may be configured to include a third thermopile, a fourth thermopile, and the like.

[Embodiment 3]

Figure 11:
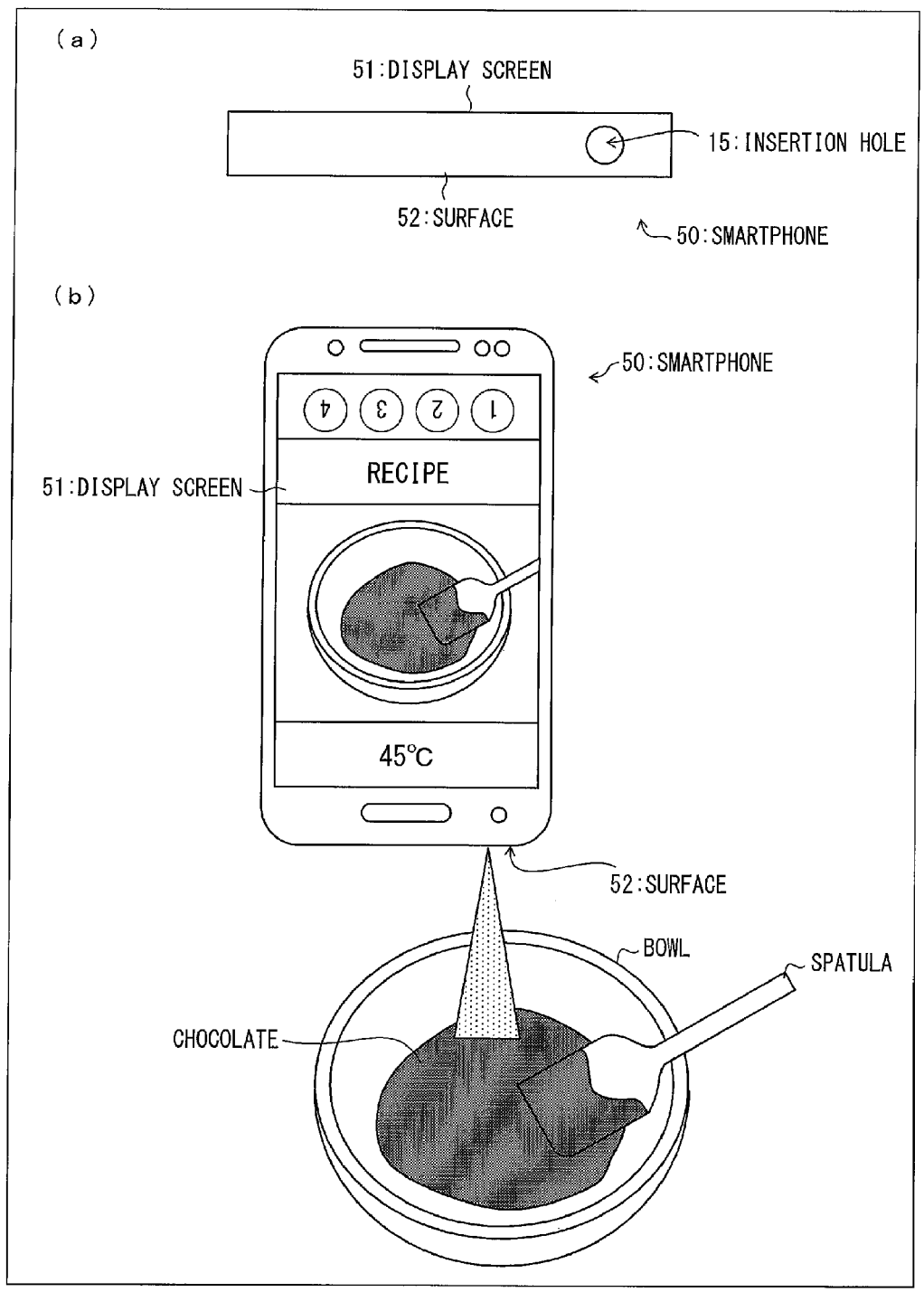
FIG. 11(a) is a view illustrating an example of a position of an insertion hole of a jack provided in a smartphone according to Embodiment 3 of the invention, and (b) is a view for explaining a state where temperature of an object to be measured is measured by turning the insertion hole illustrated in (a) toward the object to be measured.

Still another embodiment of the invention will be described based on FIG. 11 as follows. Described here is an example in which measurement of radiation temperature is performed in a non-contact manner by a smartphone (electronic apparatus) 50 which includes the jack 10a with no plug such as the optical plug 20 inserted into the insertion hole 15. FIG. 11 is a view illustrating an example of a position of the insertion hole 15 of the jack 10a provided in the smartphone 50, and (b) is a view for explaining a state where temperature of an object to be measured is measured by turning the insertion hole 15 illustrated in (a) toward the object to be measured. Note that, for convenience of description, the same reference signs are assigned to members having the same functions as those of the members described in the aforementioned embodiments, and description thereof will be omitted.

As illustrated in FIG. 11(a), in the jack 10a, the opening of the insertion hole 15 is provided in a surface 52 which is adjacent to a surface including a display screen 51 of the smartphone 50.

Description will be given here by taking an example of a case where chocolate warmed in a bowl placed in hot water is set as an object to be measured. First, the smartphone 50 executes an application for performing measurement of radiation temperature. Next, when a microprocessor incorporated in the smartphone 50 detects that no plug is inserted into the insertion hole 15 of the jack 10a, measurement of radiation temperature is started based on an amount of infrared radiation incident from the opening of the insertion hole 15. In this case, by considering that transmission loss due to transmission by the optical fiber 21 (refer to FIG. 3 and FIG. 4) is not generated in an amount of infrared radiation incident on the light reception unit 2, the radiation temperature of the object to be measured is calculated. Thus, it is possible to correctly measure the temperature of the object to be measured.

As illustrated in FIG. 11(*b*), other than a measurement result (45° C., here), display of information on a recipe or the like may be displayed on the display screen 51 at the same time.

Note that, the jack 10*a* includes the window material 6, so that it is possible to prevent, for example, steam from the object to be measured from intruding so far as the thermopile 1 or the light reception unit 2. As a result thereof, the radiation temperature is measured by turning the insertion hole 15 into which a plug such as the optical plug 20 is not inserted toward, for example, the object to be measured, which is cooked by heating.

In a case where an emissivity differs depending on a property of an object to be measured (for example, cooked food or the like), an error is caused in a measurement result of radiation temperature. The emissivity here is a ratio of an amount of infrared radiation generated at temperature of a black body to an amount of infrared radiation generated at temperature of a gray body. In such a case, it may be configured such that an emissivity of cooked food which corresponds to each recipe is held inside the smartphone 50 (for example, a storage unit) or on a cloud and the emissivity for each cooked food is able to be acquired as appropriate.

Note that, though the example in which the jack 10*a* is used is described here, the jack 10*b* is also applicable.

[Embodiment 4]

Figure 12:
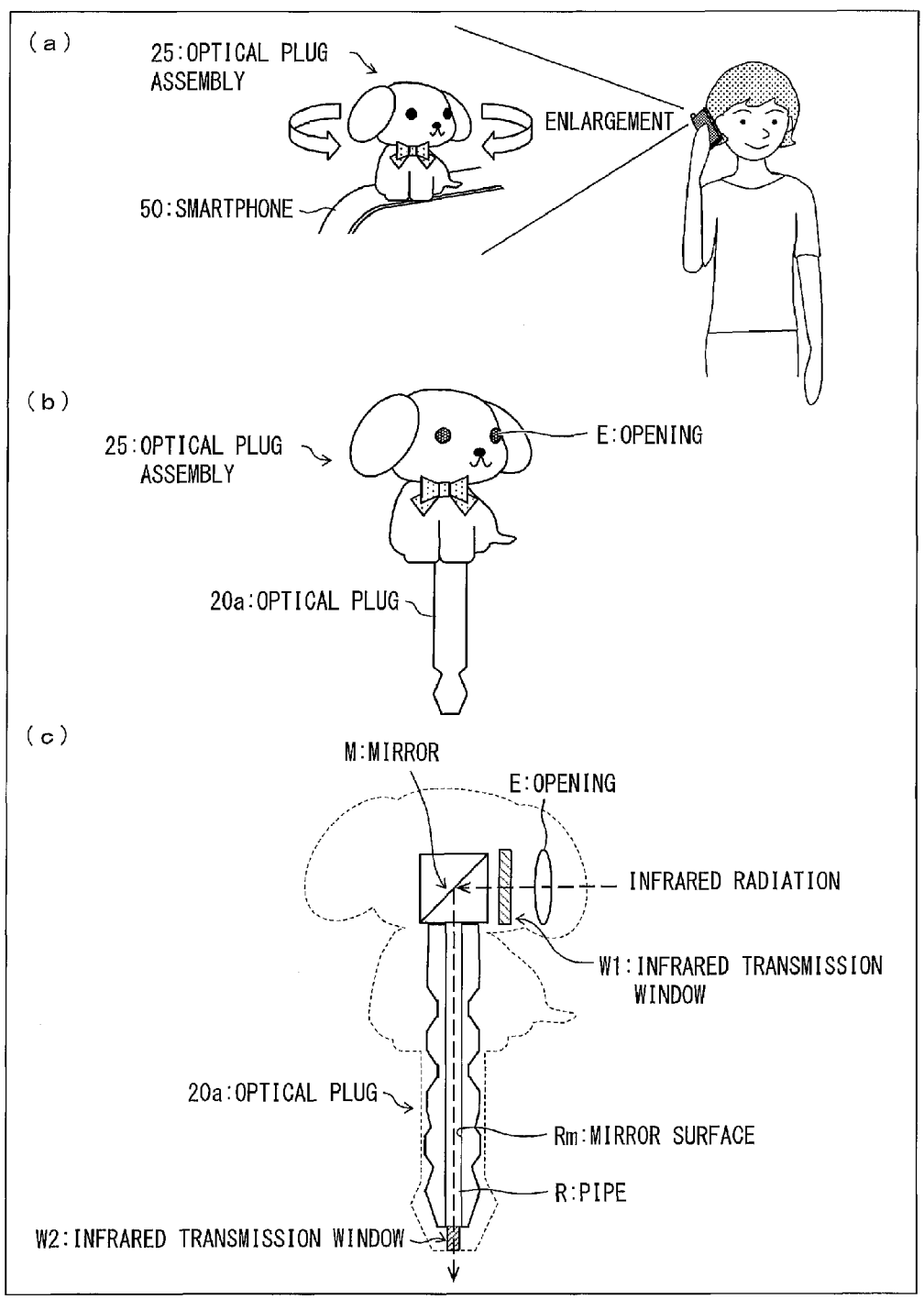
FIG. 12(a) is a view illustrating an appearance when an optical plug assembly which is used by being inserted into a jack according to Embodiment 4 of the invention is attached to a smartphone, (b) is a view illustrating an example of the appearance of the optical plug assembly illustrated in (a), and (c) is a schematic sectional view illustrating an inner structure of the optical plug assembly illustrated in (b).

Still another embodiment of the invention will be described based on FIG. 12 as follows. Described here is an example of an optical plug assembly 25 which is inserted into the insertion hole 15 of the jack 10 of the smartphone 50 to transmit infrared radiation to the light reception unit 2. FIG. 12(*a*) is a view illustrating an appearance when the optical plug assembly (light guide plug) 25 to be to be used being inserted into the jack 10 is attached to the smartphone 50, (*b*) is a view illustrating an example of the appearance of the optical plug assembly 25 illustrated in (*a*), and (*c*) is a schematic sectional view illustrating an inner structure of the optical plug assembly 25 illustrated in (*b*). Note that, for convenience of description, the same reference signs are assigned to members having the same functions as those of the members described in the aforementioned embodiments, and description thereof will be omitted.

FIG. 12(*a*) illustrates a state where the optical plug assembly 25 is inserted into the insertion hole 15 of the jack 10, which is provided in a surface adjacent to a surface including the display screen 51 of the smartphone 50 (for example, the surface 52 of FIG. 11(*a*)). In a case where a shape of the insertion hole 15 of the jack 10 is a tubular shape similarly to, for example, an earphone jack which has been distributed, the optical plug assembly 25 is 360° rotatable with the insertion hole 15 as a rotation axis.

As illustrated in FIG. 12(*b*), the optical plug assembly 25 is provided with an opening E, and causes a part of light entering the opening E from outside the optical plug assembly 25 to pass through an inner part of an optical plug 20*a* to guide to the light reception unit 2. The optical plug 20*a* has a shape which allows insertion into the insertion hole 15 of the jack 10, similarly to the optical plug 20 illustrated in the FIG. 3. An appearance shape of the optical plug assembly 25 is molded by using, for example, polyethylene resin. an example of the inner structure of the optical plug assembly 25 will be described below.

As illustrated in FIG. 12(*c*), the optical plug assembly 25 includes the opening E, an infrared transmission window W1, a mirror M (optical system), the optical plug 20*a*, a pipe R whose inner surface is a mirror surface Rm, and an infrared transmission window W2. Note that, though indicated here is an example in which a shape of a mascot of a dog is applied to the optical plug assembly 25, any design involving the inner structure illustrated in FIG. 12(*c*) is applicable.

The infrared transmission windows W1 and W2 are formed by using, for example, polyethylene or the like, but the material only needs to transmit infrared radiation, and there is no particular limitation. Moreover, the window material 6 may be provided in the opening E of the optical plug assembly 25 in order to prevent intrusion of moisture or the like.

The mirror M is an optical system member which includes a mirror surface provided in order to change an advancing direction of light incident from the opening E toward an inner side of the pipe R. Illustrated here is the example of the optical plug assembly 25 which uses one mirror M, but any number of mirrors M may be used for the configuration, in accordance with a relation of an incident angle of light from the opening E and an extending direction of the pipe R. In addition, a shape of the mirror M is not limited to that of a plane mirror, any optical system such as a concave mirror, a convex mirror, a light scattering mirror, or a light refraction surface may be used.

Infrared radiation entering the opening E of the optical plug assembly 25 (dashed line) is transmitted through the infrared transmission window W1 and is made incident on the mirror M. The mirror M causes the infrared radiation incident thereon to pass through inside the pipe R, which extends in the inner part of the optical plug 20*a*, to reach the infrared transmission window W2, and to be emitted from the optical plug 20*a*. In a case where the optical plug assembly 25 is inserted into the jack 10, the infrared transmission window W2 is proximate to or abuts the window material 6 of the jack 10 similarly to the optical fiber end part 22 of FIG. 3. A part of infrared radiation which has been emitted from the optical plug 20*a* and is transmitted through the window material 6 of the jack 10 is made incident on the light reception unit 2. In this manner, the optical plug assembly 25 guides infrared radiation incident from the opening E to the light reception unit 2 of the jack 10.

For example, in the case of measuring radiation temperature of an object to be measured by using the smartphone 50 to which the optical plug assembly 25 is attached, first, the smartphone 50 executes an application for performing measurement of radiation temperature. Next, when a microprocessor incorporated in the smartphone 50 detects that the optical plug assembly 25 is inserted into the insertion hole 15 of the jack 10, measurement of the radiation temperature is started based on an amount of infrared radiation incident from the opening E of the optical plug assembly 25. Note that, in this case, by considering that light guide loss due to light guide by the optical plug assembly 25 is generated in an amount of infrared radiation incident on the light reception unit 2, the radiation temperature of the object to be measured is calculated. Thus, it is possible to correctly measure the temperature of the object to be measured.

Further, for example, in a case where a user of the smartphone 50 speaks with the smartphone 50 to which the optical plug assembly 25 is attached put on his/her ear, when an orientation of the opening E of the optical plug assembly 25 is turned toward a head side of the user, infrared radiation due to body temperature of the user is made incident from the opening E. It is also possible to cause the jack 10 into which the optical plug assembly 25 is inserted to function as a proximity sensor or a human detection sensor based on a change in an amount of the infrared radiation.

Note that, though indicated here is the example of guiding infrared radiation, which has passed through the mirror surface Rm in a cylindrical shape inside the pipe R, almost perpendicularly to the light reception unit 2, there is no limitation thereto, and infrared radiation guided to the light reception unit 2 may be guided so as to be incident at an angle which is not perpendicular. However, by configuring the pipe R in a cylindrical shape so as to have a short length and causing infrared radiation which is to be incident on a light reception surface to be in a direction almost perpendicular to the light reception surface of the light reception unit 2, it is possible to reduce light guide loss of the infrared radiation.

Note that, though description has been made here for a case where the optical plug assembly 25 is inserted into the jack 10, the optical plug assembly 25 is applicable also to the jacks 10*a* and 10*b*.

[Embodiment 5]

Figure 13:
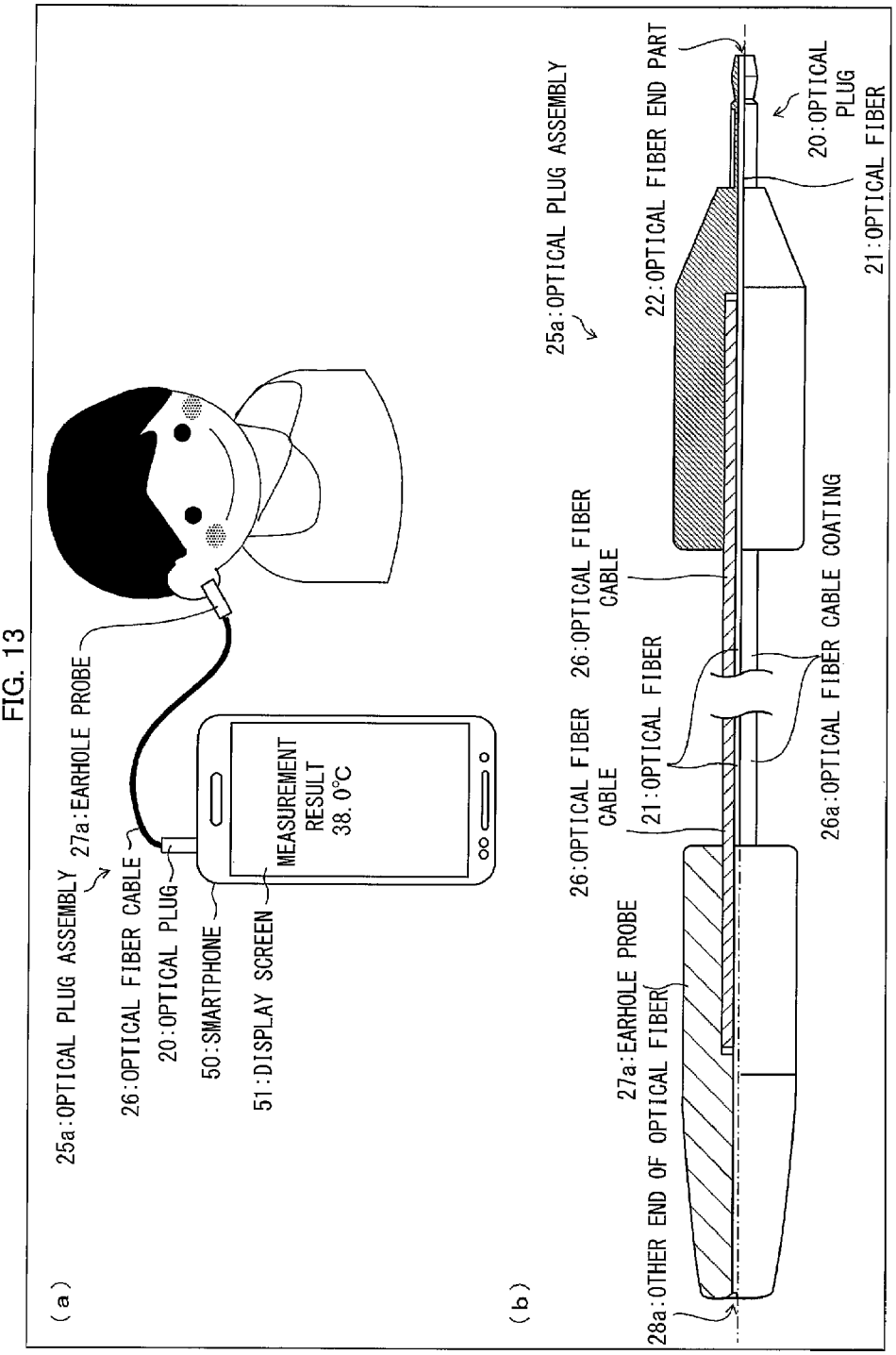
FIG. 13(a) is a view illustrating an example of an optical plug assembly in a case where a smartphone having a jack into which an optical plug to which an earhole probe according to Embodiment 5 of the invention is coupled with an optical fiber cable is inserted is used as an ear thermometer, and (b) is a partial sectional view illustrating an example of a schematic structure of the optical plug assembly illustrated in (a).

Still another embodiment of the invention will be described based on FIG. 13 as follows. Described here is an optical plug assembly (optical fiber plug) 25*a* that the optical plug (optical fiber plug) 20 to be inserted into the insertion hole 15 of the jack 10 of the smartphone 50 and an earhole probe 27*a* are coupled with an optical fiber cable 26. FIG. 13(*a*) is a view illustrating an example of the optical plug assembly 25*a* in a case where the smartphone 50 which has the jack 10 into which the optical plug 20 to which the earhole probe 27*a* is coupled with the optical fiber cable 26 is inserted is used as an ear thermometer, and (*b*) is a partial sectional view illustrating an example of a schematic structure of the optical plug assembly 25*a* illustrated in (*a*). Note that, for convenience of description, the same reference signs are assigned to members having the same functions as those of the members described in the aforementioned embodiments, and description thereof will be omitted.

The earhole probe 27*a* is resin-molded, and the optical fiber 21 is arranged inside the earhole probe 27*a*. Note that, there is no particular limitation to a shape of the earhole probe 27*a* as long as being a shape which does not damage an eardrum of a subject.

The optical fiber cable 26 is obtained by coating the optical fiber 21 with an optical fiber cable coating 26*a*, and can be formed in any length and thickness.

Figure 14:
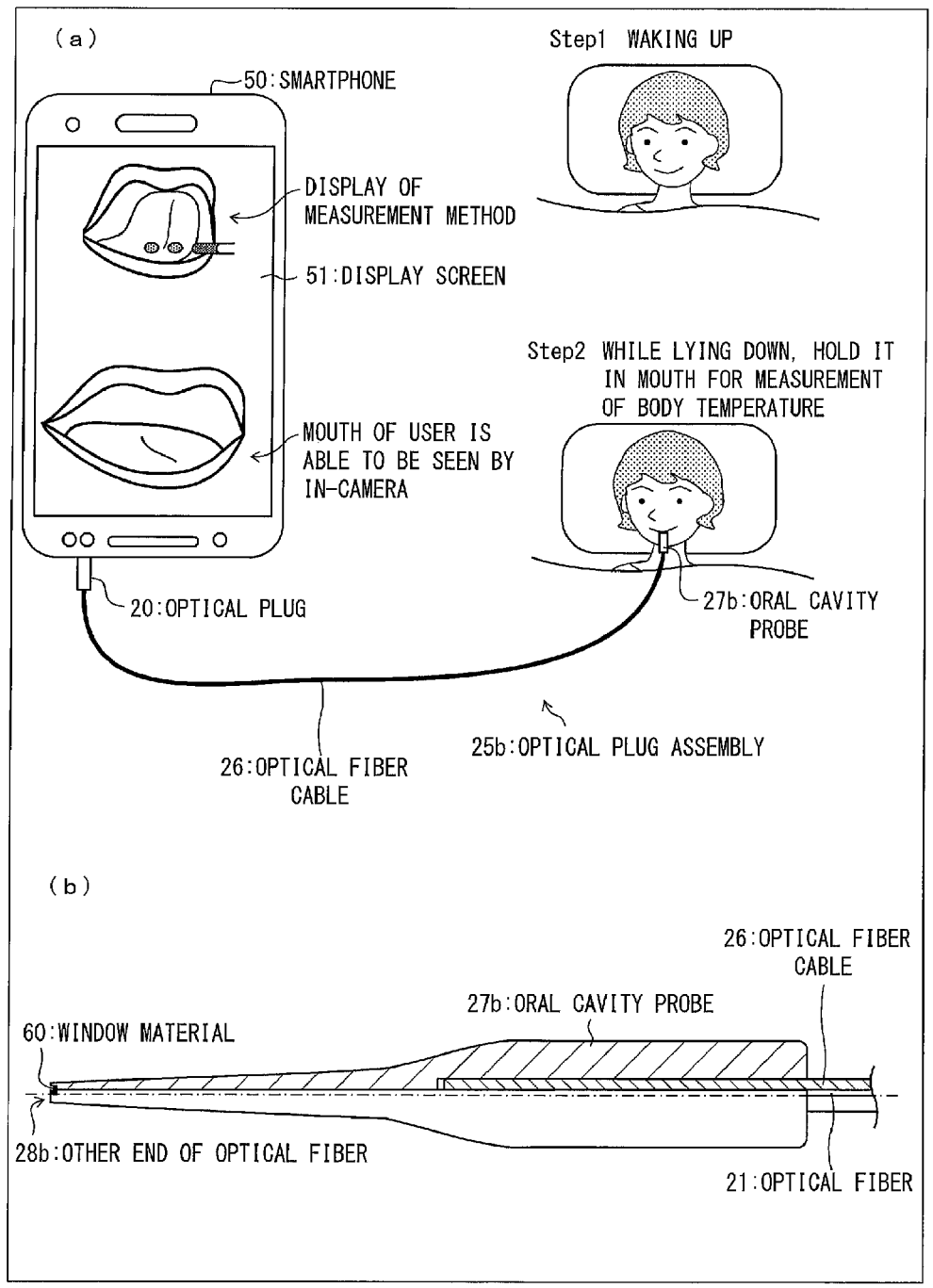
FIG. 14(a) is a view illustrating an example of an optical plug assembly in a case where a smartphone having a jack into which an optical plug to which an oral cavity probe according to Embodiment 6 of the invention is coupled with an optical fiber cable is inserted is used as a basal thermometer, and (b) is a partial sectional view illustrating an example of a schematic structure of the optical plug assembly illustrated in (a).

For example, in the case of measuring body temperature of a subject by using the smartphone 50 to which the optical plug assembly 25*a* is attached, first, as illustrated in FIG. 14(*a*), the subject inserts the earhole probe 27*a* into his/her earhole so that the other end of the optical fiber (light collecting unit) 28*a* is inserted into inside the earhole, and, on the other hand, inserts the optical plug 20 into the insertion hole 15 of the jack 10 provided in the smartphone 50. Next, an application for causing the smartphone 50 to function as an ear thermometer is executed. When a microprocessor incorporated in the smartphone 50 detects that the optical plug assembly 25*a* is inserted into the insertion hole 15 of the jack 10, the measurement of the body temperature inside the earhole is started based on an amount of infrared radiation incident from the other end of the optical fiber 28*a* of the earhole probe 27*a* of the optical plug assembly 25*a*. Note that, in this case, by considering, for the amount of the infrared radiation incident on the light reception unit 2, a shape of the other end of the optical fiber 28*a* of the earhole probe 27*a* and transmission loss due to transmission by the optical fiber cable 26, the body temperature of the subject is calculated. Thereby, the body temperature of the subject is able to be correctly measured.

Note that, by using the optical plug assembly 25*a*, the display screen 51 of the smartphone 50 may display body temperature of the subject, which has been measured before, medical history, a type of disease which is assumed from transition of the measured body temperature, or the like, with the execution of the application for measuring body temperature. Moreover, results of measurement of body temperature or medical history of a plurality of subjects may be displayed. Furthermore, an application for enabling acquisition of appropriate advice from a doctor by sending data of measured body temperature to the doctor, or a health service on a cloud may be operated together.

[Embodiment 6]

Still another embodiment of the invention will be described based on FIG. 14 as follows. Described here is an optical plug assembly (optical fiber plug) 25*b* that the optical plug (optical fiber plug) 20 to be inserted into the insertion hole 15 of the jack 10 of the smartphone 50 and an oral cavity probe 27*b* are coupled with the optical fiber cable 26. FIG. 14(*a*) is a view illustrating an example of the optical plug assembly 25*b* in a case where the smartphone 50 which has the jack 10 into which the optical plug 20 to which the oral cavity probe 27*b* is coupled with the optical fiber cable 26 is inserted is used as a basal thermometer, and (*b*) is a partial sectional view illustrating an example of a schematic structure of the optical plug assembly 25*b* illustrated in (*a*). Note that, for convenience of description, the same reference signs are assigned to members having the same functions as those of the members described in the aforementioned embodiments, and description thereof will be omitted.

The oral cavity probe 27*b* is resin-molded, and the optical fiber cable 26 is arranged inside the oral cavity probe 27*b*. Note that, there is no particular limitation to a shape of the oral cavity probe 27*b*. However, the oral cavity probe 27*b* is a member held in a mouth by a subject, so that it is desirable to satisfy safety standard applied to toys for children or pacifiers for infants. For example, the other end of the optical fiber 28*b* of the oral cavity probe 27*b* is not exposed in a surface of the oral cavity probe 27*b*, and has a window material 60, which prevents intrusion of saliva or the like and has a property of transmitting light having a wavelength of 6 to 15 μm, provided outside thereof.

For example, in the case of measuring basal body temperature of a subject by using the smartphone 50 to which the optical plug assembly 25*b* is attached, first, as illustrated in FIG. 14(*a*), the subject holds the oral cavity prove 27*b* in her mouth so that the other end of the optical fiber (light collecting unit) 28*b* exists in her oral cavity, at a time of waking up, while keeping resting posture of lying down. On the other hand, the optical plug 20 is inserted into the insertion hole 15 of the jack 10 provided in the smartphone 50. Next, an application for causing the smartphone 50 to function as a basal thermometer is executed. When a microprocessor incorporated in the smartphone 50 detects that the optical plug assembly 25*b* is inserted into the insertion hole 15 of the jack 10, the measurement of the body temperature inside the oral cavity is started based on an amount of infrared radiation incident from the other end of the optical fiber 28*b* of the oral cavity probe 27*b* of the optical plug assembly 25*b*. Note that, in this case, by considering, for the amount of the infrared radiation incident on the light reception unit 2, a shape of the other end of the optical fiber 28*b* of the oral cavity probe 27*b*, transmittance of the window material 60, and transmission loss due to transmission by the optical fiber cable 26, the basal body temperature of the subject is calculated. Thereby, the basal body temperature of the subject is able to be correctly measured.

An image of an inside of the oral cavity by an image sensor may be displayed on the display screen 51 on a real-time basis in order for the subject to refer to the image. The subject checks the image of the inside of the oral cavity, so that the subject is able to hold the oral cavity probe 27b in her mouth so as to be at almost the same position at every measurement. Thereby, it is possible to prevent occurrence of an error caused by positions of the other end of the optical fiber 28b when the oral cavity probe 27b is held in her mouth, which become different according to each measurement of basal body temperature.

Moreover, on the display screen 51 of the smartphone 50, a graph indicating changes of the basal body temperature of the subject, which is measured by using the optical plug assembly 25b, an estimated ovulation day estimated based on transition of the basal body temperature, or the like may be displayed.

[Embodiment 7]

Figure 15:
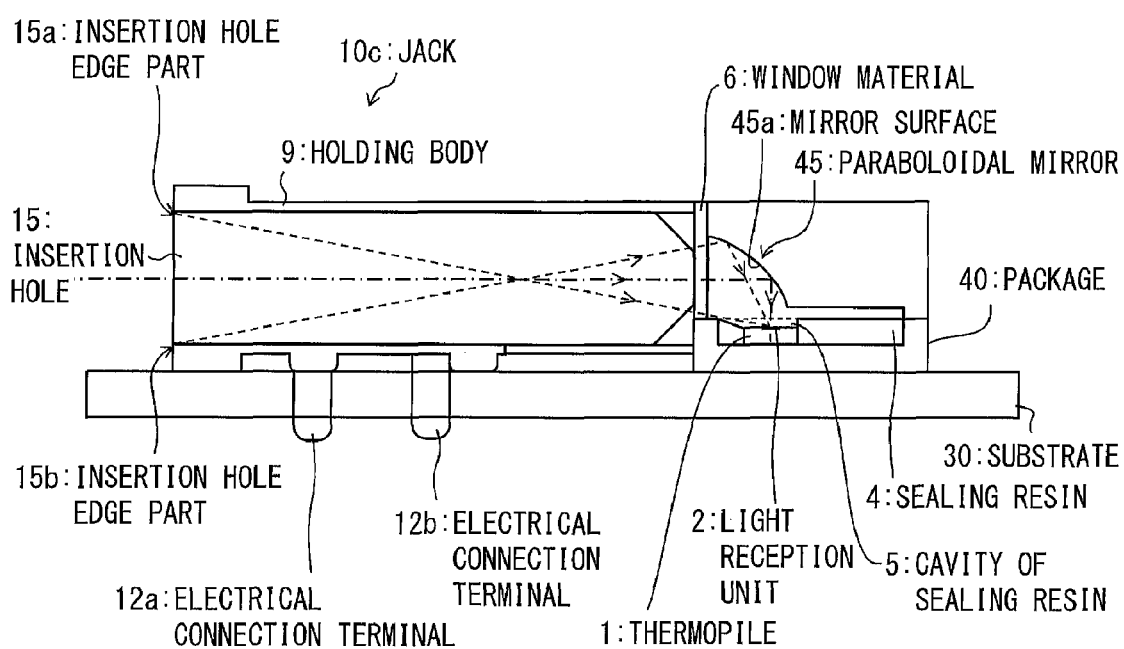
FIG. 15 is a sectional view illustrating an example of a schematic structure of a jack according to Embodiment 7 of the invention, which includes a paraboloidal mirror surface making infrared radiation incident on a light reception unit.

Still another embodiment of the invention will be described based on FIG. 15 as follows. FIG. 15 is a sectional view illustrating an example of a schematic structure of a jack which includes a reflection surface making infrared radiation incident on the light reception unit 2. Note that, for convenience of description, the same reference signs are assigned to members having the same functions as those of the members described in the aforementioned embodiments, and description thereof will be omitted.

In a package 40 of a jack (optical transmission device) 10c, the thermopile 1 including the light reception unit 2 which detects infrared radiation of 1 to 15 μm is fixed to a predetermined position, and the thermopile and the package 40 are electrically connected with a wire which is not illustrated. The package 40 is fixed to the substrate 30 and electrically connected to an electronic circuit of an electronic apparatus or a smartphone.

In the jack 10c (optical transmission device) of FIG. 15, a part of infrared radiation which is transmitted through the window material 6 is reflected by a mirror surface 45a provided in a paraboloidal mirror 45 and made incident on the light reception unit 2. In a case where a depth of an insertion hole of the jack 10c may be deep compared to that of the jacks 10 and 10a and the like, a structure of the jack 10c can be also applied.

[Embodiment 8]

An embodiment of the invention will be described in detail based on FIG. 16 to FIG. 24 and FIG. 34. Here, a light reception device according to the invention will be described by taking an example of an electrical jack (light reception device) 10' which is composed by using a basic structure of an earphone jack. Into the electrical jack 10', a small-sized single-head electrical plug used for electric transmission, which is generally mounted on, for example, a portable terminal or a smartphone (portable apparatus), is inserted. That is, the electrical jack 10' is an earphone jack which is able to be used with the aforementioned electrical plug inserted therein. The electrical jack 10' includes an optical element which detects infrared radiation. The light reception device according to the present embodiment is realized as the electrical jack 10'.

(Schematic configuration of electrical jack 10')

Figure 16:
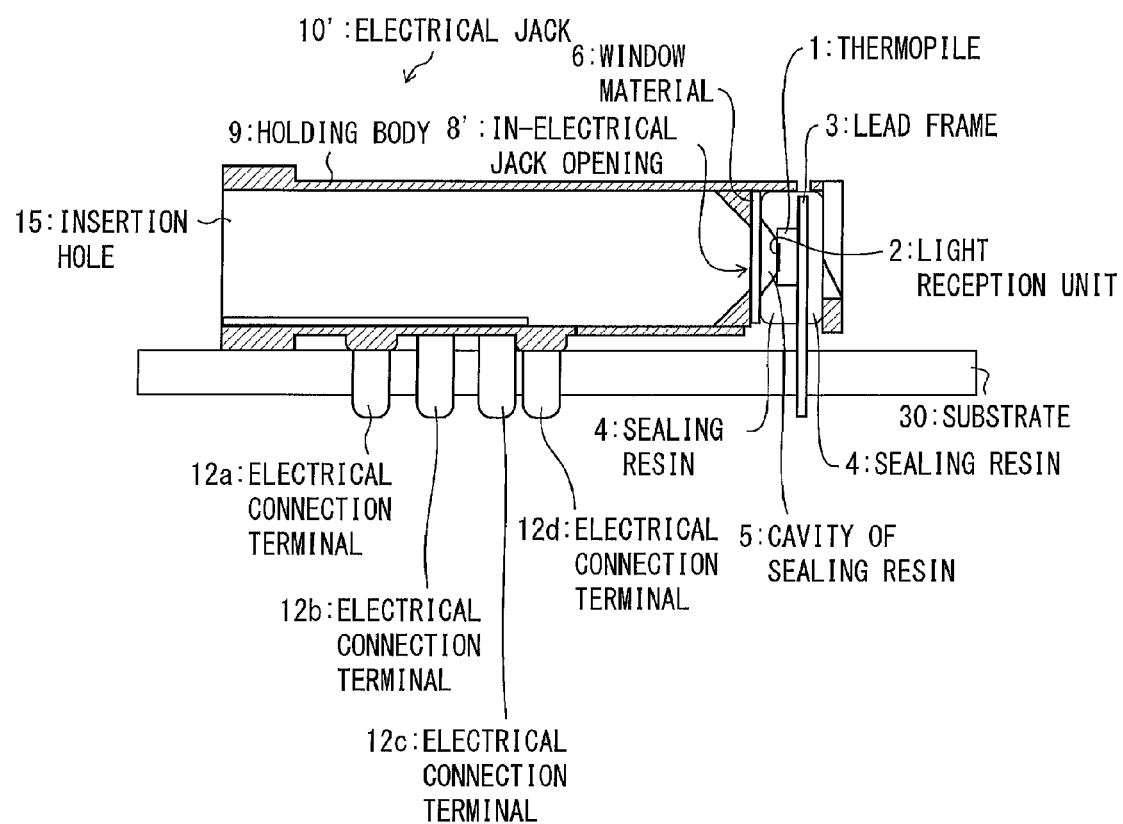
FIG. 16 is a sectional view illustrating an example of a structure of an electrical jack according to Embodiment 8 of the invention.

In an embodiment of the invention, the electrical jack 10' is a jack dedicated to electric transmission, which is provided in a portable terminal, a smartphone, or the like, as described above. FIG. 16 is a sectional view illustrating an example of a structure of the electrical jack 10' according to Embodiment 8 of the invention.

The electrical jack 10' includes the window material 6, an in-electrical jack opening 8', the holding body 9, electrical connection terminals 12a, 12b, 12c, and 12d, and the insertion hole 15. The electrical jack 10' further includes the thermopile 1 (infrared sensor), the light reception unit 2, the lead frame 3, the sealing resin 4, and the cavity of sealing resin 5. The electrical jack 10' is fixed to the substrate 30 which is provided in an inner part of a portable terminal, a smartphone, or the like. That is, the electrical jack 10' has an electric transmission function when an electrical plug is connected (inserted), and has a function of receiving infrared radiation by the thermopile 1 in a state where the electrical plug is not connected (inserted).

Here, the holding body 9 and the insertion hole 15 will be described briefly. Note that, the window material 6, the in-electrical jack opening 8', the thermopile 1, the light reception unit 2, the lead frame 3, the sealing resin 4, and the cavity 5 of sealing resin 4 will be described below by using FIGS. 17(a) and (b).

The holding body 9 is a substantially tubular member molded by using non-transparent resin. The thermopile 1 (infrared sensor), the light reception unit 2, the lead frame 3, and the sealing resin 4 are fixed to and stored in the holding body 9 by using adhesive resin (not illustrated). Four conductive members (not illustrated) which make contact with and are electrically connected to an outer peripheral surface of an electrical plug to be inserted are provided in an inner peripheral surface of the insertion hole 15 of the holding body 9, and the conductive members are connected to each of the electrical connection terminals 12a to 12d so as to allow electric transmission.

The insertion hole 15 is a space into which the aforementioned electrical plug which is compatible with the electrical jack 10' is inserted. A distance from one end in an entrance side of the insertion hole 15 of the electrical jack 10' to the surface of the window material 6, which is in a side of the insertion hole 15, only needs to be a value exceeding 14.6 mm. Thereby, even when an insertion part (of 13.4 mm or more and 14.6 mm or less) of a general commercial electrical plug is inserted into the insertion hole 15, it is possible to prevent a tip end of the electrical plug from abutting and damaging the window material 6.

A length of an insertion part of a general commercial optical plug is 14.7 mm or more and 15 mm or less. A general depth of an insertion hole of an electrical jack (corresponding to the distance from the one end in the entrance side of the insertion hole 15 to the surface of the window material 6, which is in the side of the insertion hole 15) is not specified. A depth of the insertion hole 15 of the electrical jack 10' according to the present embodiment is set to be shorter than the aforementioned length of the insertion part of the optical plug.

Note that, by setting the depth of the insertion hole 15 of the electrical jack 10' to be longer than the length of the insertion part of the optical plug, it is possible to avoid that the tip end of the insertion part of the optical plug abuts and damages the window material 6 when the optical plug is erroneously inserted into the electrical jack 10' or when the optical plug is inserted into the electrical jack 10' which is an optical and electric shared jack which is compatible also with the optical plug.

(Schematic Configuration Around Light Reception Unit 2 of Electrical Jack 10')

Figure 17:
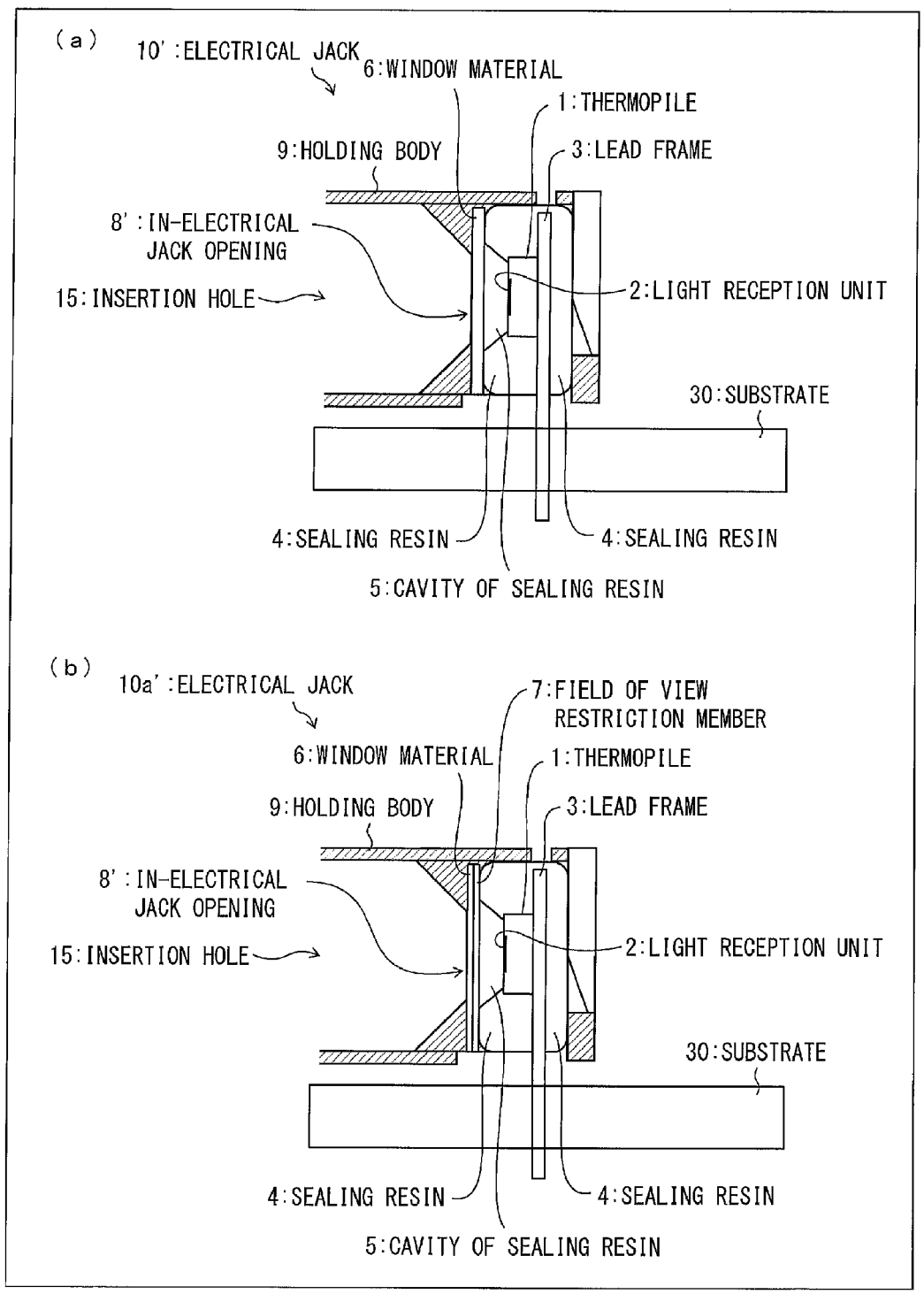
FIG. 17(a) is a sectional view illustrating a structure around an in-electrical jack opening of the electrical jack of FIG. 16, and (b) is a sectional view illustrating a structure in a case where the field of view restriction member is arranged in a vicinity of a window material of the electrical jack of FIG. 16.

Next, a structure of a vicinity of the light reception unit 2 of the electrical jack 10' will be described by using FIG. 17(*a*). FIG. 17(*a*) is a sectional view illustrating a structure around an in-electrical jack opening 8' of the electrical jack 10' of FIG. 16.

The window material 6 is a member for dustproofing and waterproofing, which is provided in order to prevent dust and moisture such as vapor intruding from the entrance side of the insertion hole 15 of the electrical jack 10' from directly abutting the thermopile 1 and the light reception unit 2. Further, the window material 6 has transmissivity which allows infrared radiation having a wavelength of 1 to 15 μm to be transmitted therethrough, and more preferably has transmissivity which allows infrared radiation having a wavelength of 6 to 15 μm to be transmitted therethrough. Zinc selenide (ZnSe) having toxicity, calcium fluoride (CaF) having deliquescency, or the like makes the window material 6 look transparent with visible light, but is not suitable therefor. As the window material 6, one obtained by molding, for example, high density polyethylene, silicon, germanium, or the like can be applied. Because of being provided deep in (at a bottom of) the insertion hole 15 of the electrical jack 10', the window material 6 is not exposed in a front surface of a housing of the portable terminal or the smartphone (portable apparatus), which includes the electrical jack 10'. Accordingly, a color, design, or beauty of an appearance of the front surface of the housing of the portable terminal or the smartphone (portable apparatus) is not affected. Thus, it is possible to use any material, which has the dustproof property, waterproof property and optical transmissivity, which are described above, as the window material 6.

Figure 18:
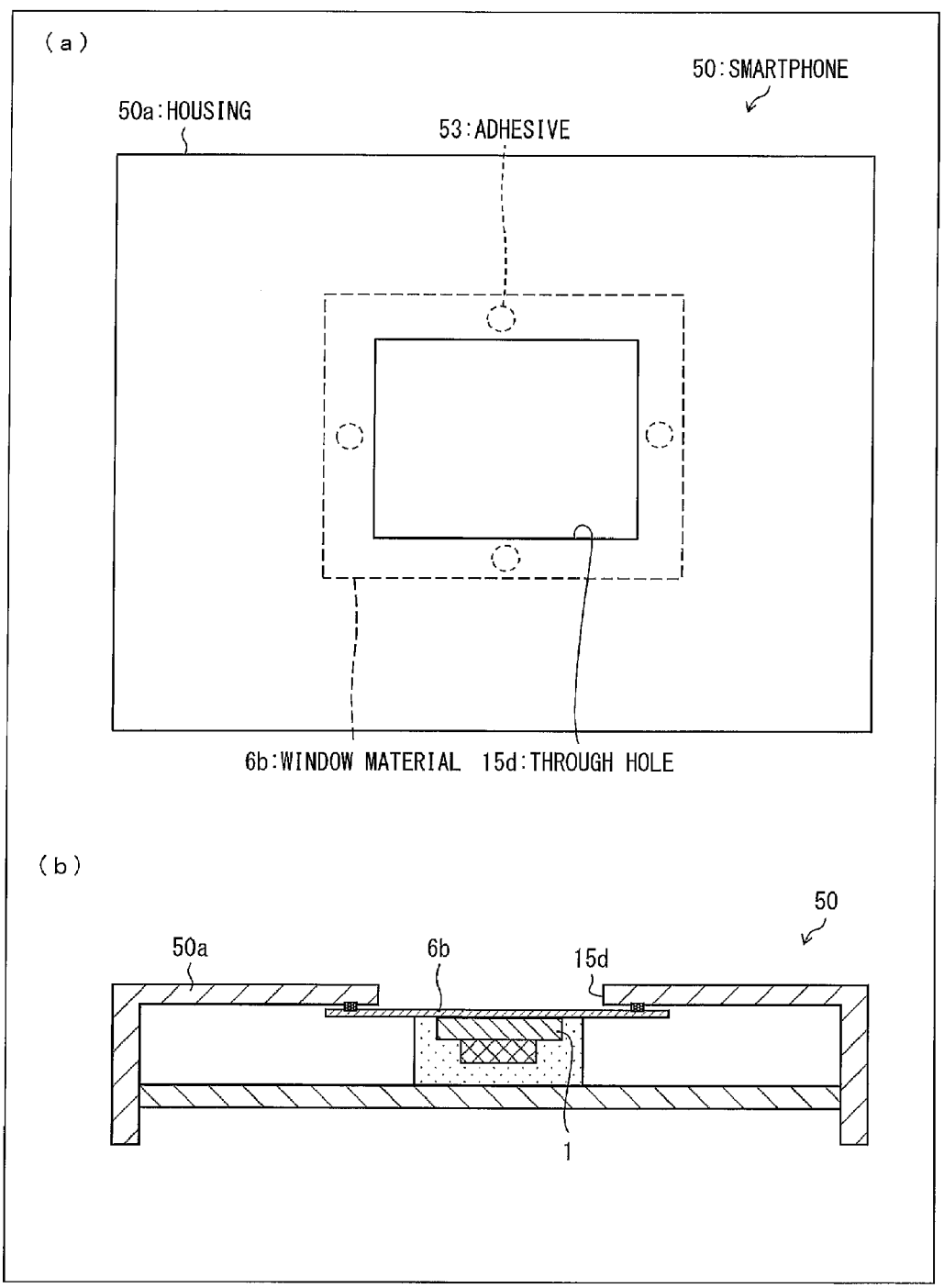
FIG. 18(a) is a plan view for explaining a non-waterproof adhesion structure of a window material provided in a smartphone according to Embodiment 8, and (b) is a sectional view thereof.

FIG. 18(*a*) is a plan view for explaining a non-waterproof adhesion structure of a window material 6*b* provided in the smartphone 50 according to Embodiment 8, and FIG. 18(*b*) is a sectional view thereof.

Referring to FIGS. 18(*a*) and (*b*), the smartphone 50 includes a housing 50*a* having a plate shape. In a surface of the housing 50*a*, a through hole 15*d* (concave part) having a rectangular shape is formed. The window material 6*b* having a rectangular shape, which is arranged at a bottom side of the through hole 15*d* and which transmits infrared radiation passing through the through hole 15*d*, is provided so as to cover the through hole 15*d*. The thermopile 1 which detects infrared radiation which is transmitted through the window material 6*b* is arranged in an inner side of the housing 50*a*.

The window material 6*b* is adhered to an inner surface of the housing 50*a* with an adhesive 53 applied to each center of four sides of a surface thereof. Though FIG. 18(*a*) illustrates a condition where the window material 6*b* and the housing 50*a* of the smartphone 50 are adhered to each other at four places, there is no limitation thereto as long as a dustproof property is realized, and needless to say, any of adhesion at six places, adhesion at three places, and adhesion at two places is possible.

Figure 19:
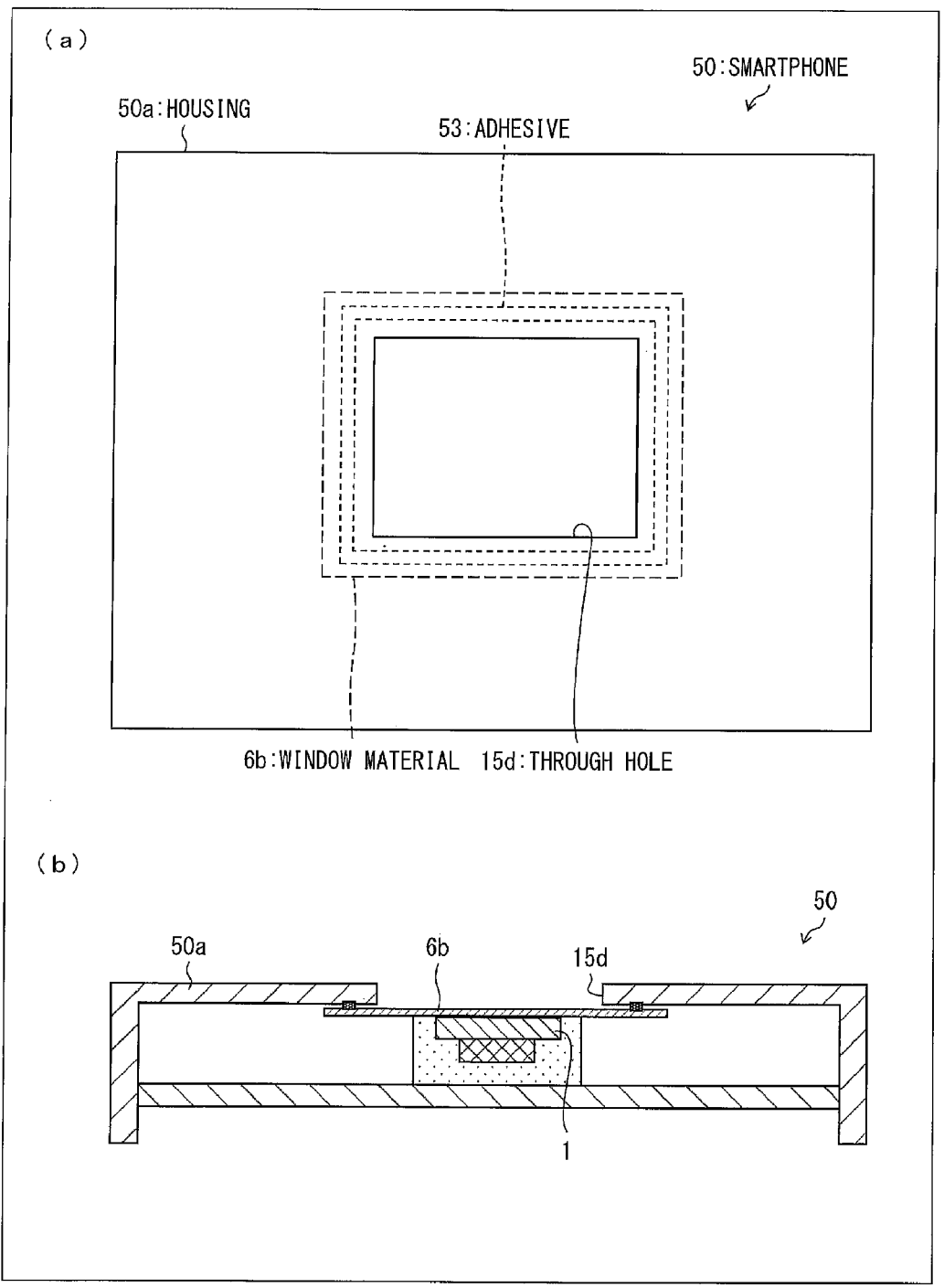
FIG. 19(a) is a plan view for explaining a waterproof adhesion structure of a window material provided in the aforementioned smartphone, and (b) is a sectional view thereof.

FIG. 19(*a*) is a plan view for explaining a waterproof adhesion structure of the window material 6*b* provided in the smartphone 50, and FIG. 19(*b*) is a sectional view thereof. The window material 6*b* is adhered to the inner surface of the housing 50*a* with the adhesive 53 applied once along a peripheral edge of the surface thereof. Thereby, it is possible to attain the dustproof property and the waterproof property. Though an example in which the window material 6*b* and the housing 50*a* of the smartphone 50 are adhered with the adhesive 53 applied once along the peripheral edge of the surface of the window material 6*b* is indicated in FIG. 19(*a*), the invention is not limited thereto. It is needless to say that an adhesive may be further applied along the peripheral edge in an outer peripheral side or an inner peripheral side of the adhesive 53 so that the adhesive is doubly arranged for adhesion.

Note that, in the present embodiment, in order to give the dustproof property and the waterproof property to the electrical jack 10' for the purpose of being able to be mounted particularly to a waterproof portable apparatus, a configuration in which the window material 6 illustrated in FIG. 16 seals the insertion hole 15, that is, the adhesion structure described with FIGS. 19(*a*) and (*b*) is adopted. However, the invention is not limited thereto. In a case where the electrical jack 10' requires only the dustproof property and does not require the waterproof property, that is, in a case where the electrical jack 10' is mounted particularly to a non-waterproof portable apparatus, it is needless to say that what is needed is only adopting a structure such that the window material 6 is merely fixed to the holding body 9, that is, the adhesion structure described with FIGS. 18(*a*) and (*b*).

According to the Wien's displacement law that a product of a wavelength with which a quantity of radiation becomes maximum and temperature at that time is a fixed number, radiation temperature of an object to be measured which emits infrared radiation having a wavelength of 6 to 15 μm is about −80° C. to 300° C. That is, based on the infrared radiation having the wavelength of 6 to 15 μm, which reaches the light reception unit 2, it is possible to measure temperature of the object to be measured, which is about −80° C. to 300° C. Thus, by using the electrical jack 10', it is possible to measure temperature of a frozen food, water temperature, body temperature, temperature of a food cooked by heating, and the like without making contact with the object to be measured. A specific application example will be described in detail below.

The in-electrical jack opening 8' is formed at a bottom of the insertion hole 15 of the electrical jack 10'. A tip end surface of an electrical plug 20' (for example, refer to an electrical plug tip end surface 29 of FIG. 20) which is inserted into the electrical jack 10' is arranged so as to face the light reception unit 2 included in the thermopile 1. To the in-electrical jack opening 8', the above-described window material 6 is fixed with an adhesive. Thereby, intrusion of water into the thermopile 1 and the light reception unit 2 is prevented. It is also possible to prevent intrusion of water into an inner part of a portable apparatus by the window material 6.

In the lead frame 3, the thermopile 1 including the light reception unit 2 which detects infrared radiation of 1 to 15 μm is fixed (die-bonded) at a predetermined position. The thermopile 1 and the lead frame 3 are electrically connected with a wire which is not illustrated. The lead frame 3 is fixed to the substrate 30 and electrically connected to an electronic circuit of an electronic apparatus or a smartphone.

The thermopile 1, the light reception unit 2, and the lead frame 3 are sealed by, for example, epoxy resin, and the light reception unit 2 faces the cavity of sealing resin 5. Thereby, infrared radiation which has been emitted from an object to be measured and is transmitted through the window material 6 passes through the cavity 5 and reaches the light reception unit 2 without being absorbed by the sealing resin 4. Accordingly, it is possible to measure temperature of the object to be measured by using the electrical jack 10'.

The window material 6 is disposed in front of the cavity of sealing resin 5. The window material 6 is fixed to the sealing resin 4 with an adhesive. Thereby, intrusion of dust and water from the insertion hole 15 into the cavity of sealing resin 5 is prevented. The cavity of sealing resin 5 is a space surrounded by the thermopile 1, the light reception unit 2, the sealing resin 4, and the window material 6.

Next, another example of the structure of the vicinity of the light reception unit 2 of the electrical jack 10' will be described by using FIG. 17(b). FIG. 17(b) is a sectional view illustrating a structure of an electrical jack (optical transmission device) 10a' in which the field of view restriction member 7 is arranged in a vicinity of the window material 6 of the electrical jack 10' of FIG. 16. Note that, for convenience of description, the same reference signs are assigned to members having the same functions as those of the members described with FIG. 17(a), and description thereof will be omitted.

The field of view restriction member 7 is a member having a function of restricting an angle at which light radiated from an object to be measured and reaching the light reception unit 2 is made incident on the light reception unit 2. The field of view restriction member 7 illustrated in FIG. 17(b) is provided along the window material 6 so as to be contact with and superimposed on the window material 6, and fixed to the sealing resin 4 with an adhesive. The field of view restriction member 7 is formed by providing many minute through holes (holes P in FIG. 21) by laser-beam machining in a plate which absorbs infrared radiation such as, for example, a polyimide plate. That is, the infrared radiation emitted from the object to be measured is transmitted through the window material 6 and then passes through the through holes provided in the field of view restriction member 7 to reach the light reception unit 2. Note that, a specific example of a structure of the field of view restriction member 7 and a function thereof will be described in detail below.

(Relation Between Electrical Jack 10' and Electrical Plug 20')

Figure 20:
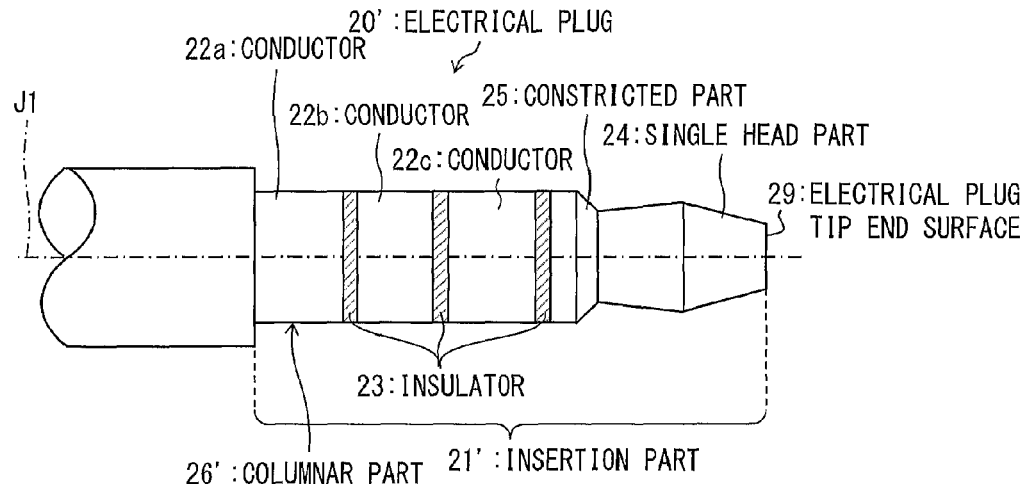
FIG. 20 is a front view illustrating an example of a structure of an electrical plug capable of being inserted into the electrical jack of FIG. 16.
Figure 21:
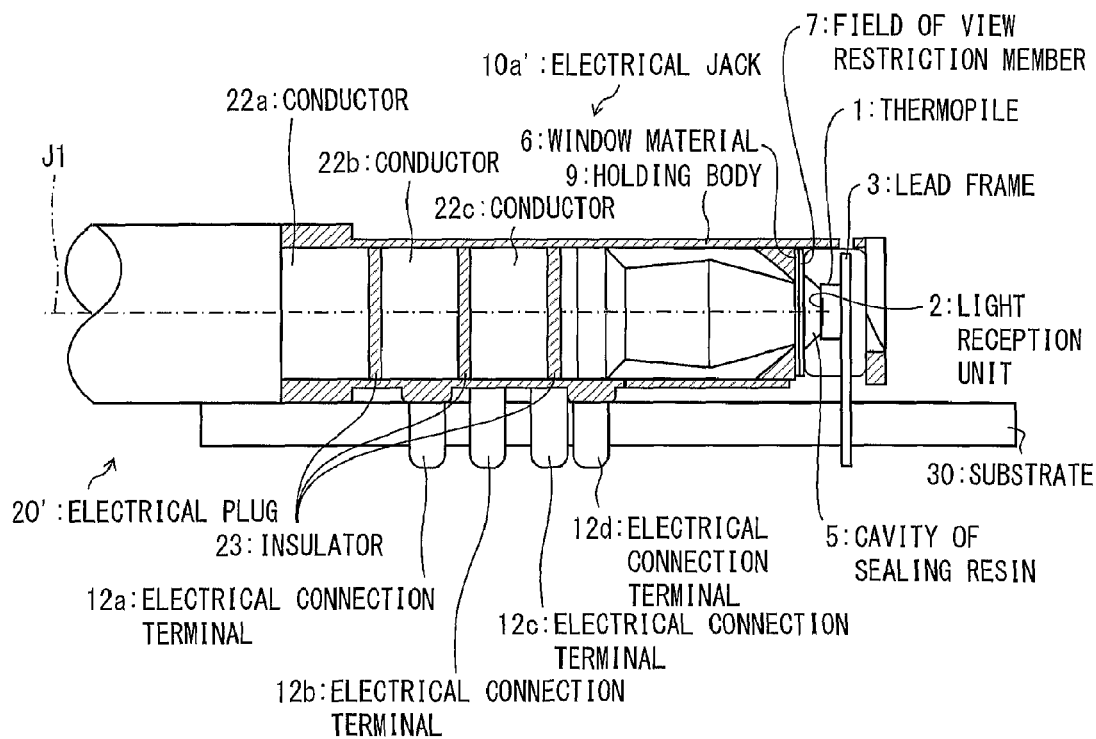
FIG. 21 is a partial sectional view of the electrical plug in the electrical jack, which illustrates a state where the electrical plug illustrated in FIG. 20 is inserted into the electrical jack illustrated in FIG. 17(b).

Next, the electrical plug 20' of a four-pole small-sized single-head type used for electric transmission, which is compatible with the electrical jack 10', will be described briefly by using FIG. 20 and FIG. 21. FIG. 20 is a partial sectional view illustrating an example of a structure of the aforementioned electrical plug 20' capable of being inserted into the electrical jack 10' of FIG. 16. Moreover, FIG. 21 is a sectional view of the electrical jack 10a', which illustrates a state where the electrical plug 20' illustrated in FIG. 20 is inserted into the electrical jack 10a' illustrated in FIG. 17(b).

As illustrated in FIG. 20, the electrical plug 20' includes an insertion part 21' which has a substantially columnar shape. The insertion part 21' has a columnar part 26' having a columnar shape, the single head part 24 which is formed to have a smaller diameter than that of the columnar part 26' in a side of a tip end of the insertion part 21', and a constricted part 25 which is formed between the single head part 24 and the columnar part 26'. Conductive bodies 22a, 22b and 22c are formed in a peripheral surface of the columnar part 26' so as to be arrayed in an axial direction of the columnar part 26'. In the columnar part 26', insulating bodies 23 are formed between the conductive bodies 22a and 22b, between the conductive bodies 22b and 22c, and between the conductor 22c and the constricted part 25.

For example, according to a standard of the OMTP (Open Mobile Terminal Platform), the aforementioned electrical plug 20' includes a GND terminal, a microphone terminal, a right audio terminal, and a left audio terminal. In an example illustrated in FIG. 20, the conductor 22a corresponds to the GND terminal, and the conductor 22b corresponds to the microphone terminal. The conductor 22c corresponds to the right audio terminal, and the single head part 24 corresponds to the left audio terminal. Moreover, according to a standard of the CTIA (Cellular Telecommunications and Internet Association), the conductor 22a corresponds to the microphone terminal, and the conductor 22b corresponds to the GND terminal. The conductor 22c corresponds to the right audio terminal, and the single head part 24 corresponds to the left audio terminal.

The single head part 24 is formed at a site of the electrical plug 20' which is to be inserted into a deepest part of the electrical jack 10a' when the electrical plug 20 is inserted into the electrical jack 10a'. The constricted part 25 is formed in a side of a base part of the single head part 24. That is, the electrical plug 20' has a shape same as that of an insertion part of an existing four-pole small-sized single-head electrical plug, which has been generally distributed.

The electrical connection terminal 12a is electrically connected to the conductor 22a of the electrical jack 10a' inserted into the insertion hole 15. The electrical connection terminal 12b is electrically connected to the conductor 22b. An electrical connection terminal 12c is electrically connected to the conductor 22c. An electrical connection terminal 12d is electrically connected to the single head part 24. The electrical connection terminals 12a to 12d are electrically connected to an electronic circuit of a portable apparatus or a smartphone (not illustrated).

Though illustrated here is the example in which the four electrical connection terminals of the electrical connection terminals 12a to 12d are included, the number of electrical connection terminals may be one to three or five or more without particular limitation.

That is, the insertion hole 15 is configured so that the electrical plug 20' of a small-sized single-head type used for electric transmission is able to be inserted thereinto, and includes one or more electrical connection terminals which are configured so as to allow electrical connection to the aforementioned electrical plug inserted into the insertion hole 15.

When the electrical plug 20' is inserted into the insertion hole 15 of the electrical jack 10a', the electrical plug 20' is held inside the holding body 9 as illustrated in FIG. 21. At this time, the conductor 22a, the conductor 22b, the conductor 22c, and the single head part 24 of the electrical plug 20' are electrically connected to the electrical connection terminals 12a, 12b, 12c, and 12d of the electrical jack 10a', respectively, and function as, for example, an input terminal of an earphone.

However, the electrical jack according to the invention is not limited to the electrical jack which is compatible with the four-pole small-sized single-head electrical plug in conformity to the standard of the OMTP or the standard of the CTIA. The electrical jack according to the invention is applicable also to an electrical jack which is compatible with, for example, a three-pole small-sized single-head electrical plug or a four-pole small-sized single-head electrical plug.

(As to Field of View of Light Reception Unit 2)

Figure 22:
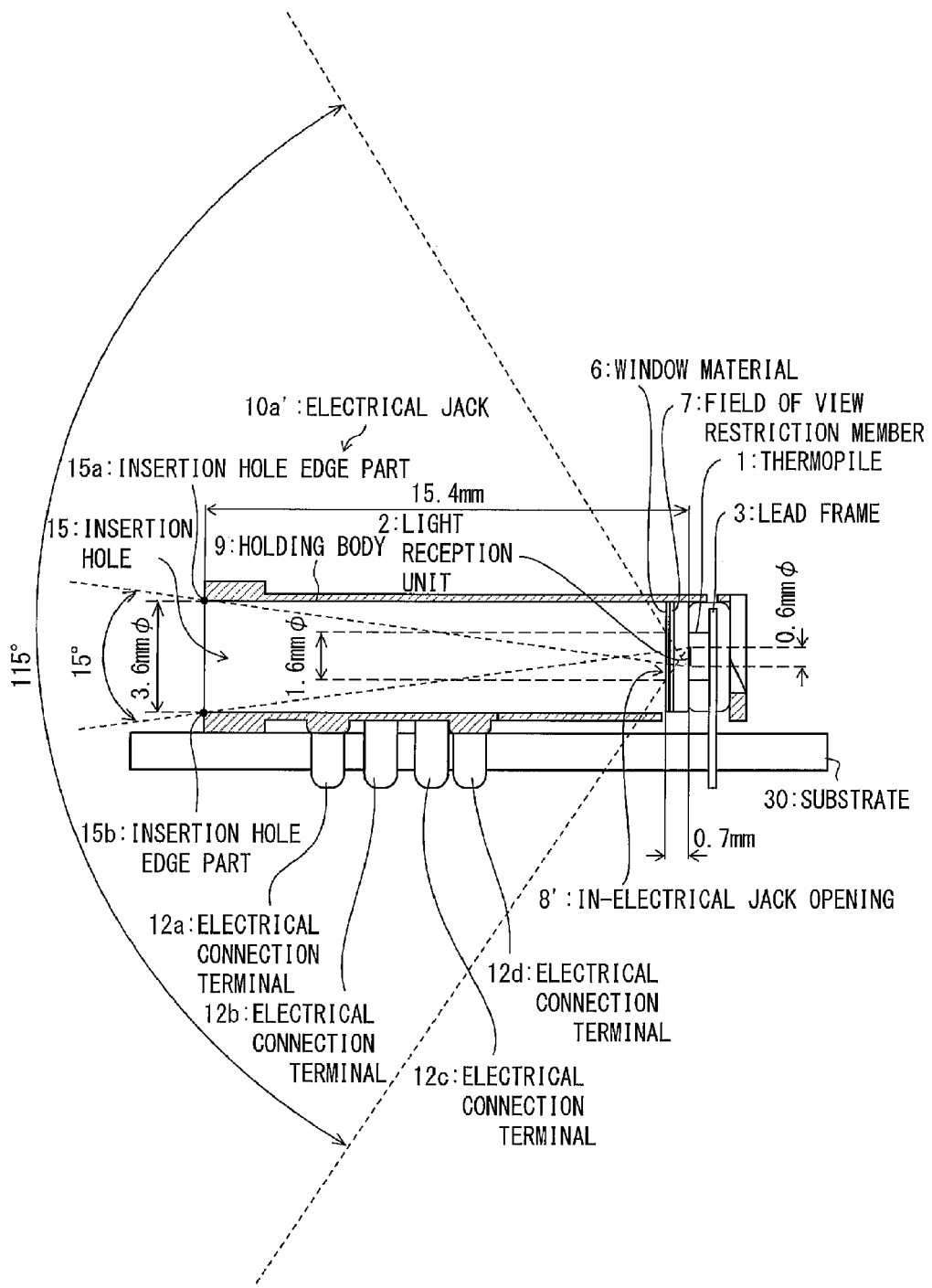
FIG. 22 is a sectional view for explaining an FOV of a light reception unit of a thermopile provided in the electrical jack illustrated in FIG. 17(b).
Figure 23:
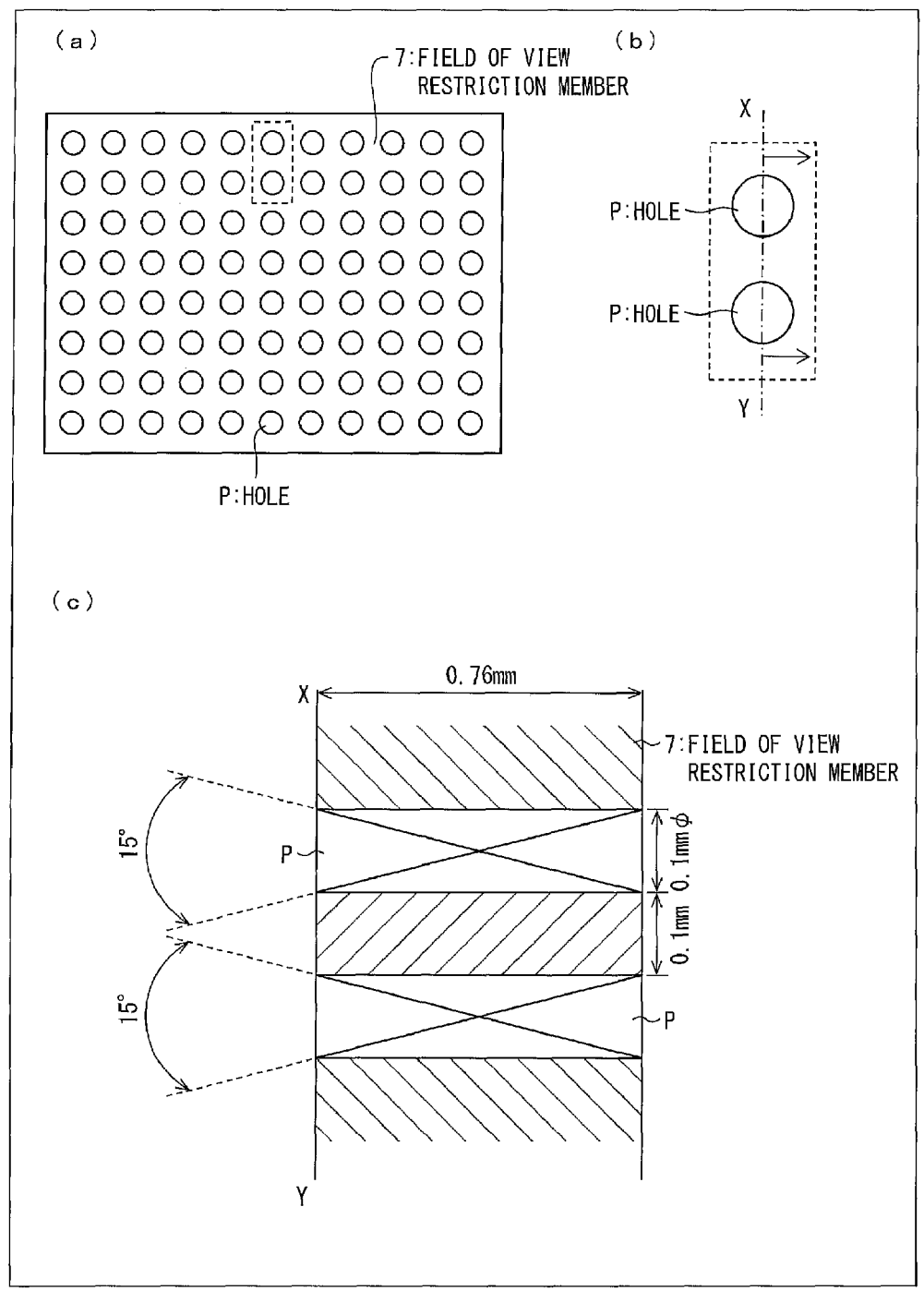
FIG. 23(a) is a view illustrating a part of an appearance structure of the field of view restriction member, (b) is a view which is further extraction of a part of the field of view restriction member illustrated in (a), and (c) is a sectional view when a section of the field of view restriction member taken along an XY axis illustrated in (b) is viewed from an arrow direction.

Next, description will be given for, in a case where a plug such as the electrical plug 20' is not inserted into the insertion hole 15 of the electrical jack 10a', an incident angle of infrared radiation which can be made incident on the light reception unit 2, that is, a field of view (FOV) of the light reception unit 2 of the electrical jack 10a'. Here, the FOV of the light reception unit 2 is a maximum value of a difference of incident angles of light incident on the light reception unit 2. FIG. 22 is a sectional view for explaining the FOV of the light reception unit 2 of the thermopile 1 provided in the electrical jack 10a' illustrated in FIG. 17(b).

In an example illustrated in FIG. 22, it is set that a light receiving diameter which is a diameter of the light reception unit 2 of the thermopile 1 is 0.6 mm, an inner diameter (diameter) of the insertion hole 15 of the jack 10a' is 3.6 mm, and a shortest distance from a line connecting the insertion hole edge part 15a and the insertion hole edge part 15b to a surface of the light reception unit 2 of the thermopile 1 is 15.4 mm. In addition, it is set that an opening diameter (diameter) of the in-electrical jack opening 8' is 1.6 mm, and a distance between the opening of the in-electrical jack opening 8' and the light reception unit 2 of the thermopile 1 is 0.7 mm.

Since infrared radiation emitted from an object to be measured which is arranged outside an entrance of the insertion hole 15 of the electrical jack 10a' and reaching the light reception unit 2 passes through the entrance of the insertion hole 15, the FOV of the light reception unit 2 becomes about 15° as illustrated in FIG. 22. That is, since the light reception unit 2 is provided at a bottom part of the insertion hole 15 which is formed in the electrical jack 10a' and which has a depth, the FOV of the light reception unit 2 is restricted.

On the other hand, in a case where the field of view restriction member 7 is not provided, since the light reception unit 2 receives infrared radiation which passes through the in-electrical jack opening 8', the FOV becomes about 115° in the example illustrated in FIG. 22. Accordingly, in addition to infrared radiation emitted from the object to be measured which is arranged outside the entrance of the insertion hole 15, infrared radiation emitted from the inner peripheral surface of the insertion hole 15 which is formed in the holding body 9 is also made incident on the light reception unit 2.

In a case where, in a radiation temperature sensor having a cylindrical shape like the electrical jack 10a', a sensor receiving infrared radiation is provided deep in the cylinder, it is devised such that, by setting an inner peripheral surface of the cylinder as a mirror surface, an amount of infrared radiation emitted from the inner peripheral surface of the cylinder is relatively reduced. However, the cylinder having the inner peripheral surface set as the mirror surface becomes a light guiding path of infrared radiation, resulting that an FOV becomes widened. Then, in order to prevent the FOV from being widened, a lens for restricting a field of view of infrared radiation incident on the sensor receiving infrared radiation is normally provided in an entrance of the cylinder. However, the electrical jack 10a' is also used with the electrical plug 20' inserted thereinto, so that it is unable to block the insertion hole 15 by providing the aforementioned lens, for example, near the insertion hole edge part 15a. Then, it is considered to restrict the FOV of the light reception unit 2 to 15° by providing a thin optical system such as the silicon diffraction lens 70 (FIG. 34) in the in-electrical jack opening 8'.

However, in the case of providing the silicon diffraction lens 70 in the in-electrical jack opening 8', it is necessary to set a distance between the silicon diffraction lens 70 and the light reception unit 2 long. Thus, it becomes necessary to set a depth of the electrical jack 10a' longer than a depth of a commercial electrical jack. Moreover, a problem of design that an optical axis of the light reception unit 2 and the silicon diffraction lens 70 requires to be adjusted is posed. This will be described briefly below by using FIG. 34.

FIG. 34 is a view for explaining a distance between the light reception unit 2 and the silicon diffraction lens 70 in a case where the FOV of the light reception unit 2 is restricted to 15° by providing the silicon diffraction lens 70 in the in-electrical jack opening 8' in the electrical jack 10a' of FIG. 22.

In FIG. 34, the optical axis is adjusted so that infrared radiation passing through the center of the silicon diffraction lens 70 reaches the center of the light reception unit 2. When the diameter of the light reception unit 2 is 0.6 mm, a distance L between the light reception unit 2 and the silicon diffraction lens 70, which is necessary for setting an angle θ to be 7.5°, is about 2.3 mm. Accordingly, compared to the example illustrated in FIG. 22, in which the distance between the in-electrical jack opening 8' and the light reception unit 2 is 0.7 mm, it becomes necessary to set the electrical jack 10a' longer by 1.5 mm or more. Then, in the electrical jack 10a' according to the present embodiment, applied is the field of view restriction member 7 which suppresses an increase in a length of the depth of the electrical jack 10a' and which does not cause a problem of adjustment of the optical axis.

(Structure of Field of View Restriction Member 7)

Next, an example of a structure of the field of view restriction member 7 provided in the electrical jack 10a' will be described by using FIG. 23(a), (b), and (c). FIG. 23(a) is a view illustrating a part of an appearance structure of the field of view restriction member 7, (b) is a view which is further extraction of a part of the field of view restriction member 7 illustrated in (a), and (c) is a sectional view when a section of the field of view restriction member 7 taken along an XY axis illustrated in (b) is viewed from an arrow direction.

The field of view restriction member 7 is a plate-shaped member provided in the in-electrical jack opening 8', and restricts an angle of infrared radiation passing through the field of view restriction member 7 to thereby restrict the FOV of the light reception unit 2. Differently from the window material 6 formed of a material which transmits infrared radiation, the field of view restriction member 7 is formed of a material which absorbs infrared radiation, and is provided with many minute holes P (through holes) as illustrated in FIGS. 23(a) and (b) by laser-beam machining or the like. Among infrared radiation which is transmitted through the window material 6, infrared radiation which has passed through the holes P is made to enter the cavity of sealing resin 5 and reaches the light reception unit 2.

Though a polyimide plate material or the like, which has a property of absorbing infrared radiation, can be used for the field of view restriction member 7, this is merely an example, and any material which absorbs and does not transmit infrared radiation is able to be used as a material of the field of view restriction member 7. However, it is desirable to use a material which generates a small amount of heat when the field of view restriction member 7 absorbs infrared radiation. An example of the material which generates a small amount of heat includes glass which has higher thermal conductivity than that of resin.

The FOV of the light reception unit 2 is restricted according to a ratio of a thickness of the field of view restriction member 7 and a diameter of the provided hole P (aspect ratio), and a relation of tan(FOV/2)=(the diameter of the hole P provided in the field of view restriction member 7)/(the thickness of the field of view restriction member 7) is established. Here, tan(FOV/2) is a tangent of an angle of (FOV/2). FIG. 23(c) illustrates an example of the field of view restriction member 7 which restricts a maximum incident angle of infrared radiation to 15° or less. In a case where the diameter of the hole P is 0.1 mm, and a shortest distance between adjacent holes P, that is, a pitch is 0.1 mm, it is found that the thickness of the field of view restriction member 7 needs to be about 0.76 mm or more.

That is, it is possible to express the field of view restriction member 7 included in the electrical jack 10a' in a following manner. It may be configured such that, when a maximum angle of an angle formed by a direction of infrared radiation which straightly advances from outside the entrance of the insertion hole 15 and is then made incident on the light reception unit 2 and a normal line of a light reception surface of the light reception unit 2 is set as X° (in FIG. 23(c), X=7.5°), the field of view restriction member 7 is provided with the hole P which is almost parallel to the normal line of the light reception surface of the light reception unit 2, and a ratio of a width of the hole P (in FIG. 23(c), 0.1 mm) and a length of the hole P (in FIG. 23(c), 0.76 mm) in a section when the hole P is cut along a plane including the normal line is equal to or less than tan(X°).

In this manner, the electrical jack 10a' in one aspect includes the field of view restriction member 7 which is provided with many of the holes P each having almost the same aspect ratio and whose holes P respectively have the aspect ratio of tan(FOV/2). With such a configuration, infrared radiation whose angle difference from infrared radiation perpendicularly incident on the light reception unit 2 is equal to or more than FOV/2 is not able to pass through the holes P of the field of view restriction member 7 and does not reach the light reception unit 2. Thus, even when a plug such as the optical plug 20 is not inserted into the insertion hole 15 of the electrical jack 10a', it is possible to restrict the FOV of the light reception unit 2. Accordingly, by turning the entrance of the insertion hole 15 in a direction toward an object to be measured, it is possible to receive only infrared radiation from the object to be measured by the light reception unit 2 and measure temperature thereof.

Moreover, by providing the field of view restriction member 7, it is possible to suppress an increase in the length of the depth of the electrical jack 10a' compared to a case where the above-described silicon diffraction lens 70 is applied. Furthermore, by using the field of view restriction member 7 in which the holes P are provided so as to have shorter pitches therebetween, it is possible to reduce influence by relative positional shift of the field of view restriction member 7 and the light reception unit 2.

In addition, by increasing an aperture ratio of the field of view restriction member 7 to thereby make more infrared radiation from an object to be measured incident on the light reception unit 2, it is possible to improve sensitivity and an S/N ratio. An aperture ratio in the field of view restriction member 7 which is provided with many holes P in circular shapes of the same size will be described here by using FIGS. 24(a) and (b). FIG. 24 is a view for explaining the aperture ratio of the field of view restriction member, in which (a) illustrates a state where the holes P are arrayed in parallel arrangement, and (b) illustrates a state where the holes P are arrayed in 45° staggered arrangement. In FIG. 24, the diameter of the holes P is d and the pitch is p. The aperture ratio (%) in the case of arraying the holes P in the parallel arrangement as illustrated in FIG. 24(a) is obtained as $78.5 \times d^2/p^2$, and in a case where p=0.1 mm and d=0.1 mm, the aperture ratio is calculated as about 19.6%. On the other hand, the aperture ratio (%) in the case of arraying the holes P in the 45° staggered arrangement as illustrated in FIG. 24(b) is obtained as $157 \times d^2/p^2$, and in a case where p=0.1 mm and d=0.1 mm, the aperture ratio is calculated as about 39.3%. Accordingly, it is found that, even when the diameter and the pitch of the holes P are same, the aperture ratio becomes about twice by arraying the holes P in the 45° staggered arrangement, compared with the case of the parallel arrangement. In this manner, in addition to increasing a size of the holes P or narrowing an interval between the holes P, it is possible to increase the aperture ratio of the field of view restriction member 7 by changing arrangement of the holes P.

[Embodiment 9]

Figure 25:
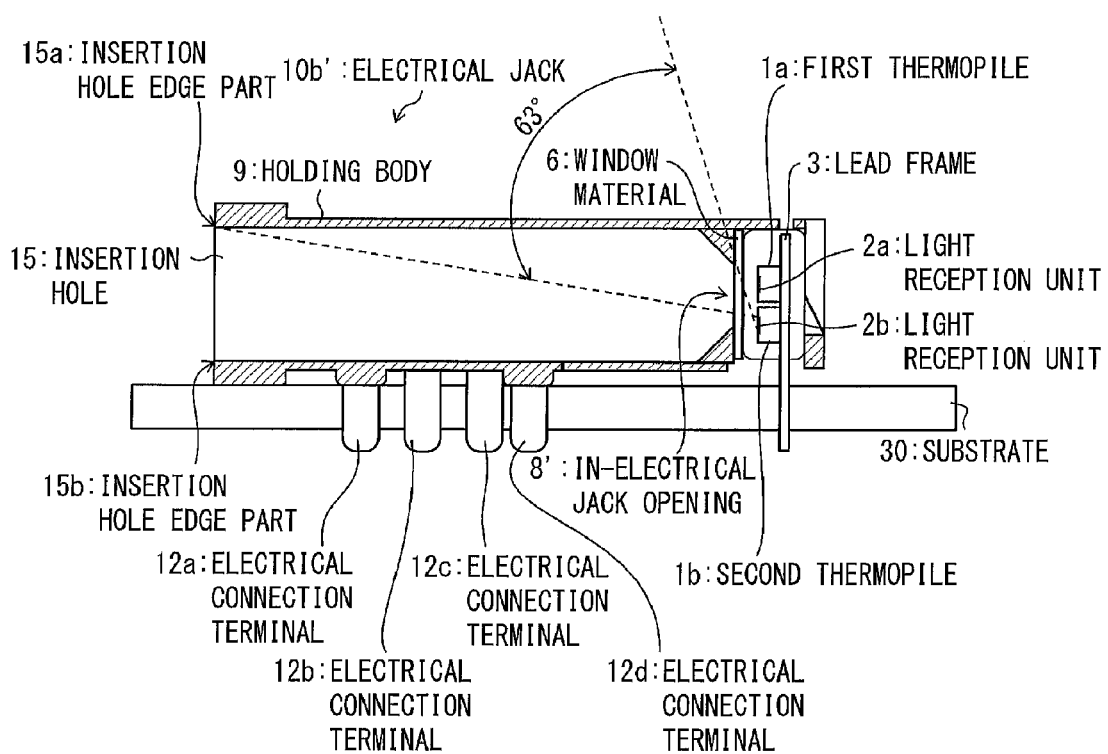
FIG. 25 is a sectional view illustrating an example of a structure of an electrical jack including a first thermopile and a second thermopile according to Embodiment 9.

Still another embodiment of the invention will be described based on FIG. 25 to FIG. 27 as follows. Note that, for convenience of description, the same reference signs are assigned to members having the same functions as those of the members described in the aforementioned embodiments, and description thereof will be omitted.

Described below is an example of a structure of an electrical jack (light reception device) 10b' according to the present embodiment by using FIG. 25. FIG. 25 is a sectional view illustrating an example of the structure of the electrical jack 10b' including the first thermopile 1a and the second thermopile 1b. The electrical jack 10b' is different from the electrical jack 10' illustrated in FIG. 16(a) in that a plurality of thermopiles are included.

The first thermopile 1a is provided with the light reception unit 2a and the second thermopile 1b is provided with the light reception unit 2b. The first thermopile 1a and the light reception unit 2a of the electrical jack 10b' are provided at almost the same positions as those of the thermopile 1 and the light reception unit 2 of the electrical jacks 10' and 10a' according to Embodiment 8 described above. Thus, when a plug such as the electrical plug 20' is not inserted into the insertion hole 15 of the electrical jack 10b', infrared radiation emitted from an object to be measured which exists outside the entrance of the insertion hole 15 of the electrical jack 10b' and infrared radiation from the inner peripheral surface of the insertion hole 15 formed in the holding body 9 are made incident on the light reception unit 2a.

On the other hand, the second thermopile 1b and the light reception unit 2b are provided at positions which allow only infrared radiation from the inner peripheral surface of the insertion hole 15 to be incident when a plug such as the electrical plug 20' is not inserted into the insertion hole 15 of the electrical jack 10b'. For example, in a case where the electrical jack 10b' has the same depth and inner diameter as those of the electrical jack 10a' illustrated in FIG. 21, an FOV of the light reception unit 2b of the second thermopile 1b becomes about 63° as illustrated in FIG. 25.

By using radiant energy of infrared radiation incident on the light reception unit 2b to perform correction of the radiant energy of the infrared radiation incident on the light reception unit 2a, it is possible to offset an amount of radiant energy of infrared radiation incident on the light reception unit 2a from the inner peripheral surface of the insertion hole 15 of the holding body 9 to calculate radiant energy of infrared radiation incident on the light reception unit 2a from an object to be measured. This calibration process will be described in detail below.

(Calibration Process)

The calibration process that the second thermopile 1b is provided, and the radiant energy of the infrared radiation incident on the light reception unit 2a from the object to be measured is calculated by using the radiant energy of the infrared radiation incident on the light reception unit 2b will be described below by using FIG. 26 and FIG. 27. FIG. 26 is a view for explaining an example of the calibration process in the electrical jack 10b' including the second thermopile 1b illustrated in FIG. 25. FIG. 26 illustrates the calibration process for a case where all of temperature T4 and an emissivity α4 of the object to be measured and temperature T3 and an emissivity α3 of the inner peripheral surface of the insertion hole 15 formed in the holding body 9 provided in the electrical jack 10b' are known.

Here, when radiant energy is represented as a function P(T) of temperature T, the radiant energy of the infrared radiation emitted from the object to be measured, which has the temperature T4 and the emissivity α4, is P(T4)×α4. Similarly, the radiant energy of the infrared radiation emitted from the inner peripheral surface of the insertion hole 15 formed in the holding body 9 provided in the electrical jack 10b', which has the temperature T3 and the emissivity α3, is P(T3)×α3.

Since the FOV of the light reception unit 2a and the FOV of the light reception unit 2b are different, an amount of infrared radiation received by the light reception unit 2a and an amount of infrared radiation received by the light reception unit 2b are not the same. Then, when setting a coefficient A and a coefficient B as coefficients indicating correlation between the FOV of the light reception unit 2a and the FOV of the light reception unit 2b, the light reception unit 2a of the first thermopile 1a receives the radiant energy of the infrared radiation, which is expressed by P(T3)×α3×A, from the inner peripheral surface of the insertion hole 15 formed in the holding body 9 provided in the electrical jack 10b'. Similarly, the light reception unit 2b provided in the second thermopile 1b receives the radiant energy of the infrared radiation, which is expressed by P(T3)×α3×B, from the inner peripheral surface of the insertion hole 15 formed in the holding body 9 provided in the electrical jack 10b'.

Accordingly, radiant energy E1 which is received by the light reception unit 2a of the first thermopile 1a is P(T3)×α3×A+P(T4)×α4, and radiant energy E2 which is received by the light reception unit 2b of the second thermopile 1b is P(T3)×α3×B. Thus, it is found that A/B which is a ratio of A and B is able to be obtained by (E1−P(T4)×α4)/E2.

Figure 26:
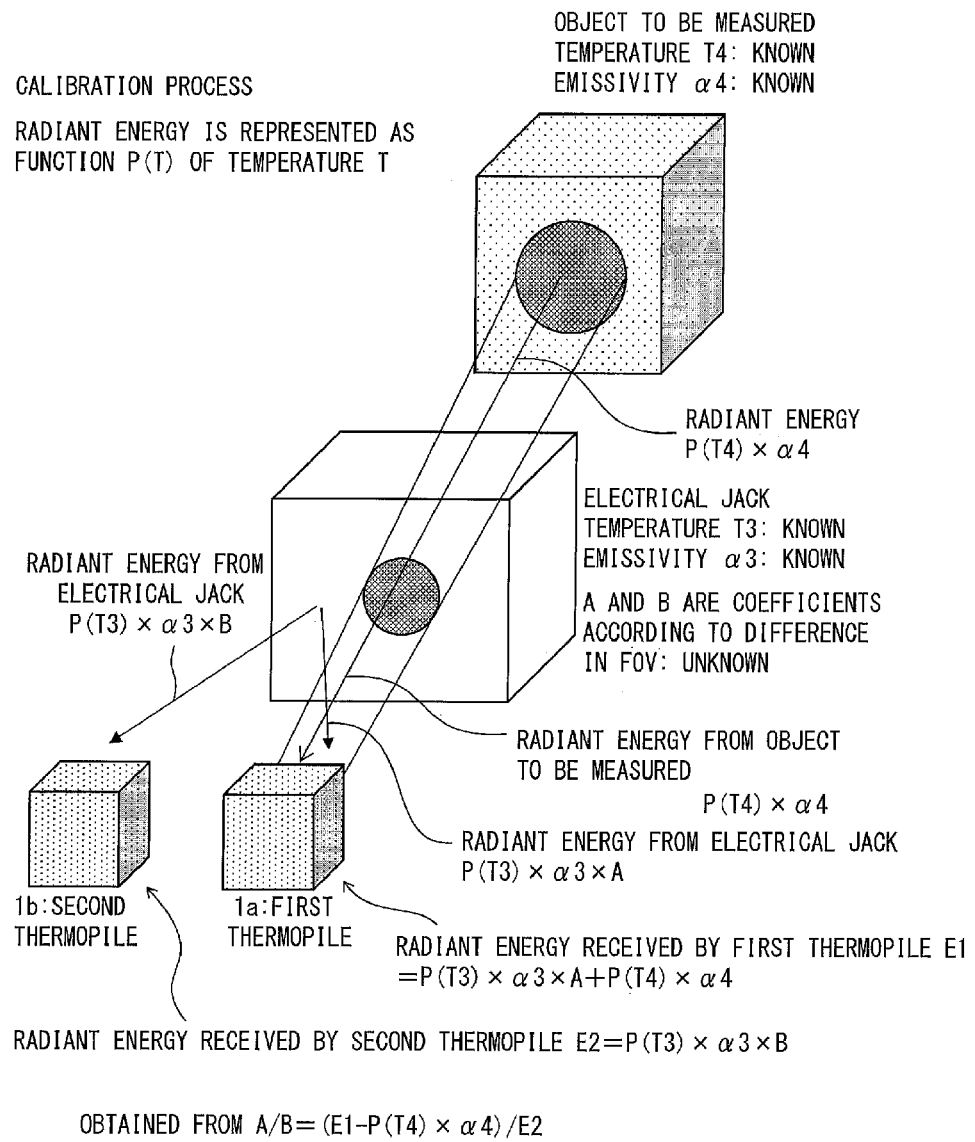
FIG. 26 is a view for explaining an example of a calibration process in the electrical jack including the second thermopile, which is illustrated in FIG. 25.
Figure 27:
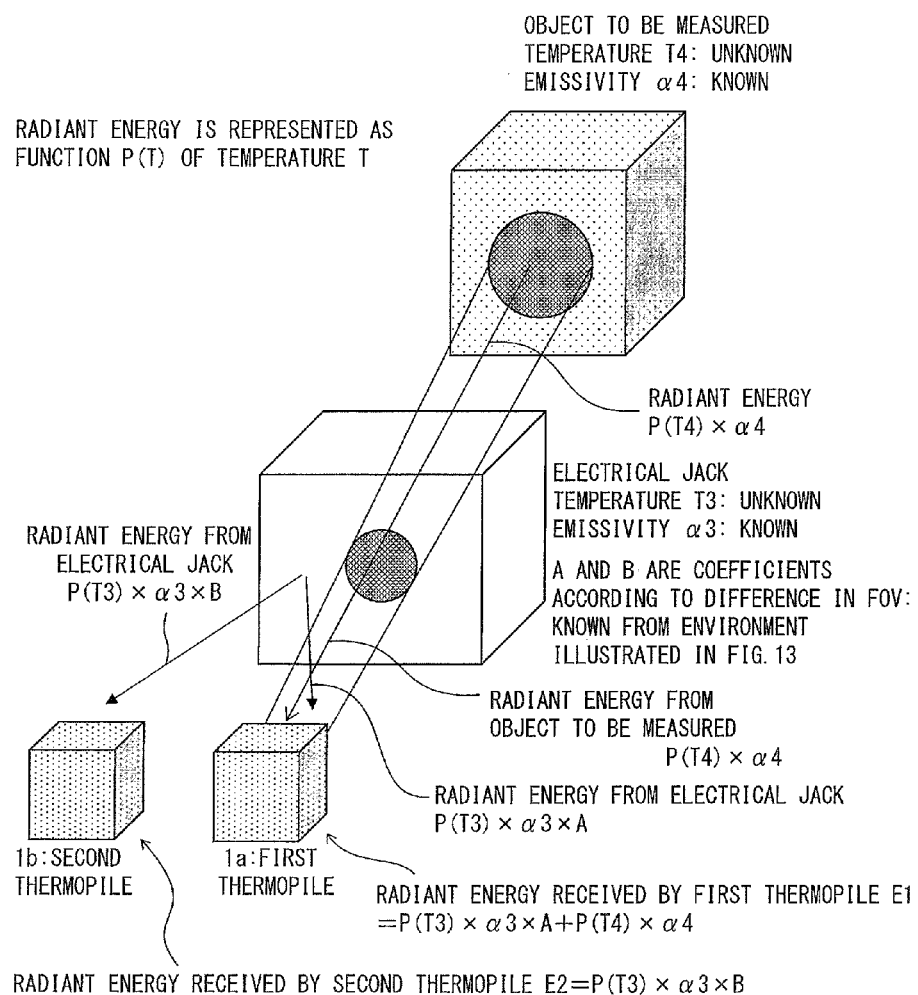
FIG. 27 is a view for explaining an example of measurement by using the electrical jack including the second thermopile, which is illustrated in FIG. 25.

Next, FIG. 27 is a view for explaining an example of measurement by using the electrical jack 10b' including the second thermopile 1b illustrated in FIG. 26. FIG. 27 illustrates an example of measuring the temperature T4 in a case where both of the temperature T3 of the inner peripheral surface of the insertion hole 15 formed in the holding body 9 provided in the electrical jack 10b' and the temperature T4 of the object to be measured are unknown and, on the other hand, both of the emissivities of the inner peripheral surface and the object to be measured are known.

Similarly to FIG. 26, the radiant energy of the infrared radiation emitted from the object to be measured, which has the temperature T4 and the emissivity α4, is P(T4)×α4. Similarly, the radiant energy of the infrared radiation emitted from the inner peripheral surface of the insertion hole 15, which has the temperature T3 and the emissivity α3, is P(T3)×α3. In addition, the radiant energy of the infrared radiation which is received by the light reception unit 2a of the first thermopile 1a from the inner peripheral surface of the insertion hole 15 formed in the holding body 9 provided in the jack 10b' is P(T3)×α3×A. Similarly, the radiant energy of the infrared radiation which is received by the light reception unit 2b of the second thermopile 1b from the inner peripheral surface of the insertion hole 15 formed in the holding body 9 provided in the jack 10b' is P(T3)×α3×B. Accordingly, the radiant energy E1 which is received by the light reception unit 2a of the first thermopile 1a is P(T3)×α3×A+P(T4)×α4, and the radiant energy E2 which is received by the light reception unit 2b of the second thermopile 1b is P(T3)×α3×B. However, there is a difference from FIG. 26 in that the temperature T3 and the temperature T4 are unknown.

When subtracting E2×(A/B) from the radiant energy E1 which is received by the light reception unit 2a of the first thermopile 1a, a value of P(T4)×α4 is obtained as a following formula.

$$E1-E2\times(A/B)=\{P(T3)\times\alpha3\times A+P(T4)\times\alpha4\}-P(T3)\times\alpha3\times B\times(A/B)=P(T4)\times\alpha4$$

Since the emissivity α4 of the object to be measured is known, the temperature T4 is able to be calculated from the value of P(T4)×α4. Note that, a value of A/B is necessary in the above for obtaining P(T4)×α4, and this A/B is able to be obtained in advance by using the calibration process illustrated in FIG. 26. For example, after setting the temperature of the inner peripheral surface of the insertion hole 15 formed in the holding body 9 of the electrical jack 10b' as a predetermined known temperature, infrared radiation from an object to be measured, whose temperature and emissivity are both known, is made incident on the light reception unit 2a. The value of A/B is obtained from the radiant energy E1 which is received by the light reception unit 2a of the first thermopile 1a, the radiant energy E2 which is received by the light reception unit 2b of the second thermopile 1b, and the radiant energy of the infrared radiation emitted from the object to be measured, which are obtained at this time.

Note that, described here is the example in which two thermopiles of the first thermopile 1a and the second thermopile 1b are included and the light reception unit 2b is included at a position at which infrared radiation generated in accordance with temperature of the inner peripheral surface of the insertion hole 15 is detected more than by the light reception unit 2a, but the invention is not limited thereto. It may be configured so that two independent light reception regions are provided on one thermopile and they function as the light reception unit 2a and the light reception unit 2b. Moreover, there is no limitation to the number of thermopiles, and it may be configured to include third and fourth thermopiles, and the like.

[Embodiment 10]

Figure 28:
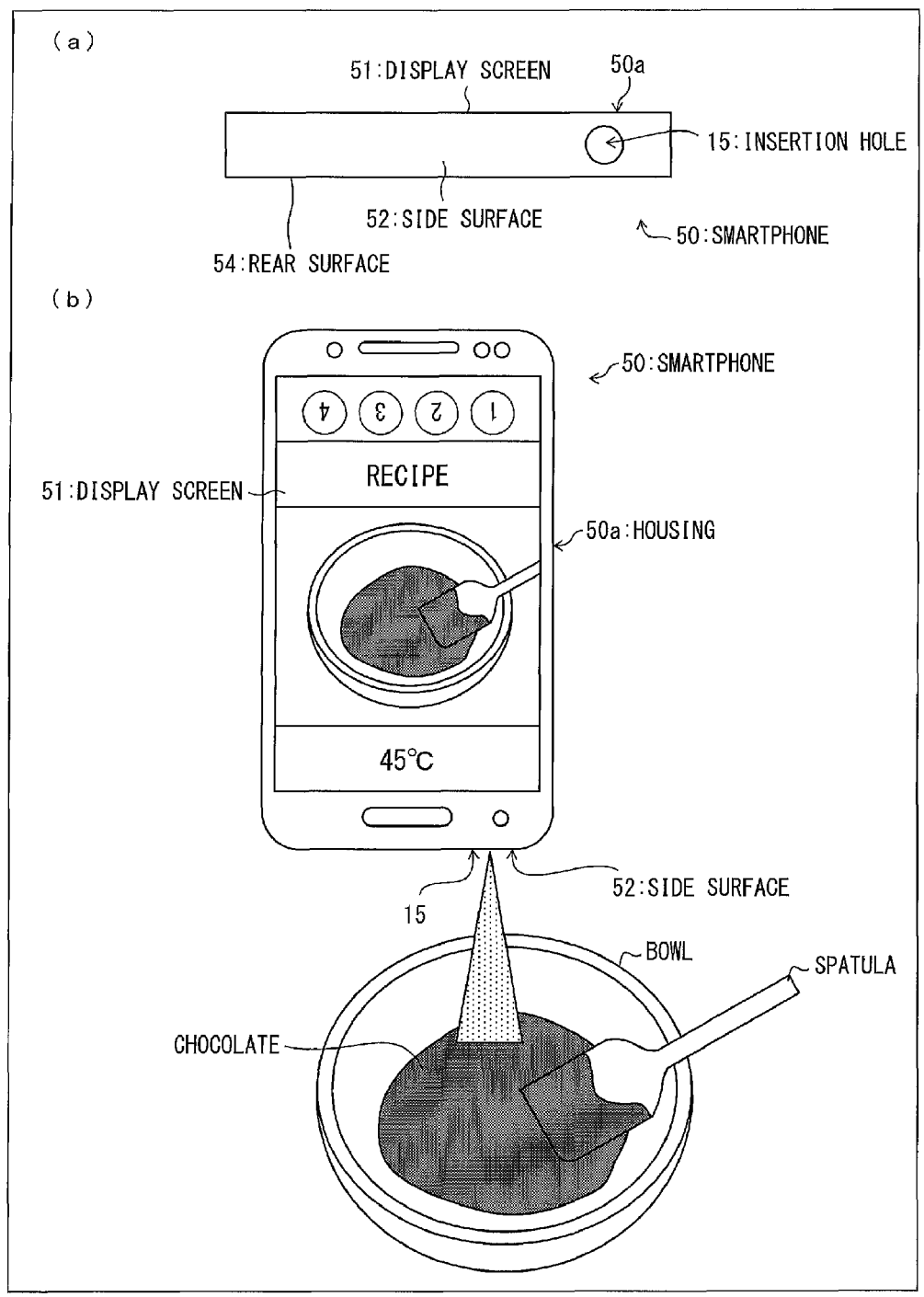
FIG. 28(a) is a view illustrating an example of a position of an insertion hole of an electrical jack provided in a smartphone according to Embodiment 10, and (b) is a view for explaining a state where temperature of an object to be measured is measured by turning the insertion hole illustrated in (a) toward the object to be measured.

Still another embodiment of the invention will be described based on FIG. 28 to FIG. 30 as follows. Described here is an example in which measurement of radiation temperature is performed in a non-contact manner by the smartphone (portable apparatus) 50 which includes the electrical jack 10a' (FIG. 17(b), FIG. 21) with no plug such as the electrical plug 20' (FIG. 20) inserted into the insertion hole 15 formed in the housing 50a. FIG. 28(a) is a view illustrating an example of a position of the insertion hole 15 of the electrical jack 10a' provided in the smartphone 50, and FIG. 28(b) is a view for explaining a state where temperature of an object to be measured is measured by turning the insertion hole 15 illustrated in (a) toward the object to be measured. Note that, for convenience of description, the same reference signs are assigned to members having the same functions as those of the members described in the aforementioned embodiments, and description thereof will be omitted.

As illustrated in FIG. 28(a), in the electrical jack 10a' (FIG. 17(b), FIG. 21), the entrance of the insertion hole 15 of the electrical plug 20' (FIG. 20) is provided in a side surface 52 which is adjacent to a surface including the display screen 51 provided in the housing 50a of the smartphone 50.

Figure 29:
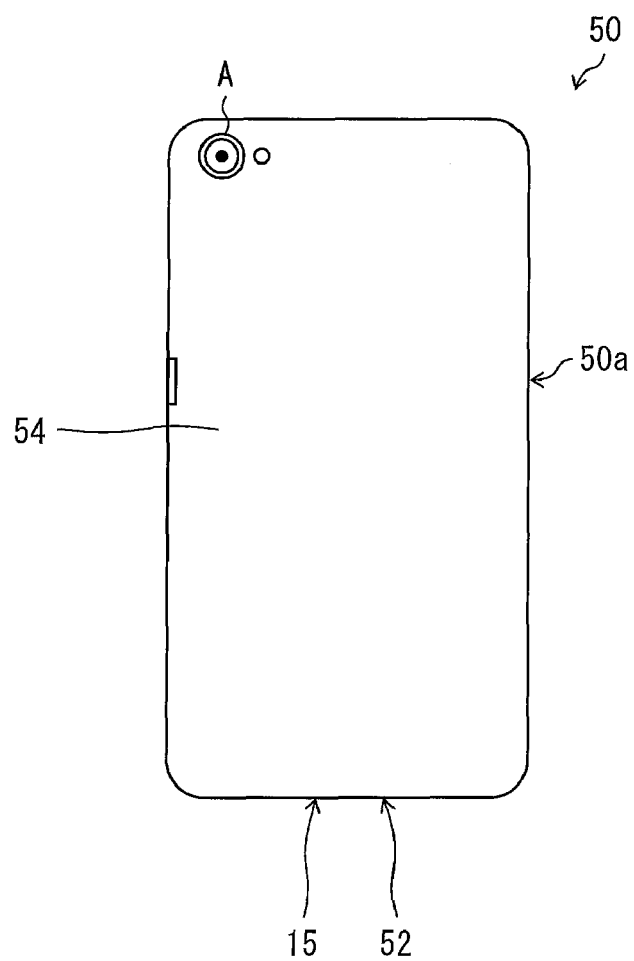
FIG. 29 is a view of a rear surface of the aforementioned smartphone.
Figure 30:
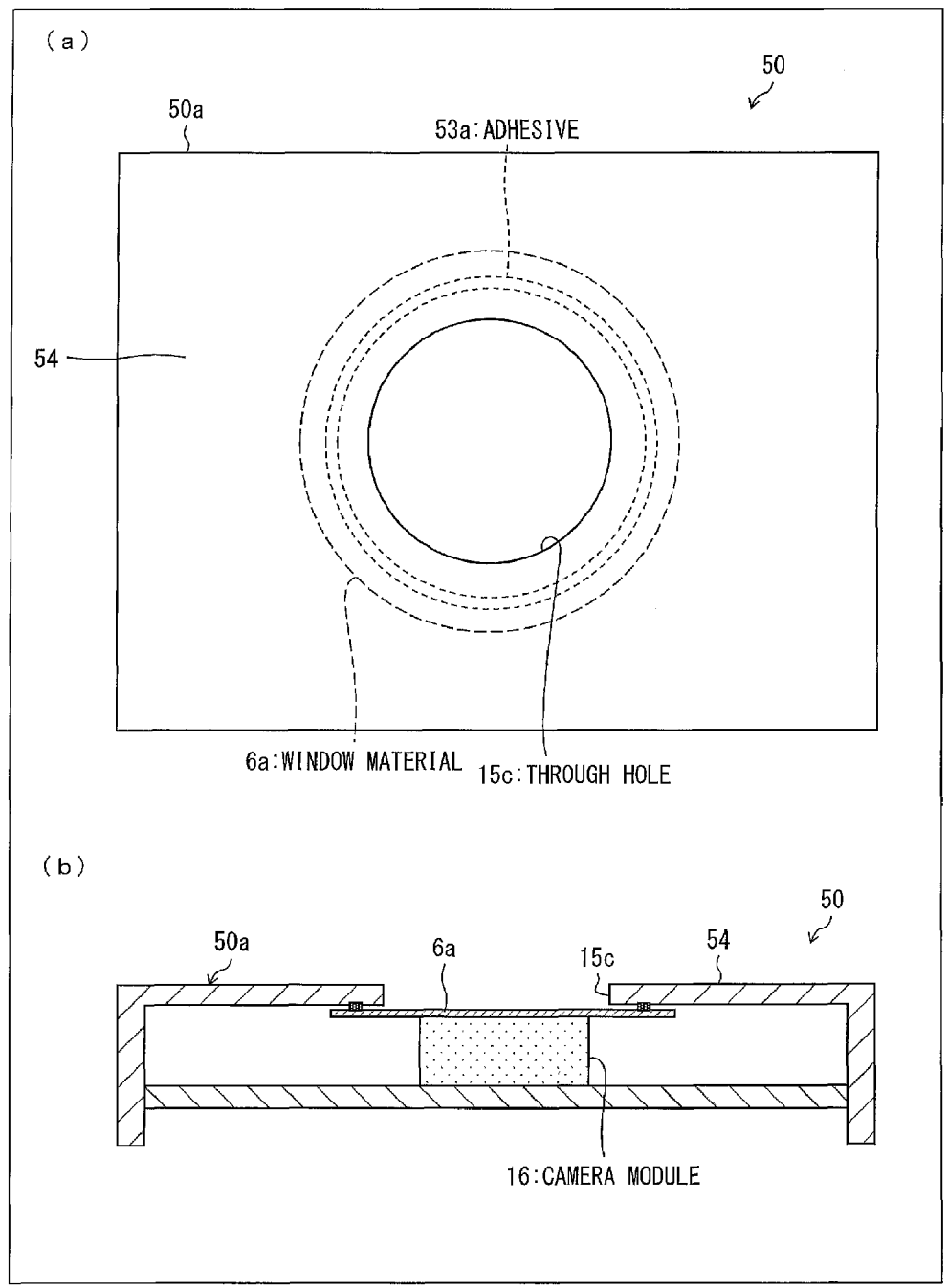
FIG. 30(a) is a schematic view in which a part A illustrated in FIG. 29 is enlarged, and (b) is a sectional view thereof.

FIG. 29 is a view of a rear surface of the smartphone 50. FIG. 30(a) is a schematic view in which a part A illustrated in FIG. 29 is enlarged, and FIG. 30(b) is a sectional view thereof. The housing 50a of the smartphone 50 has a rear surface 54 formed in a side opposite to the display screen 51. In the rear surface 54, a through hole 15c in a circular shape is formed. At a bottom side of the through hole 15c, a window material 6a in a disk shape, which is larger than the through hole 15c, is provided so as to cover the through hole 15c. A camera module 16 which photographs an object by detecting light which is transmitted through the window material 6a is arranged in an inner side of the housing 50a.

The window material 6a is adhered to an inner surface of the housing 50a with an adhesive 53a applied along a peripheral edge of a surface thereof. Transmittance of infrared radiation of the window material 6 (FIG. 16, FIG. 17, FIG. 21, FIG. 22, FIG. 25, FIG. 31, FIG. 32, FIG. 33) provided in the smartphone 50 is higher than transmittance of infrared radiation of the housing 50a. The transmittance of the infrared radiation of the aforementioned window material 6 is higher than transmittance of infrared radiation of the window material 6a which covers a surface of the camera module 16. Note that, another sensor may be provided instead of the camera module 16.

Description will be given here by taking an example of a case where chocolate warmed in a bowl placed in hot water is set as an object to be measured. First, the smartphone 50 executes an application for performing measurement of radiation temperature. Next, when a microprocessor incorporated in the smartphone 50 detects that the electrical plug 20' is not inserted into the insertion hole 15 of the electrical jack 10a', measurement of radiation temperature is started based on an amount of infrared radiation incident from the entrance of the insertion hole 15. In this case, by considering that transmission loss due to transmission by the optical fiber is not generated in the amount of the infrared radiation incident on the light reception unit 2, the radiation temperature of the object to be measured is calculated. Thus, it is possible to correctly measure the temperature of the object to be measured.

As illustrated in FIG. 28(b), other than a measurement result (temperature of 45° C., here), display of information on a recipe or the like may be displayed on the display screen 51 at the same time.

Note that, the electrical jack 10a' includes the window material 6, so that it is possible to prevent, for example, steam from the object to be measured from intruding so far as the thermopile 1 or the light reception unit 2. Thus, the radiation temperature is measured by turning the insertion hole 15, into which a plug such as the electrical plug 20' is not inserted, toward, for example, the object to be measured, which is cooked by heating.

In a case where an emissivity differs depending on a property of an object to be measured (for example, cooked food or the like), an error is caused in a measurement result of radiation temperature. The emissivity here is a ratio of an amount of infrared radiation generated at temperature of a black body to an amount of infrared radiation generated at temperature of a gray body. In such a case, it may be configured such that data indicating an emissivity of cooked food which corresponds to each recipe is held inside the smartphone 50 (for example, a storage unit) or on a cloud and the emissivity for each cooked food is able to be acquired as appropriate.

Note that, though the example in which the jack 10a' is used is described here, the jack 10b' is also applicable. Moreover, though the example in which the window material 6 is arranged at the bottom side of the insertion hole 15 is indicated, the invention in not limited thereto. The window material 6 may be arranged at a bottom side of a concave part formed in the housing 50a.

[Embodiment 11]

Figure 31:
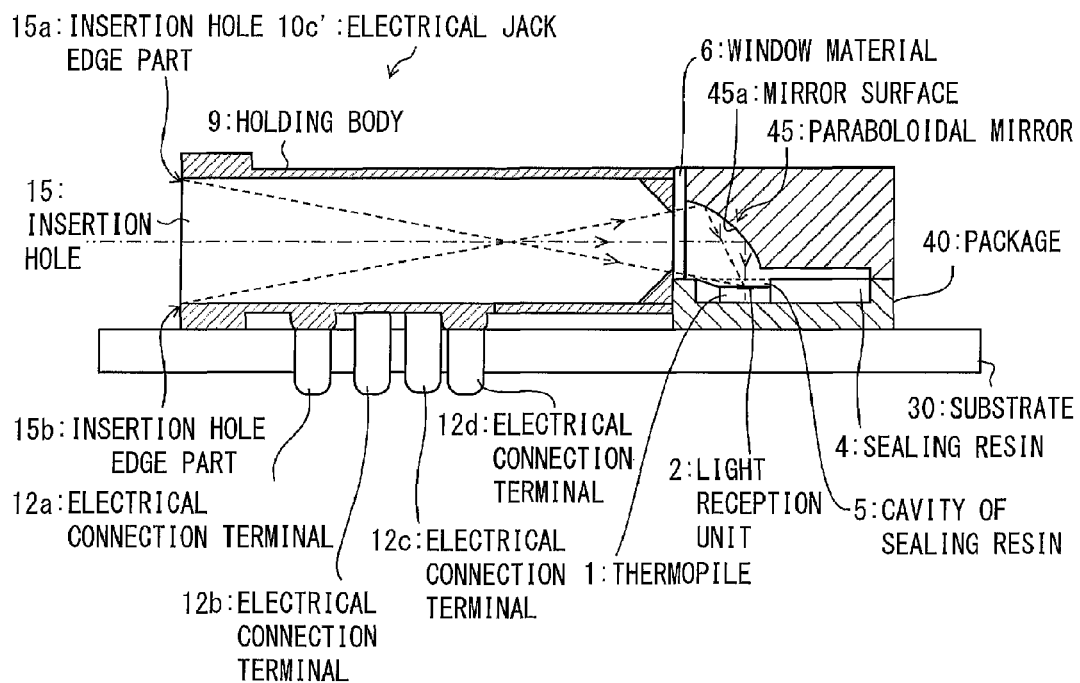
FIG. 31 is a sectional view illustrating an example of a schematic structure of an electrical jack according to Embodiment 11, which includes a paraboloidal mirror surface making infrared radiation incident on a light reception unit.

Still another embodiment of the invention will be described based on FIG. 31 as follows. FIG. 31 is a sectional view illustrating an example of a schematic structure of an electrical jack 10c' which includes a reflection surface making infrared radiation incident on the light reception unit 2. Note that, for convenience of description, the same reference signs are assigned to members having the same functions as those of the members described in the aforementioned embodiments, and description thereof will be omitted.

In the package 40 of the electrical jack (light reception device) 10c', the thermopile 1 including the light reception unit 2 which detects infrared radiation of 1 to 15 μm is fixed to a predetermined position. The thermopile 1 and the package 40 are electrically connected with a wire which is not illustrated. The package 40 is fixed to the substrate 30 and electrically connected to an electronic circuit of a portable terminal or a smartphone (portable apparatus).

In the electrical jack 10c' (light reception device) of FIG. 31, a part of infrared radiation which is transmitted through the window material 6 is reflected by the mirror surface 45a provided in the paraboloidal mirror 45 and made incident on the light reception unit 2. The remaining of the aforementioned infrared radiation is made incident on the light reception unit 2 directly. In a case where a depth in a direction of a center axis of the insertion hole 15 may be deep compared to that of the electrical jacks 10, 10a' and 10b', the structure of the electrical jack 10c' can be also applied.

Moreover, though a configuration in which the window material 6 and the thermopile 1 are arranged at the bottom of the insertion hole 15 on the electrical jacks 10, 10a', 10b', and 10c' is indicated in the aforementioned embodiments, without limitation thereto, it is needless to say that the window material 6 and the thermopile 1 may be arranged at a bottom of an insertion hole of a USB connector. The similar is applied also to embodiments described below.

[Embodiment 12]

Figure 32:
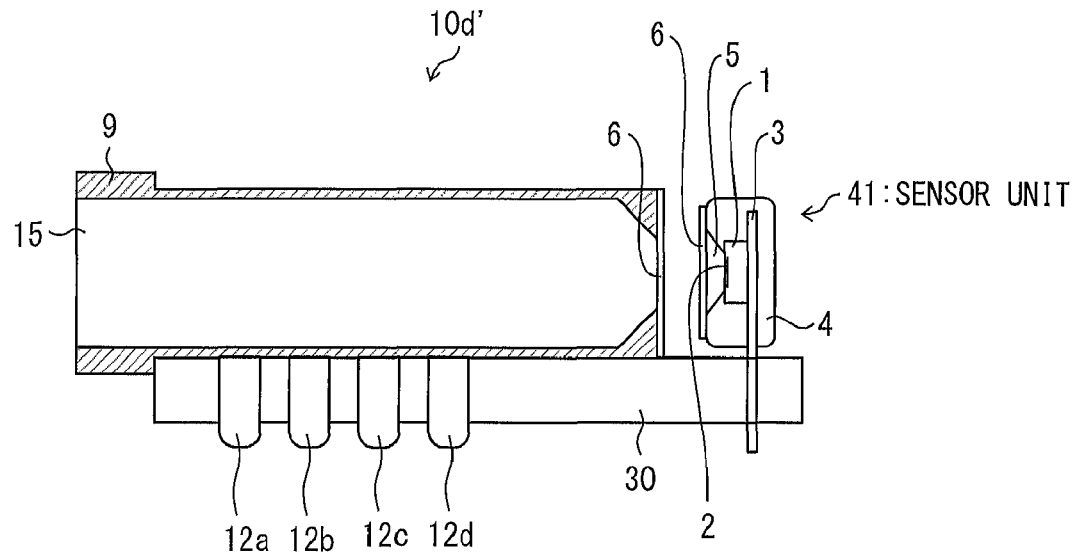
FIG. 32 is a sectional view illustrating an electrical jack according to Embodiment 12.

Still another embodiment of the invention will be described based on FIG. 32 as follows. FIG. 32 is a sectional view illustrating an example of a structure in which the holding body 9 provided in an electrical jack 10d' and a sensor unit 41 including the light reception unit 2 are separated. Note that, for convenience of description, the same reference signs are assigned to members having the same functions as those of the members described in the aforementioned embodiments, and description thereof will be omitted.

To the holding body 9, the window material 6 which transmits infrared radiation of 1 to 15 μm is fixed so as to cover a bottom of the insertion hole 15. The bottom of the insertion hole 15 is covered by the window material 6 as a waterproof sheet so that water or the like coming from the insertion hole 15 does not flow into the sensor unit 41. The sensor unit 41 is fixed to a predetermined position so as to be separated from the window material 6 provided in the holding body 9 of the electrical jack 10d'. The sensor unit 41 includes the window material 6 which transmits infrared radiation of 1 to 15 μm, the thermopile 1 which includes the light reception unit 2 detecting the infrared radiation of 1 to 15 μm, the lead frame 3 to which the thermopile 1 is connected and which is inserted into the substrate 30, and the sealing resin 4 in which the cavity 5 is formed, which encloses the thermopile 1 and which causes the light reception unit 2 to be exposed. The thermopile 1 and the lead frame 3 are electrically connected with a wire which is not illustrated. The lead frame 3 is fixed to the substrate 30, and electrically connected to an electronic circuit of a portable terminal or a smartphone (portable apparatus).

The substrate 30 is provided separately from a substrate of the electronic circuit of the portable terminal or the smartphone (portable apparatus), and the configuration in which the electrical jack 10d' and the sensor unit 41 are mounted on the substrate 30, which is illustrated in FIG. 32, corresponds to the configuration of the aforementioned embodiment, which is illustrated in FIG. 16.

When the aforementioned electrical jack 10d' is set to be waterproof, the holding body 9 and the window material 6 in the holding body side are adhered with a waterproof structure (FIG. 19), and the sealing resin 4 and the window material 6 in the thermopile 1 side are adhered with a non-waterproof structure (FIG. 18) or the waterproof structure.

When the aforementioned electrical jack 10d' is set to be non-waterproof, the holding body 9 and the window material 6 in the holding body side are adhered with the non-waterproof structure or the waterproof structure, and the sealing resin 4 and the window material 6 in the thermopile 1 side are adhered with the non-waterproof structure or the waterproof structure.

[Embodiment 13]

Figure 33:
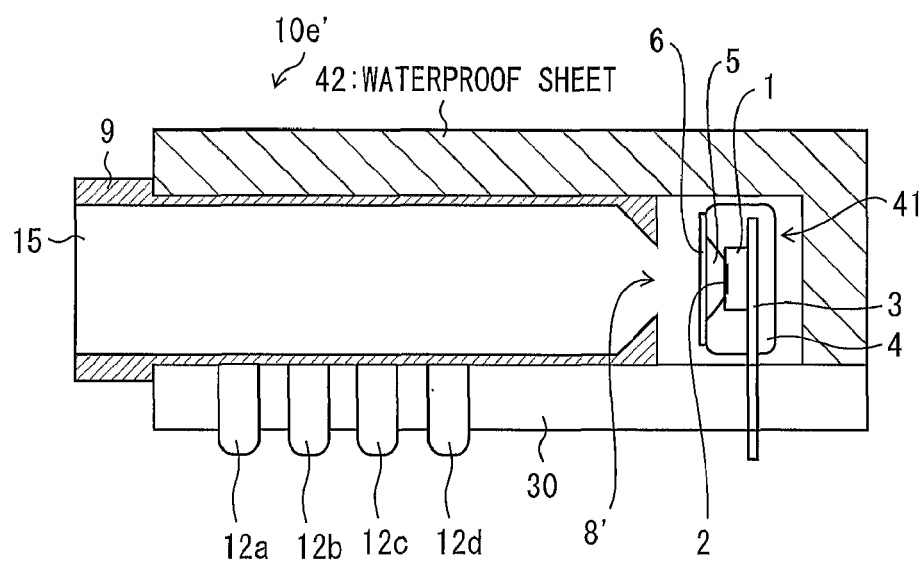
FIG. 33 is a sectional view illustrating an electrical jack according to Embodiment 13.

Still another embodiment of the invention will be described based on FIG. 33 as follows. FIG. 33 is a sectional view illustrating an example of a structure in which the holding body 9 provided in an electrical jack 10e' and a sensor unit 41 including the light reception unit 2 are separated. Note that, for convenience of description, the same reference signs are assigned to members having the same functions as those of the members described in the aforementioned embodiments, and description thereof will be omitted.

In the holding body 9 provided in the electrical jack 10e', the insertion hole 15 through which infrared radiation passes is formed. The sensor unit 41 is fixed to a predetermined position so as to be separated from the holding body 9 of the electrical jack 10e'. The sensor unit 41 includes the window material 6, the thermopile 1 which includes the light reception unit 2, the lead frame 3 to which the thermopile 1 is connected and which is inserted into the substrate 30, the sealing resin 4 in which the cavity 5 is formed, which encloses the thermopile 1 and corresponds to the light reception unit 2, and the window material 6 provided in the sealing resin 4 so as to cover the light reception unit 2. The electrical jack 10e' has a waterproof sheet 42 which is provided in the substrate 30 so as to cover the holding body 9 and the sensor unit 41.

Water or the like which comes into from the insertion hole 15 is to pass through the in-electrical jack opening 8' formed at the bottom of the insertion hole 15 and to be in contact with the sensor unit 41, but the electrical jack 10e' has a structure that, with the waterproof structure (FIG. 19) by the window material 6 attached to the sensor unit 41, water which has passed through the in-electrical jack opening 8' does not flow into inside the thermopile 1. Moreover, the holding body 9, the sensor unit 41, and the substrate 30 are covered by the waterproof sheet 42 so that water or the like which has passed through the in-electrical jack opening 8' of the insertion hole 15 does not flow into inside an electronic circuit of a portable apparatus in which the electrical jack 10e' is provided. However, without limitation to the structure with the waterproof sheet 42, it is needless to say that intrusion of water into the light reception unit 2 may be prevented, for example, by closing the entrance of the insertion hole 15, into which the electrical plug 20' is not inserted, with an elastic sheet (not illustrated).

SUMMARY

An optical transmission device according to an aspect 1 of the invention (jack 10, 10a, 10b, 10c) includes a holding body 9 in which an insertion hole 15 into which an optical fiber plug (optical plug 20) is able to be inserted is formed, a window material 6 through which infrared radiation passing through the insertion hole is transmitted, and a first optical element (light reception unit 2, 2a, 2b) which detects infrared radiation of 6 μm or more and 15 μm or less transmitted through the window material, in which the window material is provided in the holding body so as to prevent water from intruding into the first optical element, and arranged at a bottom of the insertion hole.

Generally, as a window material which has transmissivity of light having a wavelength of 1 to 15 μm and a waterproof property, white or black high density polyethylene, silicon or germanium, which has a metal color, or the like is used. However, since it is not possible to dye the window material by using a dye which absorbs light having a wavelength of 1 to 15 μm, a color of the window material is limited.

With the aforementioned configuration, the window material which transmits infrared radiation heading to the first optical element detecting infrared radiation of 6 μm or more and 15 μm or less, and which prevents water from intruding into the first optical element is arranged at the bottom of the insertion hole. Thereby, the window material whose selectable color is limited and also which is not able to be dyed is not observed in an appearance of an electronic apparatus, so that a color, design, or beauty of the appearance of the electronic apparatus is not affected. Thus, it is applicable to an electronic apparatus of various colors and design.

An optical transmission device according to an aspect 2 of the invention (jack 10a) may further include a field of view restriction member 7 that blocks infrared radiation which is generated in accordance with temperature of an inner surface of the insertion hole and is possible to be incident on the first optical element, in the aspect 1.

With the aforementioned configuration, the field of view restriction member prevents the infrared radiation which is generated in accordance with the temperature of the inner surface of the insertion hole from being incident on the first optical element. Thereby, even in a state where an optical fiber plug is not inserted, the first optical element is able to detect infrared radiation entering the insertion hole from outside the insertion hole without being affected by the temperature of the inner surface of the insertion hole.

An optical transmission device according to an aspect 3 of the invention (jack 10b) may further include a second optical element (light reception unit 2b) which detects infrared radiation generated in accordance with the temperature of the inner surface of the insertion hole more than the first optical element (light reception unit 2a), in the aspect 1.

With the aforementioned configuration, differences are caused in a total amount of infrared radiation detected by each of the first optical element and the second optical element and in a percentage of an amount of the infrared radiation generated in accordance with the temperature of the inner surface of the insertion hole in the total amount of the infrared radiation. Based on the differences, it is possible to estimate an effect on the total amount of the infrared radiation detected by each of the first optical element and the second optical element, which is applied by the amount of the infrared radiation generated in accordance with the temperature of the inner surface of the insertion hole.

An optical transmission device according to an aspect 4 of the invention (jack 10a) may be configured so that, in a case where a maximum angle of an angle formed by a direction of infrared radiation which straightly advances from outside the insertion hole and is then made incident on the first optical element and a normal line of a light reception surface of the first optical element is set as X°, the field of view restriction member is provided with through holes (hole P) which are almost parallel to the normal line of the light reception surface of the first optical element, and a ratio of a width of the through holes and a length of the through holes in a section obtained by cutting the through holes along a plane including the normal line is equal to or less than tan(X°), in the aspect 2.

With the aforementioned configuration, only infrared radiation which has an angle of X° or less with respect to the normal line of the first optical element passes through the through holes of the field of view restriction member. Thereby, it is possible to restrict infrared radiation incident on the first optical element to infrared radiation which straightly advances from outside the insertion hole and is then made incident on the first optical element. On the other hand, the infrared radiation generated in accordance with the temperature of the inner surface of the insertion hole is not able to pass through the through holes, and thus is not made incident on the first optical element. Therefore, even in a state where an optical fiber plug is not inserted, the first optical element is able to detect infrared radiation entering the insertion hole from outside the insertion hole without being affected by the temperature of the inner surface of the insertion hole.

In an optical transmission device according to an aspect 5 of the invention (jack 10, 10a, 10b, 10c), the insertion hole may be configured so as to allow insertion of an electrical plug used for electric transmission thereinto, and a plurality of electrical connection terminals which are composed to be able to be electrically connected to the electrical plug used for electric transmission inserted into the insertion hole (electrical connection terminals 12a and 12b) may be further included, in any one of the aspects 1 to 4.

With the aforementioned configuration, the plurality of electrical connection terminals are provided in the insertion hole. Thereby, the optical transmission device functions also as an optical and electric shared jack which allows electrical connection to the electrical plug used for electric transmission. Accordingly, it is possible to use the electrical plug used for electric transmission and the optical fiber plug by inserting into the same insertion hole.

A light guide plug according to an aspect 6 of the invention (optical plug assembly 25) is an optical plug which is inserted into the insertion hole of the optical transmission device of any one of the aspects 1 to 5, and guides infrared radiation to the first optical element of the optical transmission device, in which an opening E through which the infrared radiation enters, an optical system (mirror M) which changes an advancing direction of the infrared radiation entering the opening, and a mirror surface (mirror surface Rm) in a cylindrical shape which guides the infrared radiation, advancing direction of which is changed by the optical system, to the first optical element may be included.

With the aforementioned configuration, the infrared radiation entering the opening is guided to the first optical element via the mirror surface in a cylindrical shape. Thereby, it is possible to guide, to the first optical element, a part of infrared radiation emitted from a direction in which the opening faces. Thus, it is possible to cause the first optical element to function as a proximity sensor which detects a state of proximity of an object in a periphery or a temperature sensor which detects radiation temperature, from infrared radiation generated by the object.

A light guide plug according to an aspect 7 of the invention may be configured so that an extending direction of the mirror surface in a cylindrical shape is parallel to the normal line of the light reception surface of the first optical element in the aspect 6.

With the aforementioned configuration, the infrared radiation via the mirror surface in a cylindrical shape is guided to the first optical element almost perpendicularly. Thereby, it is possible to form a length of the mirror surface in a cylindrical shape to be short and suppress expansion of the infrared radiation incident on the first optical element. Therefore, it is possible to reduce light guide loss.

An optical fiber plug according to an aspect 8 of the invention (optical plug assembly 25a, 25b) is an optical fiber plug which is inserted into the insertion hole of the optical transmission device of any one of the aspects 1 to 5, and guides infrared radiation to the first optical element of the optical transmission device, which may be configured to include a light collecting unit (the other end of the optical fiber 28a, 28b) which collects the infrared radiation and an optical fiber 21 which guides the infrared radiation incident on the light collecting unit to the first optical element.

With the aforementioned configuration, the infrared radiation incident on the light collecting unit is guided to the first optical element by the optical fiber. Thereby, the light collecting unit and the first optical element are coupled so as to allow optical transmission, so that the light collecting unit and the first optical element are able to be configured so as to be separated from each other.

An optical fiber plug according to an aspect 9 of the invention may be configured so that the light collecting unit collects infrared radiation from a part of a human body, and the optical fiber transmits the infrared radiation into the insertion hole, in the aspect 8.

By using the optical fiber plug in combination with the optical transmission device, it is possible to compose a human detection sensor, a clinical thermometer, or the like.

An optical fiber plug according to an aspect 10 of the invention (optical plug assembly 25a) may be configured so that the light collecting unit collects infrared radiation from an earhole, and the optical fiber transmits the infrared radiation into the insertion hole, in the aspect 8.

By using the optical fiber plug in combination with the optical transmission device, it is possible to compose an ear thermometer.

An optical fiber plug according to an aspect 11 of the invention (optical plug assembly 25b) may be configured so that the light collecting unit collects infrared radiation from an oral cavity, and the optical fiber transmits the infrared radiation into the insertion hole, in the aspect 8.

By using the optical fiber plug in combination with the optical transmission device, it is possible to compose a basal thermometer.

An optical transmission system according to an aspect 12 of the invention may be configured to, by inserting the light guide plug of the aspect 6 or 7 or the optical fiber plug of any one of the aspects 8 to 11 into the insertion hole of the optical transmission device of any one of the aspects 1 to 5, transmit infrared radiation incident on the light guide plug which guides the infrared radiation or the optical fiber plug to the first optical element of the optical transmission device.

The optical transmission system in which the optical transmission device and the optical plug or the optical transmission device and the optical fiber plug are combined is able to compose a temperature sensor, a proximity sensor, a clinical thermometer, or the like, based on detection of infrared radiation.

An electronic apparatus according to an aspect 13 of the invention (smartphone 50) is an electronic apparatus which uses the optical transmission system of the aspect 12 as various detection means, which is also in the scope of the invention.

A light reception device according to an aspect 14 of the invention (electrical jack 10') includes a holding body 9 in which an insertion hole 15 is formed, a window material 6 which is arranged at a bottom side of the insertion hole 15 and through which infrared radiation passing through the insertion hole 15 is transmitted, and an infrared sensor (thermopile 1) which detects the infrared radiation transmitted through the window material 6.

With the aforementioned configuration, the window material which transmits infrared radiation passing through the insertion hole and heading to the infrared sensor is arranged at the bottom side of the insertion hole. Therefore, the window material arranged at the bottom side of the insertion hole is not visually recognized from outside the light reception device. As a result thereof, the window material makes it possible to give a dustproof property and infrared transmissivity to the infrared sensor without affecting a color or design of an appearance of a portable apparatus in which the light reception device is provided.

Moreover, by detecting an object to be detected by the infrared sensor (thermopile 1, 1a, 1b) via the insertion hole 15, it becomes possible to narrow a field of view for infrared radiation by the insertion hole 15, thus making it possible to set a measurement distance to the object to be detected to be long.

In a light reception device according to an aspect 15 of the invention (electrical jack 10'), it is preferable that, in the aspect 14, the window material 6 seals the bottom of the insertion hole 15.

With the aforementioned configuration, since the bottom of the insertion hole is sealed by the window material, it is possible to prevent water into the insertion hole from intruding into the infrared sensor, thus making it possible to give a waterproof property.

In a light reception device according to an aspect 16 of the invention (electrical jack 10'), it is preferable that, in the aspect 14, the window material 6 is arranged at a position separated from the bottom so as to oppose the bottom of the insertion hole 15 and cover the infrared sensor (thermopile 1).

With the aforementioned configuration, since the window material covers the infrared sensor, it is possible to prevent water into the insertion hole from intruding into the infrared sensor.

In a light reception device according to an aspect 17 of the invention (electrical jack 10'), it is preferable that the insertion hole 15 allows insertion of an electrical plug used for electric transmission (electrical plug 20') thereinto, the light reception device further includes electrical connection terminals 12a to 12d which are electrically connected to the electrical plug 20' inserted into the insertion hole 15, and a length of the insertion hole 15 is longer than a length of an insertion part 21' of the electrical plug 20' and shorter than a length of an insertion part of an optical plug used for optical transmission.

With the aforementioned configuration, since the length of the insertion hole is longer than the length of the insertion part of the electrical plug, it is possible to insert the insertion part 21' of the electrical plug into the insertion hole completely. Thus, only by arranging the window material and the infrared sensor (thermopile 1, 1a, 1b) at a bottom side of an existing electrical jack 10', both of a function of electric transmission and a function of infrared detection are able to be provided. Note that, since the length of the insertion hole is shorter than the length of the insertion part of the optical plug used for optical transmission, an entire of the insertion part of the optical plug used for optical transmission is not able to be inserted into the insertion hole, so that a user is able to easily recognize erroneous insertion of the optical plug used for optical transmission.

In a light reception device according to an aspect 18 of the invention (electrical jack 10'), it is preferable that the insertion hole allows insertion of an electrical plug used for electric transmission thereinto, and a depth of the insertion hole is equal to or more than the length of the insertion part of the optical plug used for optical transmission.

With the aforementioned configuration, since the depth of the insertion hole is equal to or more than the length of the insertion part of the optical plug used for optical transmission, it is possible to prevent a tip end of the optical plug used for optical transmission from abutting the window material and damaging the window material when the optical plug used for optical transmission is inserted into the insertion hole.

In a light reception device according to an aspect 19 of the invention (electrical jack 10'), it is preferable that the window material 6 is arranged so as to prevent water into the insertion hole 15 from intruding into the infrared sensor (thermopile 1).

With the aforementioned configuration, it is possible to prevent deterioration of the infrared sensor, which is caused by the water into the insertion hole.

In a light reception device according to an aspect 20 of the invention (electrical jack 10'), it is preferable that the insertion hole 15 allows insertion of the electrical plug used for electric transmission (electrical plug 20') thereinto, the electrical plug 20' includes the insertion part 21' in a columnar shape, which is compatible with the insertion hole 15, a first conductor (conductor 22a) and a second conductor (conductor 22b) which are formed in an outer peripheral surface of the insertion part 21' so as to array in an axial direction of the insertion part 21', and an insulator 23 which is formed in the outer peripheral surface in order to insulate the first conductor (conductor 22a) and the second conductor (conductor 22b), and a first electrical connection terminal (electrical connection terminal 12a) which is able to be electrically connected to the first conductor (conductor 22a) and a second electrical connection terminal (electrical connection terminal 12b) which is able to be electrically connected to the second conductor (conductor 22b) are provided in the holding body 9.

In a portable apparatus according to an aspect 21 of the invention (smartphone 50), a window material 6, through which infrared radiation passing through a concave part formed in a housing 50a is transmitted, is arranged at a bottom side of the concave part, and an infrared sensor (thermopile 1) which detects the infrared radiation transmitted through the window material 6 is provided.

In a portable apparatus according to an aspect 22 of the invention (smartphone 50), a window material 6, through which infrared radiation passing through an insertion hole 15 formed in a side surface 52 of a housing 50a is transmitted, is arranged at a bottom side of the insertion hole 15, and an infrared sensor (thermopile 1) which detects the infrared radiation transmitted through the window material 6 is provided.

In a portable apparatus according to an aspect 23 of the invention (smartphone 50), it is preferable that transmittance of infrared radiation of the window material 6 is higher than transmittance of infrared radiation of another window material 6a provided in the housing 50a.

With the aforementioned configuration, it is possible to correctly detect temperature and set a measurement distance to an object to be detected to be long.

In a portable apparatus according to an aspect 24 of the invention (smartphone 50), it is preferable that a waterproof sheet 42 which prevents water into the insertion hole 15 from intruding into the housing 50a.

With the aforementioned configuration, it is possible to prevent malfunction of an electronic circuit of the portable apparatus, which is caused by the water into the insertion hole.

The invention is not limited to each of the embodiments described above and can be modified variously within the scope indicated in the claims, and embodiments obtained by appropriately combining technical means disclosed in different embodiments are also included in the technical scope of the invention. Further, by combining the technical means disclosed in each of the embodiments, a new technical feature may be formed.

INDUSTRIAL APPLICABILITY

The invention is able to be used for a plug-jack system mounted on a portable apparatus such as a portable telephone, a smartphone, or a tablet.

In addition, the invention is able to be used for a light reception device, and particularly able to be used for a light reception device which receives infrared radiation.

REFERENCE SIGNS LIST 1, 1a, 1b thermopile (infrared sensor)
2, 2a light reception unit (first optical element)
2b light reception unit (second optical element)
3 lead frame
6 window material
6a window material (another window material)
6b window material
7 field of view restriction member
9 holding body
10, 10a, 10b, 10c jack (optical transmission device)
10', 10a' to 10e' electrical jack (light reception device)
12a to 12d electrical connection terminal
15 insertion hole
15c through hole
15d through hole
16 camera module
20 optical plug (optical fiber plug)
20' electrical plug
21 optical fiber
21' insertion part
22a to 22d conductor
25 optical plug assembly (light guide plug)
25a, 25b optical plug assembly (optical fiber plug)
28a, 28b other end of optical fiber (light collecting unit)
50 smartphone (electronic apparatus, portable apparatus)
50a housing
E opening
M mirror (optical system)
P hole (through hole)
Rm mirror surface

The invention claimed is:

1. An optical transmission device, comprising
a holding body having an insertion hole into which an optical fiber plug is able to be inserted,
a window material through which infrared radiation passing through the insertion hole is transmitted, and
a first optical element which detects infrared radiation of 6 μm or more and 15 μm or less transmitted through the window material, wherein
the window material is provided in the holding body so as to prevent water from intruding into the first optical element, and arranged at a bottom of the insertion hole, and
a field of view restriction member that blocks infrared radiation which is generated in accordance with temperature of an inner surface of the insertion hole and is possible to be incident on the first optical element is further included.

2. A light guide plug which is inserted into the insertion hole of the optical transmission device according to claim 1, and guides infrared radiation to the first optical element of the optical transmission device, comprising
an opening through which the infrared radiation enters,
an optical system which changes an advancing direction of the infrared radiation entering the opening, and
a mirror surface in a cylindrical shape which guides the infrared radiation, advancing direction of which is changed by the optical system, to the first optical element.

3. An optical fiber plug which is inserted into the insertion hole of the optical transmission device according to claim 1, and guides infrared radiation to the first optical element of the optical transmission device, comprising
a light collecting unit which collects the infrared radiation, and
an optical fiber which guides the infrared radiation incident on the light collecting unit to the first optical element.

4. An optical transmission device, comprising
a holding body having an insertion hole into which an optical fiber plug is able to be inserted,
a window material through which infrared radiation passing through the insertion hole is transmitted, and
a first optical element which detects infrared radiation of 6 μm or more and 15 μm or less transmitted through the window material, wherein
the window material is provided in the holding body so as to prevent water from intruding into the first optical element, and arranged at a bottom of the insertion hole, and
a second optical element which detects infrared radiation generated in accordance with temperature of an inner surface of the insertion hole more than the first optical element is further included.

5. A light reception device, comprising
a holding body in which an insertion hole is formed,
a window material which is arranged at a bottom side of the insertion hole and through which infrared radiation passing through the insertion hole is transmitted,
an infrared sensor which detects the infrared radiation transmitted through the window material, and
a field of view restriction member that blocks infrared radiation which is generated in accordance with temperature of an inner surface of the insertion hole and is possible to be incident on the infrared sensor.

6. The light reception device according to claim 5, wherein the window material seals the bottom of the insertion hole.

7. A portable apparatus, wherein a window material, through which infrared radiation passing through a concave part formed in a housing is transmitted, is arranged at a bottom side of the concave part, and an infrared sensor which detects the infrared radiation transmitted through the window material is provided, and
a field of view restriction member that blocks infrared radiation which is generated in accordance with temperature of an inner surface of the concave part and is possible to be incident on the infrared sensor is further provided.

8. The portable apparatus according to claim 7, wherein transmittance of infrared radiation of the window material is higher than transmittance of infrared radiation of another window material provided in the housing.

9. A portable apparatus, wherein a window material, through which infrared radiation passing through an insertion hole formed in a side surface of a housing is transmitted, is arranged at a bottom side of the insertion hole, and an infrared sensor which detects the infrared radiation transmitted through the window material is provided, and
a field of view restriction member that blocks infrared radiation which is generated in accordance with temperature of an inner surface of the insertion hole and is possible to be incident on the infrared sensor is further provided.

10. A light reception device, comprising
a holding body in which an insertion hole is formed,
a window material which is arranged at a bottom side of the insertion hole and through which infrared radiation passing through the insertion hole is transmitted, and
an infrared sensor which detects the infrared radiation transmitted through the window material, wherein
the infrared sensor includes a first optical element which detects infrared radiation transmitted through the window material and a second optical element which detects infrared radiation generated in accordance with temperature of an inner surface of the insertion hole more than the first optical element.

11. The light reception device according to claim 10, wherein the window material seals the bottom of the insertion hole.

12. A portable apparatus, wherein a window material, through which infrared radiation passing through a concave part formed in a housing is transmitted, is arranged at a bottom side of the concave part, and an infrared sensor which detects the infrared radiation transmitted through the window material is provided, and
the infrared sensor includes a first optical element which detects infrared radiation transmitted through the window material and a second optical element which detects infrared radiation generated in accordance with temperature of an inner surface of the concave part more than the first optical element.

13. The portable apparatus according to claim 12, wherein transmittance of infrared radiation of the window material is higher than transmittance of infrared radiation of another window material provided in the housing.

14. A portable apparatus, wherein a window material, through which infrared radiation passing through an insertion hole formed in a side surface of a housing is transmitted, is arranged at a bottom side of the insertion hole, and an infrared sensor which detects the infrared radiation transmitted through the window material is provided, and
the infrared sensor includes a first optical element which detects infrared radiation transmitted through the window material and a second optical element which detects infrared radiation generated in accordance with temperature of an inner surface of the insertion hole more than the first optical element.

15. An electrical jack, comprising
a holding body in which an insertion hole is formed,
a window material which is arranged at a bottom side of the insertion hole and through which infrared radiation passing through the insertion hole is transmitted,
the insertion hole allowing insertion of an electrical plug, and
an electrical connection terminal which is electrically connected to the electrical plug in a case where the electrical plug is inserted, wherein
a thermopile which, in a case where the insertion hole is open, detects infrared radiation transmitted through the window material is further included.

16. The electrical jack according to claim 15, wherein the window material seals the bottom of the insertion hole.

17. A portable apparatus comprising the electrical jack according to claim 15.

18. An electrical jack, comprising
a holding body in which an insertion hole is formed,
a window material which is arranged at a bottom side of the insertion hole and through which infrared radiation passing through the insertion hole is transmitted,
the insertion hole allowing insertion of an electrical plug, and
an electrical connection terminal which is electrically connected to the electrical plug in a case where the electrical plug is inserted, wherein
a thermopile which, in a case where the insertion hole is open, detects infrared radiation outside via the insertion hole is further included.

* * * * *